(12) United States Patent
Ferrari et al.

(10) Patent No.: US 10,143,658 B2
(45) Date of Patent: Dec. 4, 2018

(54) MULTISTAGE DELIVERY OF ACTIVE AGENTS

(71) Applicants: Board of Regents of the University of Texas System, Austin, TX (US); The Ohio State University Research Foundation, Columbus, OH (US)

(72) Inventors: Mauro Ferrari, Houston, TX (US); Ennio Tasciotti, Houston, TX (US); Jason Sakamoto, Houston, TX (US)

(73) Assignees: Board of Regents of the University of Texas System, Austin, TX (US); The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 14/725,570

(22) Filed: May 29, 2015

(65) Prior Publication Data
US 2016/0051481 A1 Feb. 25, 2016

Related U.S. Application Data

(63) Continuation of application No. 11/836,004, filed on Aug. 8, 2007, now abandoned.

(60) Provisional application No. 60/821,750, filed on Aug. 8, 2006, provisional application No. 60/914,348, filed on Apr. 27, 2007.

(51) Int. Cl.
| | |
|---|---|
| *A61K 9/127* | (2006.01) |
| *A61K 9/50* | (2006.01) |
| *A61K 9/51* | (2006.01) |
| *A61K 31/165* | (2006.01) |
| *A61K 31/704* | (2006.01) |
| *A61K 31/7088* | (2006.01) |

(52) U.S. Cl.
CPC .............. *A61K 9/50* (2013.01); *A61K 9/127* (2013.01); *A61K 9/1271* (2013.01); *A61K 9/51* (2013.01); *A61K 31/165* (2013.01); *A61K 31/704* (2013.01); *A61K 31/7088* (2013.01)

(58) Field of Classification Search
CPC .............. A61K 31/165; A61K 31/704; A61K 31/7088; A61K 9/127; A61K 9/1271; A61K 9/50; A61K 9/51; A61K 424/45; A61K 424/489; A61K 514/34; A61K 514/44
USPC ........................ 514/34, 44 A; 424/450, 489
See application file for complete search history.

(56) References Cited

U.S. PATENT DOCUMENTS

| | | | |
|---|---|---|---|
| 6,099,864 A | 8/2000 | Morrison et al. | |
| 6,107,102 A | 8/2000 | Ferrari | |
| 6,355,270 B1 * | 3/2002 | Ferrari ................ | A61K 9/0097 424/185.1 |
| 6,395,302 B1 * | 5/2002 | Hennink et al. ....... | A61K 9/127 264/4.1 |
| 2003/0059386 A1 * | 3/2003 | Sumian ................ | A61K 8/0241 424/70.1 |
| 2003/0114366 A1 * | 6/2003 | Martin ................. | A61K 9/0097 424/489 |
| 2005/0178287 A1 * | 8/2005 | Anderson ............ | A61K 8/0241 106/31.03 |
| 2008/0280140 A1 | 11/2008 | Ferrari et al. | |

FOREIGN PATENT DOCUMENTS

| | | | |
|---|---|---|---|
| EP | 855179 | 7/1998 | |
| WO | WO 2007/120248 | 10/2007 | |
| WO | WO 2008/054874 | 5/2008 | |
| WO | WO 2008054874 A2 * | 5/2008 | ............... A61K 8/11 |

OTHER PUBLICATIONS

Akerman et al., "Nanocrystal targeting in vivo," Proc. Natl. Acad. Sci. USA, Oct. 1, 2002, 99(20):12617-12621.
Alley et al., "Feasibility of Drug Screening with Panels of Human tumor Cell Lines Using a Microculture Tetrazolium Assay," Cancer Research, Feb. 1, 1988, 48:589-601.
Becker et al., "Peptide-polymer bioconjugates: hybrid block copolymers generated via living radical polymerizations from resin-supported peptides," Chem. Commun. (Camb), 2003:180-181.
Behrens et al., "Measuring a colloidal particle's interaction with a flat surface under nonequilibrium conditions," Eur. Phys. J. E, 2003, 10:115-121.
Bianco et al., "Monoclonal antibodies targeting the epidermal growth factor receptor," Curr Drug Targets, 2005, 6:275-287.
Bradbury, J., "Nanoshell destruction of inoperable tumours," Lancet Oneel, Dec. 2003, 4:711.
Buriak, J.M., "Organometallic chemistry on silicon and germanium surfaces," Chem. Rev . May 2002, 102(5): 1271-1308.
Canham, L. T., "Bioactive silicon structure fabrication through nanoetching techniques," Advanced Materials, 1995, 7(12):1033-1037.
Charnay et al., "Reduced Symmetry Metallodielectric Nanoparticles: Chemical Synthesis and Plasmonic Properties," J. Phys. Chem. B, 2003, 107:7327-7333.
Chen et al. "Soluble ultra-short single-walled carbon nanotubes," J. Am. Chem. Soc., 2006, 128:10568-10571.
Cheng et al. "Nanotechnologies for biomolecular detection and medical diagnostics," Curr. Opin. Chem. Biol., 2006, 10:11-19.
Chiapponi et al., "Tailored porous silicon microparticles: fabrication and properties", Chemphyschem., Apr. 6, 2010, v. 11, No. 5, pp. 1029-1035.
Ciardiello et al., "A novel approach in the treatment of cancer: targeting the epidermal growth factor receptor," Clin. Cancer Res., Oct. 2001, 7:2958-2670.

(Continued)

*Primary Examiner* — Janet L Epps-Smith
(74) *Attorney, Agent, or Firm* — Winstead PC

(57) ABSTRACT

Multistage delivery vehicles are disclosed which include a first stage particle and a second stage particle. The first stage particle is a micro or nanoparticle that contains the second stage particle. The second stage particle includes an active agent, such as a therapeutic agent or an imaging agent. The multistage delivery vehicle allows sequential overcoming or bypassing of biological barriers. The multistage delivery vehicle is administered as a part of a composition that includes a plurality of the vehicles. Methods of making the multistage delivery vehicles are also provided.

28 Claims, 58 Drawing Sheets

(56) References Cited

OTHER PUBLICATIONS

Cloninger M.J., "Biological applications of dendrimers," Curr. Opin. Chem. Biol., 2002, 6:742-748.
Cohen et al., "Microfabrication of Silicon-Based Nanoporous Particulates for Medical Applications," Biomedical Microdevices, 2003, 5(3):253-259.
Corot et al., "Recent advances in iron oxide nanocrystal technology for medical imaging," Adv. Drug Deliv. Rev., 2006, 58:1471-1504.
Corrie et al., "Quantitative analysis and characterization of biofunctionalized fluorescent silica particles," Langmuir, 2006, 22:2731-2737.
Cullis et al,. "The structural and luminescence properties of porous silicon," J. Appl. Phys., Aug. 1, 1997, 82(3):909-965.
Decuzzi et al., "A theoretical model for the margination of particles within blood vessels," Ann. Biomed. Eng., Feb. 2005, 33(2):179-90.
Decuzzi et al., "Adhesion of microfabricated particles on vascular endothelium: a parametric analysis," Ann. Biomed. Eng., Jun. 2004, 32(6):793-802.
Decuzzi et al., "Fantastic voyages, Nanodevices in development today promise to give medicine capabilities that were once purely in the realm of fiction," Mechanical Engineering, Oct. 2006, 128:24-27.
Decuzzi et al., "The adhesive strength of non-spherical particles mediated by specific interactions," Biomaterials, 2006, 27:5307-5314.
Decuzzi et al., "The effective dispersion of nanovectors within the tumor microvasculature," Ann. Biomed. Eng., Apr. 4, 2006, 34(4):633-641.
Decuzzi et al., "The role of specific and non-specific interactions in receptor-mediated endocytosis of nanoparticles," Biomaterials, 2007, 28:2915-2922.
Derfus et al., "Probing the Cytotoxicity of Semiconductor Quantum Dots," Nano Lett., 2004, 4(1):11-18.
Desai et al., "Microfabricated immunoisolating biocapsules," Biotechnol. Bioeng., Jan. 5, 1998, 57(1):118-120.
Desai et al., "Nanoporous anti-fouling silicon membranes for biosensor applications," Biosens. Bioelectron., 2000, 15:453-462.
Druker, 8. J., "Perspectives on the development of a molecularly targeted agent," Cancer Cell, Feb. 2002, 1:31-36.
Duncan R., "The dawning era of polymer therapeutics," Nat. Rev. Drug Discov., May 2003, 2:347-360.
Ferrari, M., "Cancer nanotechnology: opportunities and challenges," Na. Rev. Cancer, Mar. 2005, 5:161-171.
Ferrari, M., "Nanovector therapeutics," Curr. Opin. Chem. Biol., 2005, 9:343-346.
Foraker et al., "Microfabricated porous silicon particles enhance paracellular delivery of insulin across intestinal Caco-2 cell monolayers," Pharm. Res., Jan. 2003, 20(1):110-116.
Gardner, P., "Microfabricated nanochannel implantable drug delivery devices: trends, limitations and possibilities," Expert Opin Drug Deliv, 2006, 3:479-487.
Gilles et al., "Designing Macromolecules for Therapeutic Applications : Polyester Dendrimer-Poly(ethylene oxide) 'Bow-Tie' Hybrids with Tunable Molecular Weight and Architecture," J. Am. Chem. Soc, 2002, 124:14137-14146.
Gonzalez-Mariscal et al., "Topical Review: Critical Role of Tight Junctions in Drug Delivery across Epithelial and Endothelial Cell Layers," J. Membrane Biol., 2005, 207:55-68.
He et al., "Bioconjugated Nanoparticles for DNA Protection from Cleavage," J. Am. Chem. Soc., 2003, 125:7168-7169.
Hirsch et al., "Nanoshell-rnediated near-infrared thermal therapy of tumors under magnetic resonance guidance," Proc. Natl. Acad. Sci. USA, Nov. 11, 2003, 100(23):13549-13554.
Hobday et al., "Molecularly targeted therapies for breast cancer," Cancer Control, 2005, 12(2):73-81.
International Search Report and Written Opinion dated Jun. 13, 2008, in corresponding PCT/US2007/075516, 9 pages.
Ishii et al., "Chaperonin-mediated stabilization and ATP-triggered release of semiconductor nanoparticles," Nature, Jun. 5, 2003, 423:628-632.
Kerbel et al., "Antiangiogenic Therapy: A Universal Chemosensitization Strategy for Cancer?" Science, May 26, 2006, 312:1171-1175.
Kim et al. "Near-infrared fluorescent type II quantum dots for sentinel lymph node mapping," Nat. Biotechnol., Jan. 2004, 22(1):93-97.
Lan et al., "Surface modification of silicon and gold-patterned silicon surfaces for improved biocompatibility and cell patterning selectivity," Biosens. Bioelectron. 2005, 20:1697-708.
Landen et al., "Therapeutic EphA2 Gene Targeting In vivo Using Neutral Liposomal Small Interfering RNA Delivery," Cancer Res., Aug. 1, 2005, 65(15):6910-6918.
Langer, Robert, "Drug delivery and targeting," Nature, Apr. 30, 1998, 392(Supp):5-10.
Lasic, D. D., "Doxorubicin in sterically stabilized liposomes," Nature, Apr. 11, 1996, 380:561-562.
LaVan et al., "Small-scale systems for in vivo drug delivery," Nat. Biotechnol., Oct. 2003, 21 (10):1184-1191.
Li et al., "Doxorubicin physical state in solution and inside liposomes loaded via a pH gradient," Biochimica et Biophysica Acta, 1998, 1415:23-40.
Lin et al., "A porous silicon-based optical interferometric biosensor," Science, Oct. 31, 1997, 278:840-843.
Liu et al., "In vivo biodistribution and highly efficient tumour targeting of carbon nanotubes in mice," Nature Nanotechnology, Jan. 2007, 2:47-52.
Loo et al., "Nanoshell-Enabled Photonics-Based Imaging and Therapy of Cancer," Technol. Cancer Res. Treat., Feb. 2004, 3(1):33-40.
Low et al., "Evaluation of mammalian cell adhesion on surface-modified porous silicon." Biomaterials, 2006, 27(26): 4538-4546.
Mansur et al., "Biomaterial with chemically engineered surface for protein immobilization," J. Mater. Sci. Mater. Med., 2005, 16:333-340.
Mayne et al., "Biologically Interfaced Porous Silicon Devices." Physica Status Solidi, 2000, 182(1):505-513.
Meade et al., "Microfabrication of freestanding porous silicon particles containing spectral barcodes," phys. stat. sol. (RRL), 2007, 1(2):R71-R-73.
Meade et al., "Porous Silicon Photonic Crystals as Encoded Microcarriers," Advanced Materials, Oct. 18, 2004, 16(20), 1811-1814.
Moghimi et al., "Nanomedicine: current status and future prospects," Faseb J., Mar. 2005, 19:311-330.
Nakanishi et al., "Development of the polymer micelle carrier system for doxorubicin," J. Control. Release, 2001, 74:295-302.
Office Communication issued in Canadian Patent Application No. 2,664,919, dated Mar. 7, 2016.
Office Communication issued in U.S. Appl. No. 11/836,004, dated Dec. 30, 2014.
Office Communication issued in U.S. Appl. No. 11/836,004, dated Jan. 28, 2014.
Office Communication issued in U.S. Appl. No. 11/836,004, dated Jun. 19, 2013.
Office Communication issued in U.S. Appl. No. 11/836,004, dated Aug. 28, 2012.
Office Communication issued in U.S. Appl. No. 11/836,004, dated Mar. 30, 2011.
Office Communication issued in U.S. Appl. No. 11/836,004, dated Jul. 30, 2010.
Office Communication issued in U.S. Appl. No. 11/836,004, dated Mar. 8, 2010.
O'Neal et al., "Photo-thermal tumor ablation in mice using near infrared-absorbing nanoparticles," Cancer Lett., 2004, 209:171-176.
Oyewumi et al., "Engineering Tumor-Targeted Gadolinium Hexanedione Nanoparticles for Potential Application in Neutron Capture Therapy," Bioconjug. Chem., 2002, 13:1328-1335.
Prestidge et al., "Mesoporous silicon: a platform for the delivery of therapeutics," Expert Opin. Drug Deliv., 2007, 4(1):101-110.
Quintana et al., "Design and Function of a Dendrimer-Based Therapeutic Nanodevice Targeted to Tumor Cells Through the Folate Receptor," Pharm. Res., Sep. 2002, 19(9):1310-1316.
Raja et al., "Hybrid Virus-Polymer Matreials. 1. Synthesis and Properties of PEG-Decoraged Cowpea Mosaic Virus," Biomacromolecules, 2003, 4:472-476.

(56) References Cited

OTHER PUBLICATIONS

Saini et al., "Covalent sidewall functionalization of single wall carbon nanotubes," J. Am. Chem. Soc., 2003, 125:3617-3621.

Sakamoto et al., "Anti-Biological Barrier Nanovector Technology for Cancer Applications," Expert Opin. Drug Deliv., 2007, 4(4):359-369.

Salonen et al., "Mesoporous Silicon in Drug Delivery Applications," Journal of Pharmaceutical Sciences, Feb. 2008, 97(2):632-653.

Salonen et al., "Mesoporous silicon microparticles for oral drug delivery: Loading and release of five model drugs," Journal of Controlled Release, 2005, 108:362-374.

Schreiber, F., "Structure and growth of self-assembling monolayers," Progress in Surface Science, 2000, 65:151-256.

Shriver-Lake et al., "Antibody immobilization using heterobifunctional crosslinkers." Biosens. Bioelectron., 1997, 12(11):1101-1106.

So et al., "Self-illuminating quantum dot conjugates for in vivo imaging," Nat. Biotechnol., Mar. 2006, 24(3):339-343.

Soppimath et al., "Biodegradable polymeric nanoparticles as drug delivery devices," J. Control. Release, 2001, 70: 1-20.

Starodub et al., "Antibody immobilisation on the metal and silicon surfaces. The use of self-assembled layers and specific receptors," Bioelectrochemistry, 2005, 66: 111-115.

Sullivan et al., "Nanotechnology and tumor imaging: seizing an opportunity," Mol. Imaging, Oct. 2004, 3(4):364-369.

Tasciotti et al., "Mesoporous silicon particles as a multistage delivery system for imaging and therapeutic applications," Nature Nanotechnology, Mar. 2008, 3:151-158.

Thomas et al. "Delivery of nanogram payloads using magnetic porous silicon microcarriers," Lab Chip, 2006, 6:782-787.

Torchilin, V. P., "Multifunctional nanocarriers," Adv. Drug Deliv. Rev., 2006, 58:1532-1555.

Uziely et al., "Liposomal doxorubicin: antitumor activity and unique toxicities during two complementary phase I studies," J. Clin. Oncol., 1995, 13(7):1777-1785.

Wang et al., "Surface modification of micromachined silicon filters," Journal of Materials Science, 2000, 35:4923-4930.

Yan et al., "Synthesis and Characterization of Silica-Embedded Iron Oxide Nanoparticles for Magnetic Resonance Imaging," J. Nanosci. Nanotechnol., 2004, 4(1/2):72-76.

Yan et al., "The Embedding of Meta-tetra(Hydroxyphenyl)-Chlorin into Silica Nanparticle Platforms for Photodynamic therapy and Their Singlet Oxygen Production and pH-dependent Optical Properties," Photoch Photobiol., 2003, 78(6):587-591.

Yokokawa et al., "Mechanical properties of aerogel-like thin films used for MEMS," J. Micromech. Microeng., 2004, 14:681-686.

Zhang et al., "Proteins and cells on PEG immobilized silicon surfaces," Biomaterials, 1998, 19:953-60.

\* cited by examiner

FIG. 4A
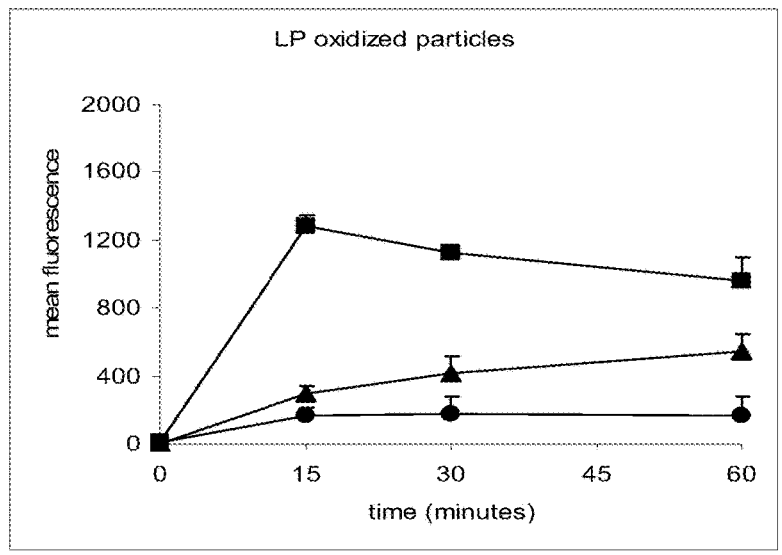
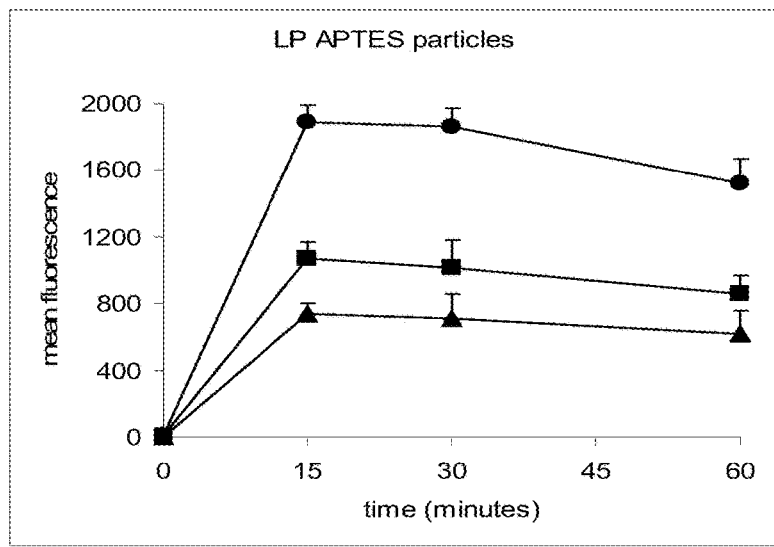
FIG. 4B

FIG. 4C
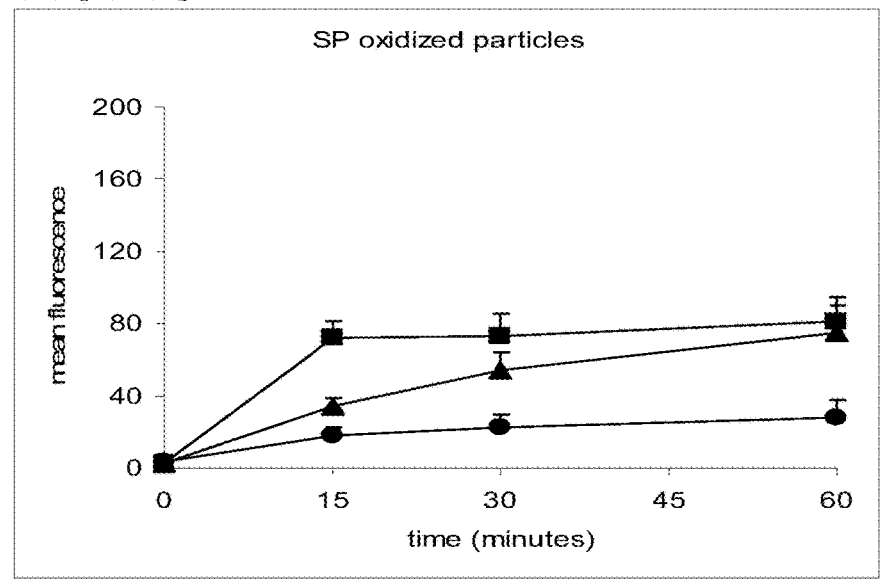
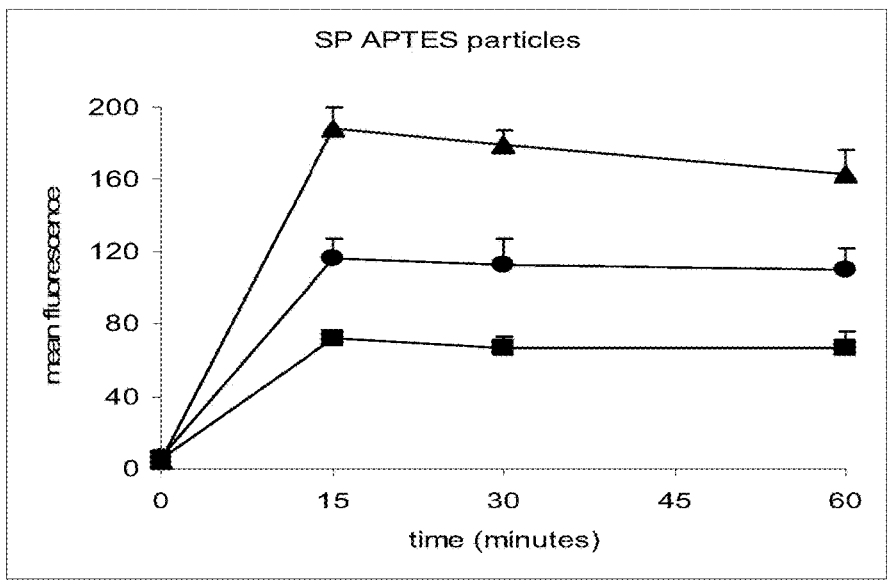
FIG. 4D

A *Confocal microscopy*

Neutral liposomes

Cationic liposomes

FIG. 10C
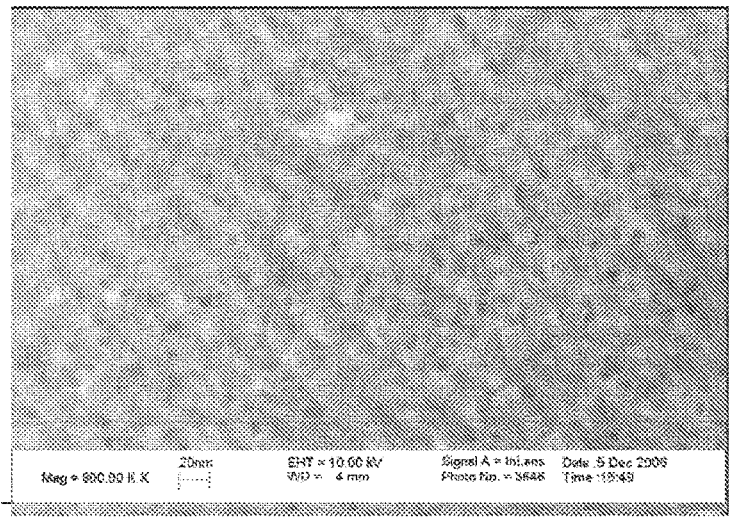
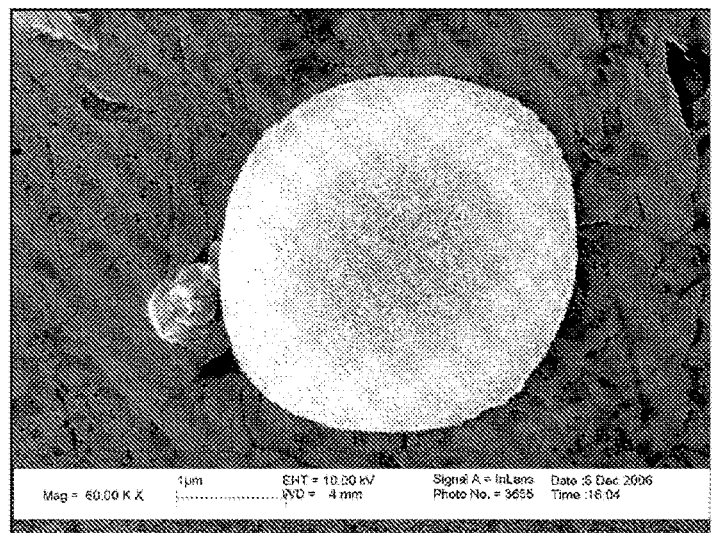
FIG. 10D

MULTISTAGE DELIVERY OF ACTIVE AGENTS

CROSS-REFERENCE TO RELATED APPLICATIONS

This application is a continuation of U.S. patent application Ser. No. 11/836,004, filed on Aug. 8, 2007, which claims the benefit 35 U.S.C. § 119(e) of U.S. Provisional Patent Application No. 60/821,750 filed Aug. 8, 2006, and U.S. Provisional Patent Application No. 60/914,348 filed Apr. 27, 2007, the disclosures of which are hereby incorporated herein by reference.

STATEMENT REGARDING FEDERALLY SPONSORED RESEARCH OR DEVELOPMENT

This invention was made with government support under Grant No. W81XWH-04-2-0035 Project 16 awarded by the U.S. Department of Defense and Grant No. SA23-06-017 awarded by NASA, and Grant No. NC1 1R21CA1222864-01 awarded by the National Institutes of Health. The government has certain rights in this invention.

BACKGROUND

Technical Field

The present inventions relate generally to the field of nanotechnology and, in particular, to compositions utilizing micro and/or nanoparticles for delivery active agents, such as therapeutic and imaging agents, and methods of making and methods of using such compositions.

Description of Related Art

The past quarter century's progress in the fundamental understanding of health and disease has not translated into comparable advances in clinical medicine. Inadequacies in the ability to administer therapeutic moieties so that they will selectively reach desired targets with marginal or no collateral damage has largely accounted for the discrepancy, see, e.g., Langer, R. Nature 392, 5-10 (1998); and Duncan, R. Nature Rev. Drug Discov. 2, 347-360 (2003).

Ideally, an active agent, such as a therapeutic or imaging agent, should travel through vasculature, reach the intended target at full concentration, then act selectively on diseased cells and tissues only, without creating undesired side effects. Unfortunately, even the best current therapies fail to attain this ideal behavior by a wide margin.

Nano-scale and micro-scale drug delivery systems, also known as 'nanovectors', are promising candidates for providing solutions to the problem of optimizing therapeutic index for a treatment, i.e. maximizing efficacy, while reducing health-adverse side effects. Even modest amounts of progress towards this goal have historically engendered substantial benefits across multiple fields of medicine, with the translatability from, for example, a subfield of oncology to a field as distant as the treatment of infectious disease being granted by the fact that the progresses had a single common denominator in the underlying technological platform. For example, liposomes, the first nanovector therapy to reach health-care fruition over 10 years ago for treatment of Kaposi's sarcoma, have also yielded advances in the treatment of breast and ovarian cancers, as well as fungal infections.

Today, many hundreds, if not thousands, of different nanovector technology platforms have joined liposomes, each with different properties, strengths, and weaknesses. Various nanovector platforms include polymer-based platforms, dendrimers, gold nano-shells, semiconductor nanocrystals, fullerenes, biologically derived nano-constructs, silicon- and silica-based nanosystems and superparamagnetic nanoparticulates are described in the literature.sup.49-75.

SUMMARY

In certain embodiments a composition is provided which comprises at least one first stage particle that is a micro or nanoparticle and that has (i) a body, (ii) at least one surface, and (iii) at least one reservoir inside the body, such that the reservoir contains at least one second stage particle that comprises at least one active agent.

In certain embodiments a method is provided which comprises administering to a subject a composition comprising: at least one first stage particle, that is a micro or nanoparticle and that has (i) a body, (ii) at least one surface and (iii) at least one reservoir inside the body, such that the reservoir contains at least one second stage particle that comprises at least one active agent.

In still another embodiment a method of making a multistage delivery system is provided which comprises (A) providing at least one first stage particle, that is a micro or nanoparticle and that has (i) a body, (ii) at least one surface (iii) at least one reservoir inside the body; (B) providing at least one second stage particle and (C) loading the at least one second stage particle inside the reservoir of the first stage particle. These and other embodiments, features and advantages will be apparent with reference to the following description and drawings

BRIEF DESCRIPTION OF THE DRAWINGS

FIG. 3, Panel B, demonstrates an effect of second stage PEG-FITC-SWNT nanoparticles concentration on their loading into nanoporous silicon first stage particles. In Panels A and B, Y-axis reads mean fluorescence.

FIGS. 4A-4D demonstrate time dynamics of second stage nanoparticles loading into nanoporous silicon first stage particles. 4A for "large pore" (LP) oxidized silicon first stage particles; 4B for LP APTES modified silicon first stage particles; 4C for "small pore" (SP) oxidized silicon first stage particle; 4D for SP APTES modifies silicon first stage particles. Y-axis reads mean fluorescence.

FIG. 6A, Panel B, demonstrates fluorescence quenching of Fluorescein Isothiocyanate (FITC) conjugated Single Wall Carbon Nanotubes (SWNT).

In FIG. 8A, Panels A-C show data for cationic and neutral liposomes loaded into 1 micron nanoporous silicon first stage particles. Panel A shows confocal microscopy images of neutral liposomes (left) and cationic liposomes (right). Panels B and C present respectively FACS analysis and Excel quantification of neutral and cationic liposome loading into 1 micron nanoporous silicon first stage particles. Y axis in Panel B reads particle number and Y axis in Panel C reads green fluorescence (logarithmic values). In FIG. 8B, Panel D shows time dynamics of loading liposomes containing Alexa 555 labeled SiRNA into 3.5 micron nanoporous oxidized silicon first stage particles. Y axis in Panel D reads mean fluorescence. Panel E and Panel F present fluorescent microscopy images visualizing fluorescence associated with liposomes containing Alexa 555 labeled SiRNA into 3.5 micron nanoporous silicon first stage particles.

FIGS. 10A-10D demonstrate Scanning Electron Microscopy (SEM) images of "small pore" (SP) nanoporous silicon first stage particles.

FIG. 12A, Panel A, for LP oxidized silicon particles; Panel B for SP oxidized silicon particles; FIG. 12B, Panel C, for LP APTES modified silicon particles. Panel D for SP APTES modified silicon particles. Y axis in FIGS. 12A-12B reads concentration of silicon (ng/mL).

FIGS. 16A-1-16C-3 present FACS 3D Profiles of HUVEC cells incubated with Nanoporous Silicon Particles and analyzed for their size and shape.

FIG. 22 presents confocal microscopy images demonstrating concentrated loading of Q-dots in a highly porous region of the back side of silicon particle. Panel a shows confocal microscopy images reconstructed in a series of 3 dimensional projections showing a single porous silicon particle rotated to display different vantage points. Panel b shows computer generated 3 dimensional models illustrating the rotation of the particle as shown in Panel a.

FIG. 23A, Panel A and Panel B respectively) and the shifts of the fluorescence signals after the incubation with PEG-FITC-SWNTs (+SWNTs), Q-dots (+Q-dots) and both (+Q-dots+SWNTs). Flow cytometry analysis show that PEG-FITC-SWNTs load rapidly and stabilize, while Q-dots gradually load before reaching a plateau, see FIG. 23B, Panel C. The release profiles of the Q-dots and PEG-FITC-SWNTs are both unaltered by the presence of another type of nanoparticle and are both sustained along time, FIG. 23 B, Panel D. Confocal microscopy images show the localization of the Q-dots (red) and PEG-FITC-SWNTs (green) in a single porous silicon particle. FIG. 23C, Panel E, Panel F and Panel G show bright field, green and red fluorescence respectively, while Panel h shows overlay of the 3 channels are shown. Yellow display showed co-localization of green and red fluorescent signals. Y axis in FIG. 23 B, Panel D, reads mean fluorescence; Y axis in Panel D reads released payload.

In FIG. 24, Panels a-d, the second stage particles are Q-dots; in Panels e-h, the second stage particles are PEG-FITC-SWNTs; in Panels j-m, the second stage particles are Q-dots and PEG-FITC-SWNTs. FIG. 24, Panels d, h and m are bright field images showing the details of particle morphology.

FIG. 26, Panel B, presents a graph showing relative amount of liposomes released from first stage nanoporous silicon particles. Y axis reads % of total amount of released liposomes. To test the release of nano-liposome from 1st stage carriers, the assembled multistage particles were incubated with 10% fetal bovine serum (pH 7.4) and release of nanoliposomes from 1st stage particles was followed along time using fluorimetry. Complete unloading was achieved in about 36 h.

DEFINITIONS

Figure 1:
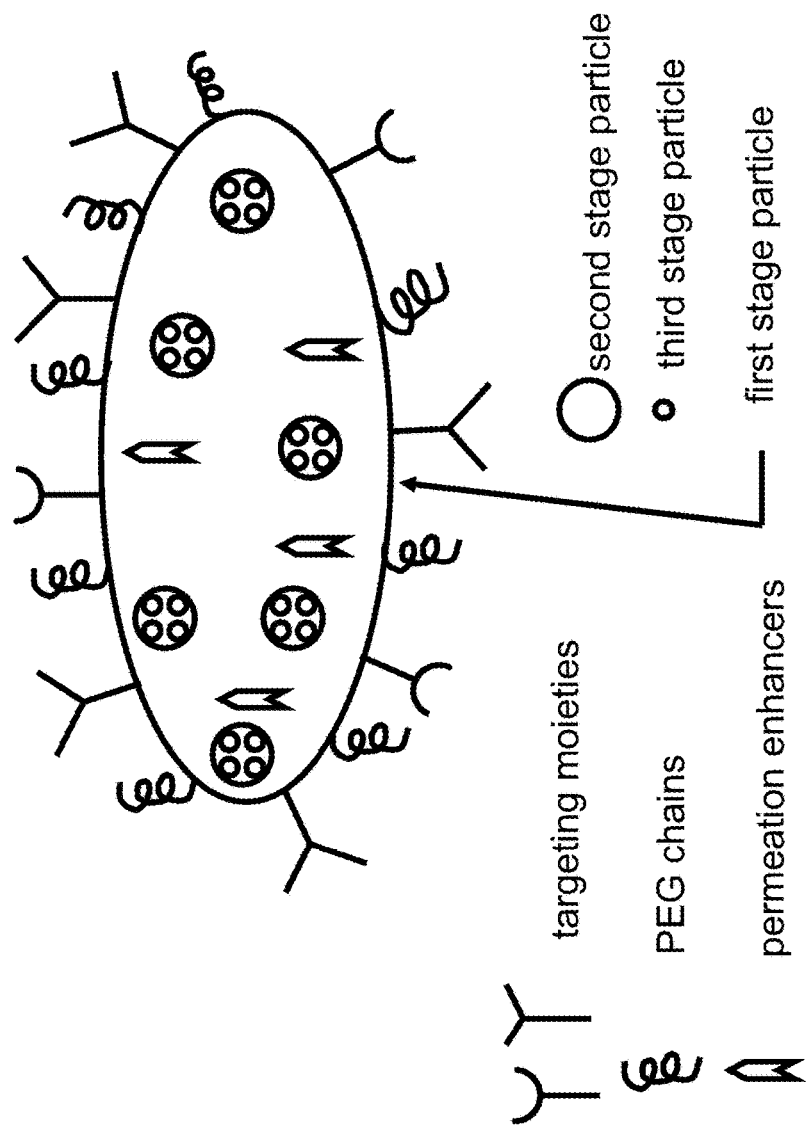
FIG. 1 illustrates a multistage delivery vehicle, in accordance with an embodiment of the invention. The first stage particle contains inside second stage particles. The second stage particles may comprise at least one active agent, such as a therapeutic agent or an imaging agent. The first stage particle also contains inside an additional agent, such as a permeation enhancer or an additional active agent, which may be an imaging agent or a therapeutic agent. Optionally, the second stage particles contain third stage particles. Targeting moieties, such as antibodies, aptamers or ligands, attached to the surface of the first stage particle, facilitate localization at the selected body site.

Unless otherwise specified "a" or "an" means one or more.

"Biochemical environment of the target body site" refers to one or more intrinsic physiological conditions at the target site, such as pH, salt conditions, temperature, or the presence of target specific moieties, effective to initiate and promote release of the particle content.

"Biodegradable" refers to a material that may dissolve or degrade in a physiological medium or a biocompatible polymeric material that may be degraded under physiological conditions by physiological enzymes and/or chemical conditions.

"Mucoadhesive" refers to the capability of the particle to adhere to the mucosal layer, which lines the entire surface in the small and large intestine. Adherence is mediated by ligands grafted to the surface of the particles, which bind to chemical receptors present in mucin or the surface of the intestinal epithelial cells.

"Targeting moiety" is any factor that may facilitate targeting of a specific site by a particle. For example, the targeting moiety may be a chemical targeting moiety, a physical targeting moiety, a geometrical targeting moiety or a combination thereof. The chemical targeting moiety may be a chemical group or molecule on a surface of the particle; the physical targeting moiety may be a specific physical property of the particle, such as a surface such or hydrophobicity; the geometrical targeting moiety includes a size and a shape of the particle.

"Microparticle" means a particle having a maximum characteristic size from 1 micron to 1000 microns, or from 1 micron to 100 microns. "Nanoparticle" means a particle having a maximum characteristic size of less than 1 micron.

"Biocompatible" refers to a material that, when exposed to living cells, will support an appropriate cellular activity of the cells without causing an undesirable effect in the cells such as a change in a living cycle of the cells; a change in a proliferation rate of the cells and a cytotoxic effect.

DETAILED DESCRIPTION

In embodiments of the invention, a composition that includes two or more stages of particles, such that particles of a later stage (smaller size particles) are contained in particles of an earlier stage (larger particles), will potentially provide one or more advantages for treating, preventing and/or imaging a physiological condition, such as a disease, in a subject, which may be any animal with a blood system (e.g., the subject may be a warm blooded animal, such as mammal including human being). Embodiments of such multistage composition provide one or more of the following features or advantages: (1) an active agent, such as a therapeutic agent or an imaging agent, is preferentially delivered and/or localized to a particular target site in a body of a subject. Preferential delivery and/or localization means that an amount or concentration of the active agent delivered to and/or localized at the target site is higher than an amount or concentration of the active agent delivered to and/or localized at other sites in the body of the subject; (2) a multistage composition sequentially overcomes multiple biological barriers in a body of the subject; and (3) a multistage composition allows for simultaneous delivery and localization at the same or different target site of multiple active agents.

Biological Barriers

Following administration, an active agent, such as a therapeutic or imaging agent, formulated conventionally or in a nanovector, encounters a multiplicity of biological barriers that adversely impact the agent's ability to reach an intended target at a desired concentration. The biological barrier may be, for example, an epithelial or endothelial barrier, such as a blood-brain barrier or intestinal lumen endothelium, that are based on tight junctions, that prevent or limit para-cellular transport of an active agent. Each of the endo/epithelial barrier includes a plurality of sequential subbarriers, such as tight junction barriers, that owe their molecular discrimination to one or more zonula occluden proteins, and one or more additional biological membranes, such as vascular endothelial basement membrane or a musocal layer of the intestinal endothelium. Cells of the reticuloendothelial system may also act as a biological barrier against an active agent encapsulated inside nanoparticles, as such cells sequester/uptake the nanoparticles. The biological barrier may be also represented by a cell membrane or a nuclear membrane in a cell that an active agent has to come through.

Multistage Delivery Vehicle

Since the biological barriers are sequential, overcoming or bypassing such barriers has to be sequential too. Accordingly, a delivery vehicle has been developed that, in embodiments, acts in multiple stages. Each stage of the vehicle is defined by a particle having a separate intended function, which may be different from an intended function of a particle of another stage. For example, a particle of one stage is designed to target a specific body site, which may be different from a site targeted by a particle of another stage, and thus to overcome or bypass a specific biological barrier, which is different from a biological barrier being overcome or bypassed by a particle of another stage. A particle of each subsequent stage is contained inside a particle of an immediately preceding stage. A particle of any particular stage may contain an active agent, such as a therapeutic agent or an imaging agent, intended for use at this particular stage.

In a preferred embodiment, a particle of the last stage is an active agent formulated as a nanoparticle or alternatively the last stage particle contains the active agent inside, while a particle of any earlier stage per se may or may not comprise an active agent. In some embodiments, in addition to targeting a specific body site, a particle of each stage is designed in such a way that it is capable to perform targeted release of its content. In embodiments, the number and type of stages in the multistage delivery vehicle depends on several parameters, including administration route and an intended final target for the active agent. An embodiment of a multistage delivery vehicle is illustrated on FIG. 1.

First Stage Particle

In some embodiments, the particle of the first stage is a micro or nanoparticle. In some embodiments, the first stage particle has a characteristic size of at least 500 microns or at least 1 mm. Such a particle may be configured to contain inside at least one micro or nanoparticle, which in turn may contain inside at least one particle of a smaller size. The first stage particle is any particle that is capable of containing inside particles of a smaller size.

In some embodiments, the first stage particle is a top-down fabricated particle, i.e., a particle prepared by top-down microfabrication or nanofabrication methods, such as photolithography, electron beam lithography, X-ray lithography, deep UV lithography or nanoprint lithography. A potential advantage of using the top-down fabrication methods is that such methods provide for a scaled up production of particles that are uniform in dimensions.

The particle of the first stage may be configured to overcome at least one of the following biological barriers: a hemo-rheology barrier, a Reticulo-Endothelial System barrier, an endothelial barrier, a blood brain barrier, a tumor-associated osmotic interstitial pressure barrier, an ionic and molecular pump barrier, a cell membrane barrier, an enzymatic degradation barrier, a nuclear membrane barrier or a combination thereof.

The first stage particle may have a body that is defined by a size and a shape of the particle and one or more reservoirs inside the body. One or more second stage particles may be contained inside the reservoir.

The body of the first stage particle comprises any appropriate material. Preferably, the material of the body of the first stage particle is biocompatible. In some embodiments, the body of the first stage particle comprises an oxide material such as silicon oxide, aluminum oxide, titanium oxide, or iron oxide; a semiconductor material, such as silicon; a polymer or a polymer oxide material; or a ceramic material. In some embodiments, the body of the first stage particle comprises a biodegradable material, such as, for example, nanoporous silicon. The biodegradable material may be such that it degrades when exposed to a physiological medium such as silicic acid.

In some embodiments, a material of the body of the first stage particle is substantially the same in different regions of the body. The shape of the first stage particle may depend on the administration route. For example, the shape may be configured to maximize the contact between the first stage particle and a surface of the target site, such as endothelium surface for intravascular administration or intestinal epithelium for oral administration. Accordingly, for oral and intravascular administration, the first stage particle may have a selected non-spherical shape configured to maximize the contact between the particle and endothelium surface. Examples of appropriate shapes include, but are not limited to, an oblate spheroid or a disc. For pulmonary administration, i.e., administration to lungs of the subject, the first stage particles may also have a selected non-spherical shape configured to maximize a contact between the particle and one of the epithelial tissues in lungs.

For pulmonary administration, i.e., an administration route, which involves passing of the particle through lungs of a subject, the first stage particle may also have a spicular shape, which may facilitate entering of the particle from the lungs into a body tissue, not necessarily through the blood circulation.

Although top-down fabrication allows manufacturing particles having size in a wide range from 50 nm up to several millimeters, for certain administration routes particular particle sizes may be preferred. For example, for intravascular administration, a maximum characteristic size of the particle, e.g., a diameter for a disc-shaped particle, is preferably sufficiently smaller than a radius of the smallest capillary. In humans, such a radius is about 4 or 5 microns. Accordingly, the maximum characteristic size of the particle are, in some embodiments, less than about 3 microns, less than about 2 microns or less than about 1 micron.

In embodiments, the maximum characteristic size of the first stage particle is from 500 nm to 3 microns, or from 700 nm to 2 microns. Yet in some embodiments for intravascular administration in oncological applications, the maximum characteristic size of the first stage particle is such that the first stage particle could localize at the targeted vasculature site without penetrating a fenestration in vascular cancer endothelium. For such applications, the maximum characteristic size of the first stage particle is greater than about 100 nm, or greater than about 150 nm, or greater than about 200 nm.

Yet in some embodiments for intravascular administration, the size of the first stage particle is such so that the particle may penetrate the fenestration. Accordingly, the maximum characteristic size in such applications is preferably less than about 200 nm, or less than about 150 nm, or less than about 200 nm. In some embodiments, one may select a size of the first stage particle that is selected to be a critical radius of normal non-fenestrated vasculature for targeting fenestrated vasculature as detailed in PCT patent application No. PCT/US2006/038916 "Methods and Compositions for Targeting Fenestrated Vasculature" filed Sep. 27, 2006 to Paolo Decuzzi and Mauro Ferrari.

For oral administration, it may be preferable to use the first stage particle that has a maximum characteristic size greater than about 2 microns or greater than about 5 microns or greater than about 10 microns. One advantage of using the first stage particle of such size for oral administration is that such particle may be too large to be endocytosed by intestinal epithelial cells. The endocytosis by intestinal epithelial cells has at least two potential disadvantages: 1) the content of the first stage particle may be deactivated as it is processed by the endothelial cell before it reaches the desired target; 2) the potential toxicity of particular carrier, e.g. of the material of the particle, is of greater concern if it is endocytosed than if it is cleared through the gastrointestinal tract.

In some embodiments, for oral administration, the first stage particle has a size ranging from 500 microns to several centimeters, or from 1 mm to 2 cm.

For pulmonary administration, the maximum characteristic size of the first stage particle is preferably less than about 20 microns but greater than about 5 microns, if a targeted site is located in the lungs' air passages. For targeting a site in alveoli, the maximum characteristic site may be less than about 5 microns.

In some embodiments, for subcutaneous administration, a characteristic size of the first stage particle is from 50 microns to 1 mm; or from 100 microns to 1 mm.

One of the functions of the first stage particle, in embodiments, is localization at a particular target site. For intravascular administration, such target site may be a particular vasculature site. For example, in anticancer applications, the targeted vasculature site may be a tumor vasculature, such as angiogenesis vasculature, coopted vasculature or renormalized vasculature. The localization of the first stage particle at the targeted site may be facilitated by geometrical factors, such as the size and the shape of the particle.

For intravascular administration, the localization at the targeted site may be also facilitated by one or more recognition factors on the surface of the first stage particle. The recognition factor may be a chemical targeting moiety, such as a dendrimer, an antibody, an aptamer, which may be a thioaptamer, a ligand or a biomolecule that binds a particular receptor on the targeted site. For oral delivery, the chemical moiety may comprise one or more mucoadhesive ligands, as described in Table 1 of U.S. Pat. No. 6,355,270.

The selectivity of the targeting may be tuned by changing chemical moieties of the surface of the particles. For example, coopted vasculature is specifically targetted using antibodies to angiopoietin 2; angiogenic vasculature is recognized using antibodies to vascular endothelial growth factor (VEGF), basic fibroblast growth factor (FGFb) or endothelial markers such as $\alpha v \beta 3$ integrins, while renormalized vasculature are recognized using carcinoembionic antigen-related yell adhesion molecule 1 (CEACAM1), endothelin-B receptor (ET-B), vascular endothelial growth factor inhibitors gravin/AKAP12, a scallofldoing protein for protein kinase A and protein kinase C, see, e.g., Robert S. Korbel "Antiangiogenic Therapy: A Universal Chemosensitization Strategy for Cancer?", Science 26 May 2006, vol 312, no. 5777, 1171-1175.

For targeting to non-circulating vasculature cells, the binding between the first stage particle and the molecular marker of the targeted vasculature site should be sufficiently strong to overcome the drag force exerted by the flowing blood. This objective may be satisfied by having a relatively large planar surface area for specific binding and a relatively low profile in a capillary's blood flow space, i.e., by having the particle of the selected non-spherical shape, such as an oblate spheroid or a disc.

The recognition factor may be also a physical recognition moiety, such as a surface charge. The charge may be introduced during the fabrication of the particle by using a chemical treatment such as a specific wash. For example, immersion of porous silica or oxidized silicon surface into water may lead to an acquisition of a negative charge on the surface, see, e.g., Behrens and Grier, J. Chem. Phys. 115 (14), (2001). P. 6716-6761. The surface charge may be also provided by an additional layer or by chemical chains, such as polymer chains, on the surface of the particle. For example, polyethylene glycol chains may be a source of a negative charge on the surface. Polyethylene glycol chains may be coated or covalently coupled to the surface as described in P. K. Jal, S. Patel, B. K. Mishra, Talanta 62 (2004) P1005-1028; S.W. Metzger and M. Natesan, J. Vac. Sci. Technol. A 17(5), (1999) P 2623-2628; and M. Zhang, T. A. Desai and M. Ferrari, Biomaterials, 19, (1998), p 953. The positive charge is introduced, for example, by coating the surface with a basic polymer, such as polylysine or by covalently linking to the surface an amino containing molecule, such as 3-aminopropyltriethoxysilane.

In some embodiments, modeling methods are applied for selecting geometrical factors, such as a size and a shape, and/or surface modification, such as chemical modification and electrostatic modification, of the particle based on one or more properties of the selected target site. Such modeling methods are disclosed, for example, in 1) U.S. Provisional Patent Application No. 60/829,075 "Particles for Cell Targeting" filed Oct. 11, 2006 to Paolo Decuzzi and Mauro Ferrari; 2) U.S. Provisional Patent Application No. 60/891,584 "Endocytotic particle" filed Feb. 26, 2007 to Paolo Decuzzi and Mauro Ferrari; 3) Decuzzi, P., Causa, F., Ferrari, M. & Netti, P. A. The effective dispersion of nanovectors within the tumor microvasculature Ann Biomed Eng 34, 633-41 (2006); 4) Decuzzi, P. & Ferrari, M. The adhesive strength of non-spherical particles mediated by specific interactions. Biomaterials 27, 5307-14 (2006); 5) Decuzzi, P. & Ferrari, M. The role of specific and non-specific interactions in receptor-mediated endocytosis of nanoparticles. Biomaterials 28, 2915-22 (2007); 6) Decuzzi, P., Lee, S., Bhushan, B. & Ferrari, M. A theoretical model for the margination of particles within blood vessels. Ann Biomed Eng 33, 179-90 (2005); Decuzzi, P., Lee, S., Decuzzi, M. & Ferrari, M. Adhesion of microfabricated particles on vascular endothelium: a parametric analysis. Ann Biomed Eng 32, 793-802 (2004).

In some embodiments, the first stage particle is configured to release the second stage particles from its reservoir at the target site. The release of the second stage particles may be performed according to a variety of mechanisms, including, but not limited to, diffusion of the second stage particles through the channels connecting the reservoir and the surface of the first stage particle and degradation or erosion of the body the first stage particle. For such a purpose, the first stage particle is configured to have a characteristic release time longer than a characteristic delivery time of the first stage particle to its target site when administered to the subject.

In some embodiments, the first stage particle is configured to perform a release of the second stage particles from its reservoir that is sustained over a period of time longer than a characteristic delivery time of the first stage particle to its target site when administered to the subject. In some embodiments, the first stage particle is configured to release the second stage particles over a time period longer than at least 0.5 hr; or longer than at least 1 hr; or longer than at least 2 hr; or longer than at least 8 hr; or longer than at least 15 hr; or longer than 30 hr.

In some embodiments, physical localization and/or targeted release of the first stage particle is initiated by one or more intrinsic physiological conditions at the target site such as pH, salt concentrations or temperature. In some embodiments, physical localization and/or targeted release of the first stage particle is initiated by exogeneous stimulation. Examples of exogeneous stimulations include mechanical activation, such activation by ultrasound; electromagnetic activation, such an activation by visible, ultraviolet, near-infrared or infrared light, radiofrequency or X-ray radiation; magnetic radiation. For example, the first stage particle may comprise a smart polymer, i.e., a polymer that contracts or expand in a response to a specific stimulus, such as light, temperature or pH. Smart polymers are described, for example, in "In Situ Activation of Microencapsulated Drugs (MSC-22866)," NASA Tech Briefs, Vol. 24, No. 9 (September 2000), page 64; "Externally Triggered Microcapsules Release Drugs In Situ (MSC-22939), NASA Tech Briefs, (April 2002), page 50; and U.S. Pat. No. 6,099,864 issued to Morrison and Mosier on Aug. 8, 2000. In some cases, more than one exogeneous stimulation is used together for activating release.

To increase the localization/targeting efficiency, the first stage particle may utilize multiple, i.e., more than one recognition/localization/targeting factors, which preferably do not interfere with each other. For example, the first particle may have the selected non-spherical shape as discussed above and at the same time carry tumor-targeting antibodies on its surface.

In some embodiments, the surface of the first stage particle may be coated with polymer chains partially or completely. The polymer chains may be added after the fabrication of the intravascular stage particle. The polymer chains may be hydrophilic chains, such as polyethylene glycol (PEG) chains or synthetic glycocalix chains, which may be used for overcoming the uptake of the particle by cell of the reticulo-endothelial system and, thus, extending the blood circulation of the intravascular stage particle. The hydrophilic groups may also serve for enhancement of solubility of the multistage delivery devices.

A variety of materials may be derivatized with polymer chains. For example, when the particle's surface material comprises a polymer, polymer chains may be attached by linking carboxylic groups of the polymer and amine or hydroxyl groups in the polymer chains; if the particle's surface material comprises metal such as gold, the polymer chains may be attached to the surface via thiol chemistry; when the particle's surface material comprises an oxide, such silicon oxide, titanium oxide or aluminum oxide, the polymer chains may be attached using silane chemistry.

In addition to one or more second stage particles, the reservoir of the first stage particle may contain one or more additional agents. Such additional agent may include an additional active agent, such as a therapeutic agent or an imaging agent, a targeting agent, one or more penetration enhancers or any combination thereof. The penetration enhancer may include one or more compounds listed in Table 1.

TABLE 1

Penetration Enhancers

| Class of Enhancer | Specific Examples |
|---|---|
| Bile Salts | Glyo-deoxycholate |
| | Taruro-dexoycholate |
| | Tauro-chenodeoxycholate |
| | Glyco-chenodexycholate |
| | Taurocholate |
| | Glycocholate |
| | Glycoursocholate |
| | Tauroursocholate |
| | Dexoycholate |
| | Chenodeoxycholate |
| | Cholate |
| | Ursocholate |
| Non-ionic Surfactants | Polyoxyethylene (POE) ethers (e.g., Brij, Texaphor) |
| | Alkylphenoxy-POEs (Triton, Igepal, Surfonic) |
| Anionic Surfactants | sodium dodecyl sulfate |
| | dioctyl sodium sulfosuccinate |
| Lecithins | Lysolecithin |
| Medium chain glycerides | mono-, di-, or triglycerides of C8, C10, or C12 fatty acids |
| Medium chain fatty acids | sodium caprylate |
| | sodium caprate |
| | sodium laurate |

TABLE 1-continued

Penetration Enhancers

| Class of Enhancer | Specific Examples |
|---|---|
| Salicylates | sodium salicylate |
| Acylcarnitines | decylcarnitine |
| | laurylcarnitine |
| | myristoylcarnitine |
| Acylcholines | Laurylcholine |
| | Palmitoylcholine |
| Acyl amino acids | N-laurylphenylglycine |
| | N-palmitoylglycine |
| Calcium chelators | Ethylenediaminetetraacetic acid (EDTA) |
| Peptides | PZ-peptide |
| | Zonula occludens toxin (ZOT) |

For intravascular administration, the penetration enhancers may include a basement membrane penetration enhancer that may act against the basement membrane, and/or one or more penetration enhancers, that may act against tight junction proteins (TJPs). An example of the basement membrane penetration enhancer is metalloproteinase, such as Collagenase IV, MMP-2, and MMP-9. An example of the anti-TJP penetration enhancer is zonula occluden toxin. Anti-TJP penetration enhancers and strategies for modulating tight junction permeability are detailed, for example, in Gonzalez-Mariscal, L., Nava, P. and Hernandez, S. J. Membr. Biol., 2005. 207(2): p. 55-68.

Figure 2A:
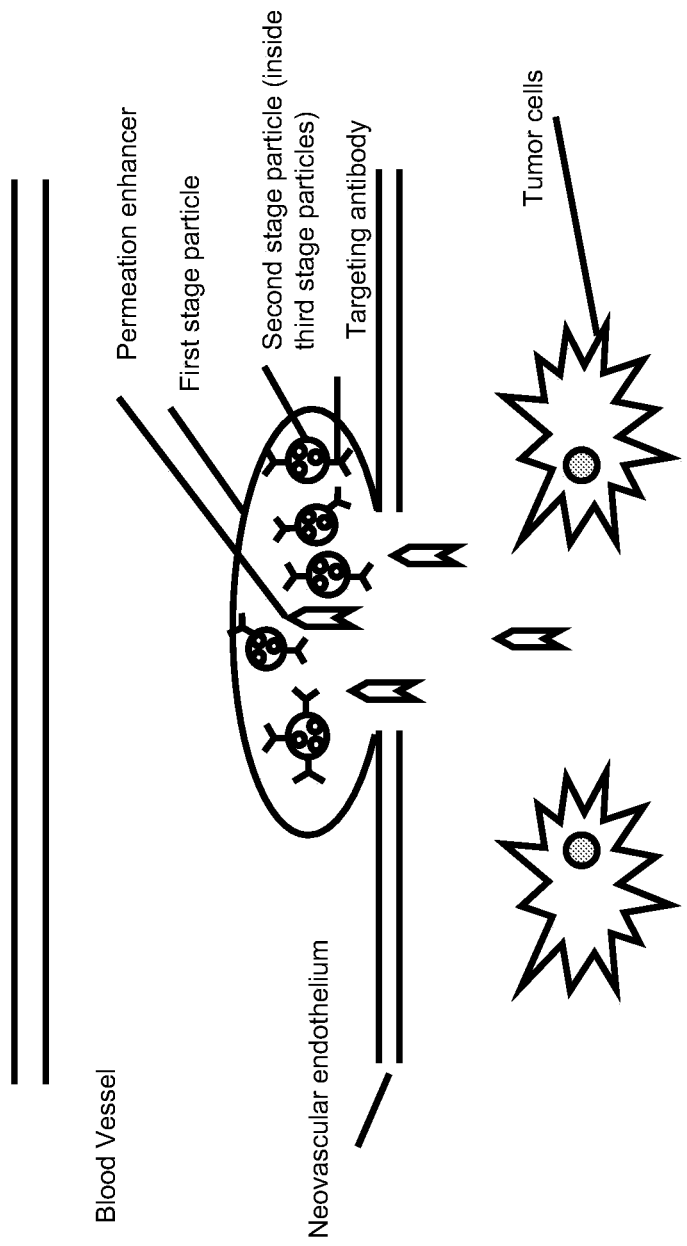
FIGS. 2A-2B illustrate the principle of operation of a multistage delivery vehicle administered intravascularly, in accordance with an embodiment. The first stage particle localizes at the targeted vasculature location. Upon the localization, the particle releases permeation enhancers that generate a fenestration in the vasculature. Second stage particles carry targeting moieties, such as antibodies. The second stage particles may permeate through the fenestration and target specific cells that carry surface marker antigens, using the antibodies.
Figure 2B:
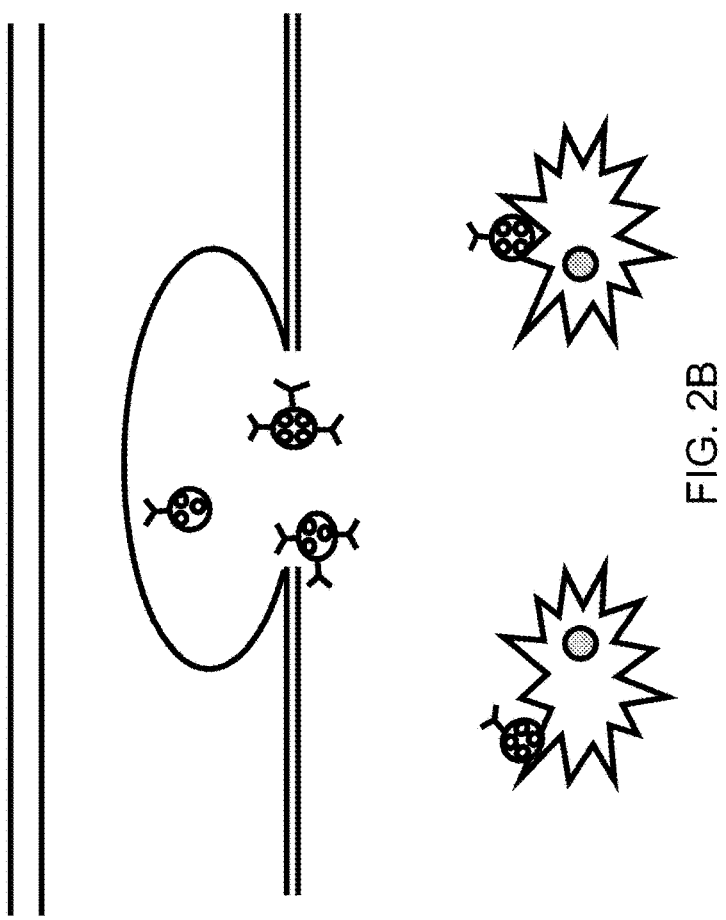

FIGS. 2A-B illustrate the action of penetration enhancer upon localization of the first stage particle at the targeted vasculature site, in accordance with an embodiment. The first stage particle releases the permeation enhancers that generate in the targeted vasculature one or more fenestrations, through which the second stage particles penetrate into the vasculature.

In some embodiments, the first stage particle has one or more channels fluidically connecting the reservoir with the surface, that may be in contact with endo or epithelial cells. For intravascular administration, such first stage particle may be a micro or nano fabricated particle, such as those detailed in U.S. Patent Application Publication No 2003/0114366 and U.S. Pat. No. 6,107,102, and for oral administration, such first stage particle may be a micro or fabricated particle, such as the ones disclosed in U.S. Pat. No. 6,355,270.

In some embodiments, the reservoir and the channels are pores in the body of first stage particle. In such case, the first stage particle may comprise a porous or nanoporous material. Preferably, the pores of the porous or nanoporous material may be controlled to achieve a desired load of the next stage particles and a desired release rate. The nanoporous material with controllable pore size may be an oxide material, such as silicon oxide, aluminum oxide, titanium oxide, or iron oxide. Fabrication of nanoporous oxide particles, also known as sol gel particles, is detailed, for example, in Paik J. A. et. al. J. Mater. Res., Vol. 17, August 2002. The nanoporous material with controllable pore size may be also nanoporous silicon. For details of fabrication of nanoporous silicon particles, see Cohen M. H. et. al. Biomedical Microdevices 5:3, 253-259, 2003. Control of pore density, size, shape and/or orientation may be accomplished by changing electrical current and etching time during formation of nanoporous silicon from non-porous silicon. Control of pore density, size, shape and/or orientation may be also accomplished by varying doping in non-porous silicon used for formation of nanoporous silicon. Thus, pore size, density, size, shape and /or orientation of nanoporous may be configured for efficient loading of the second stage particles.

In some embodiments, pore size in nanoporous first stage particles may be, for example, from about 1 nm to about 200 nm; or from about 2 nm to about 100 nm. In some cases, pore size in nanoporous first stage particle may be from about 3 to about 10 nm or from about 5 to about 7 nm. Yet in some cases, pore size in nanoporous first stage particle may be from about 10 to about 60 nm, or from about 20 to about 40 nm.

In some embodiments, to facilitate loading of the second stage particles into pores of the porous or nanoporous material may be modified chemically and/or electrostatically to make it compatible with chemical and/or electrostatical surface properties of the second stage particles. For example, for loading negatively charged second stage particles, it may be preferable to use positively charged pore surface. The positive charge may be achieved, for example, by depositing on pore surface an amino-containing molecule, such as 3-aminopropyltriethoxysilane. For loading positively charged second stage particles, it may be preferable to use negatively charged pore surface. The negative pore surface charge may be accomplished, for example, by oxidizing pore surface with water.

In some embodiments, the first stage particle has no channels at all. Such particle may comprise, for example, a biodegradable material. For oral administration, the material may be designed to erode in the GI tract. As examples, the first stage particle may be formed of metals, such as iron, titanium, gold, silver, platinum, copper, and alloys and oxides thereof. The biodegradable material may be also a biodegradable polymer, such as polyorthoesters, polyanhydrides, polyamides, polyalkylcyanoacrylates, polyphosphazenes, and polyesters. Exemplary biodegradable polymers are described, for example, in U.S. Pat. Nos. 4,933,185, 4,888,176, and 5,010,167. Specific examples of such biodegradable polymer materials include poly(lactic acid), polyglycolic acid, polycaprolactone, polyhydroxybutyrate, poly(N-palmitoyl-trans-4-hydroxy-L-proline ester) and poly(DTH carbonate).

In some embodiments, the body of the first stage particle includes two or more regions configured to contain different populations of second stage particles. For example, the body of the first stage particle may have a first region configured to contain a first population of second stage particles and a second region configured to contain a second population of second stage particles. For instance, the first stage particle formed of porous nanoporous material may be such that its body has two or more porous regions that differ from each other. The body of the nanoporous first stage particle may include a first porous region and second porous region that differ from each other in at least one property such as a pore density, pore geometry; pore charge, pore surface chemistry, pore orientation or any combination thereof. Such first and second regions may be configured respectively to contain a first and a second population of second stage particles.

In some embodiments, the first and second populations of second stage particles differ in at least one property such as size; shape; surface chemical modification; surface charge or a combination thereof.

In some embodiments, the first and second populations of second stage particles contain the same active agent. Yet, in some embodiments, the first and second population of second stage particles contain respectively a first active agent and a second active agent that are different from each other.

The first and second populations of second stage particles may be configured to perform different functions. For example, in some embodiments, the first and second populations may be configured to target respectively a first and second target sites that are different from each other.

In some embodiments, the first population are configured to target a particular site in a body of the subject, while the second population is configured to free circulate in the blood system of the subject.

In some embodiments, the first and the second population target the same target site in a body of the subject but perform a different function at the body site. For example, the first population contains a therapeutic agent to be delivered to the target site, while the second population contains an imaging agent to be delivered to the target site for imaging or visualizing the target site.

The first and the second regions of the body of the first stage particle may be such that at least one of them is a biodegradable region. Preferably, both the first and the second regions of the body of the first stage particle is biodegradable.

The first and the second regions of the body of the first stage particle may have different characteristic time for releasing the first and the second population of second stage particles. In some embodiments, both characteristic time for releasing the first population of second stage particles from the first region and characteristic time for releasing the second population of second stage particles from the second region may be greater that a characteristic for delivery and/or localization of the first stage particle at its target site when administered to the subject.

In some embodiments, the first stage particle is configured to separate into a first component that includes the first region and a second component that includes the second region when being exposed to a physiological medium, such as a medium that may be present at a target site of the first stage particle. Such exposure may occur, for example, when the particle is administered to the subject.

In some embodiments, the first and the second regions of the body of the first stage particle are configured to perform a different function when the particle is administered to the subject. For example, the first and the second region of the body of the first stage particle may be configured to overcome respectively the first and the second biological barriers that are different from each other. Such biological barriers may be each selected, for example, from a hemo-rheology barrier, a Reticulo-Endothelial System barrier, an endothelial barrier, a blood brain barrier, a tumor-associated osmotic interstitial pressure barrier, an ionic and molecular pump barrier, a cell membrane barrier, an enzymatic degradation barrier, a nuclear membrane barrier or a combination thereof.

Second Stage Particle

The second stage particle may be any micro or nanoparticle that may fit inside the reservoir of the first stage particle. For example, in certain embodiments, for oral or pulmonary administration, the second stage particle is the same as the first stage particle for intravascular administration.

The particle of the second stage may be configured to overcome at least one barrier selected from a hemo-rheology barrier, a Reticulo-Endothelial System barrier, an endothelial barrier, a blood brain barrier, a tumor-associated osmotic interstitial pressure barrier, an ionic and molecular pump barrier, a cell membrane barrier, an enzymatic degradation barrier, a nuclear membrane barrier or a combination thereof.

The composition, size and shape of the second stage particle are not particularly limited. For example, for many administration routes, the second stage particle may be a lipid based particle, such as a liposome, a micelle or lipid encapsulated perfluorocarbon emulsion; an ethosome; a carbon nanotube, such as single wall carbon nanotube; a fullerene nanoparticle; a metal nanoparticle, such gold nanoshell or triangular silver nanoparticle; a semiconductor nanoparticle, such as quantum dot or boron doped silicon nanowire; a polymer nanoparticle, such as particles made of biodegradable polymers and ion doped polyacrylamide particles; an oxide nanoparticle, such as iron oxide particle, a polymer coated iron oxide nanoparticle or a silicon oxide particle; a viral particle, such as an engineered viral particle or an engineered virus-polymer particle; a polyionic particle, such as leashed polycations; a ceramic particle, such as silica based ceramic nanoparticles, or a combination thereof.

In some embodiments, the second stage particle is configured to target a particular target site in a body of the subject. Such target site may be the same or different from the target site targeted by the first stage particle.

For example, the surface of the second stage particle may have one or more antibodies that may conjugate with surface marker antigens of certain types of cells. Thus, the second stage particle may selectively target cells that carry such marker antigens. The examples of cells that carry surface marker antigens include stem or clonogenic cells and tumor cells. The surface marker antigens on stem or clonogenic cells may be targeted by CD33 antibody. A number of monoclonal antibodies to tumor specific antigens are available, see, e.g., pp. 301-323 of CANCER, 3rd Ed., De Vita, et. al. eds; Janeway et. al. Immunology 5th Edition, Garland Press, New York, 2001; A. N. Nagappa, D. Mukherjee & K. Anusha "Therapeutic Monoclonal Antibodies", PharmaBiz. com, Wednesday, Sep. 22, 2004. Table 2 presents FDA approved monoclonal antibodies for treatment of cancer.

TABLE 2

| MAb Name | Trade Name | Used to Treat: | Approved in |
|---|---|---|---|
| Rituximab | Rituxan | Non-Hodgkin lymphoma | 1997 |
| Trastuzumab | Herceptin | Breast cancer | 1998 |
| Gemtuzumab ozogamicin* | Mylotarg | Acute myelogenous leukemia (AML) | 2000 |
| Alemtuzumab | Campath | Chronic lymphocytic leukemia (CLL) | 2001 |
| Ibritumomab tiuxetan* | Zevalin | Non-Hodgkin lymphoma | 2002 |
| Tositumomab* | Bexxar | Non-Hodgkin lymphoma | 2003 |
| Cetuximab | Erbitux | Colorectal cancer | 2004 |
|  |  | Head & neck cancers | 2006 |
| Bevacizumab | Avastin | Colorectal cancer | 2004 |

In some embodiments, the second stage particle is configured to freely circulate in a blood system of the subject upon being released from the first stage particle. In some cases, such second stage particle may have a surface free of targeting moieties, such as antibodies. The free circulating second stage particle may be used, for example, as to report of therapeutic action a therapeutic agent associated with a first stage particle per se.

In some embodiments, the surface of the second stage particle does not have hydrophilic polymer chains, such as polyethylene glycol (PEG) disposed on it. In certain cases, this may be an advantage of the multistage delivery vehicle as PEG chains are usually attached to liposomes and other nanoparticles to delay recognition and sequestration by macrophages of the reticulo-endothelial system. Unfortunately, the PEG chains may also hide antibodies on the nanoparticles surfaces and thus inhibit the targeting/localization ability of the antibodies. In the multistage delivery vehicle, PEGs attached to the first stage particle may perform shielding from the RES macrophages. Although the PEGs may hide antibodies on the first stage particle, the recognition/localization capability of the first stage particle is not limited to the antibodies, as other factors such as the particle's size and shape also may contribute to such capability. In some embodiments, the surface of the second stage particle has hydrophilic polymer chains, such as PEG chains, disposed on it.

In some embodiments, the surface of second stage particle is modified, for example, to facilitate the second stage particle's ability to load into a reservoir of the first stage particle and/or to facilitate the second stage particle's ability to reach its target site. The surface modification may include a chemical modification of the surface of the second stage particle and/or electrostatic modification of the surface of the second stage particle. For example, to facilitate loading of the second stage particles into a porous or nanoporous first stage particle, the surface of the second stage particles may be modified so that its properties are compatible with surface properties of pores of the porous or nanoporous first stage particle. For example, when the pores of the porous or nanoporous first stage particle are positively charged it may be preferably to modify the surface of the second stage particles so that they are electrostatically neutral or have a negative surface charge; while when the pores of the porous or nanoporous first stage particle are negatively charged, it may be preferably to modify the surface of the second stage particles so that they are electrostatically neutral or have a positive surface charge. The chemical and/or electrostatic surface modification of the second stage particles may be performed using the same methods as detailed above to the first stage particles.

For lipid containing second stage particles, such as liposomes or micelles, the electrostatic modification may be performed by incorporating in their lipid layers lipids that may affect the electrostatic charge of the liposome. For example, to form a positively charged cationic lipid containing particle, one may use cationic lipids, such as 1,2-Dioleyl-3-trymethylammoniumpropane (DOTAP); to form a negatively charged anionic lipid containing particle, anionic lipids, such as dioleoylphosphatidyl glycerol (DOPG); and to form a neutral lipid containing particle one may use, neutral lipids, such as DOPC.

In some embodiments, upon binding to the targeted cell or cells, the second stage particle may release its content into the cell's cytoplasm. In some embodiments, such release is activated by exogenous factors, such as electromagnetic radiation. For fullerene nanoparticles and carbon nanotubes, such radiation may be radio-frequency radiation, while for gold-shell nanoparticles, the radiation may be a near-infrared radiation. Activation of nanoparticulates by exogenous radiation is detailed, for example, Hirsch, L. R., Halas, N. J. & West, J. L. Anal. Chem. 75, 2377-2381 (2003); Hirsch, L. R., Halas, N. J. & West, J. L. Proc. Natl Acad. Sci. USA 100, 13549-13554 (2003); and O'Neal, D. P., Halas, N. J. & West, J. L. Cancer Lett. 209, 171-176 (2004).

In some embodiments, the content of the second stage particle is one or more active agents per se. In some embodiments, the second stage particle contains inside a third stage particle, which itself contains inside one or more active agents. The third stage particle may be, for example, a particle, that is small enough to be able to cross a nuclear membrane of the targeted cell. Thus, the third stage particle may serve for delivering to the cell's nucleus an active agent, that may be an agent acting against nucleic acids or a gene therapeutic agent. To be able to cross the nuclear membrane, the third stage particle may range from about 3 nm to about 10 nm. The ability to deliver nanoparticles in 3 nm to 10 nm size range may be one of the advantages of the multistage delivery vehicle as a conventional administration of such particles via injection usually results in their immediate globular clearance.

In some embodiments, the multistage vehicle includes a third stage. The third stage may be any nanoparticle that may fit inside the second stage particle. As with the second stage particle, the third stage particle may be a lipid based particle, such as a liposome, a micelle or lipid encapsulated perfluorocarbon emulsion; an ethosome; a carbon nanotube, such as single wall carbon nanotube; a fullerene nanoparticle; a metal nanoparticle, such gold nanoshell or triangular silver nanoparticle; a semiconductor nanoparticle, such as quantum dot or boron doped silicon nanowire; a polymer nanoparticle, such as particles made of biodegradable polymers and ion doped polyacrylamide particles; an oxide nanoparticle, such as iron oxide particle, a polymer coated iron oxide nanoparticle or a silicon oxide particle; a viral particle, such as an engineered viral particle or an engineered viruspolymer particle; a polyionic particle, such as leashed polycations; a ceramic particle, such as silica based ceramic nanoparticles, or a combination thereof. In some embodiments, the third stage particle is a nucleic acid nanoparticle, such as a small interfering RNA (siRNA) particle.

Loading Later Stage Particles into a Reservoir of Earlier Stage Particle

Later stage particles may be introduced into a earlier stage particle of an earlier stage by any appropriate technique. In some embodiments, one may soak nanoporous earlier stage particles fabricated in a solution containing a carrying fluid and the later stage particles, which may enter pores of the earlier stage particle via capillary action and/or diffusion. The carrying fluid may be a liquid that is biologically non-harmful and that is neutral with respect to the earlier stage particle's material. An example of the carrying fluid may be phosphate buffer saline (PBS) or a deionized water. The solution may also contain one or more additional agents, such one or more additional therapeutic agents and one or more appropriate penetration enhancers, desired to be introduced in the first stage particle. To maximize a load of the later stage particles, one may use a solution that has a saturated concentration of the later stage particles.

The earlier stage particles may be introduced into the solution in a form of suspension. Preparation of nanoporous particles suspension is detailed, for example, in U.S. patent application Ser. No. 2003/0114366. Pores of the nanoporous particles may be dried prior their submerging in the solution containing the later stage particles.

In some embodiments, the solution containing the later stage particles pores may be degassed prior to the introduction of the earlier stage particles. Then, the earlier stage particles may be submerged in the degassed solution in a sealed chamber. The earlier stage particles may be subjected to reduced pressure to ensure that trapped air is forced from the pores in the particles. Then the earlier stage particles may be fully immersed in the solution and the pressure in the sealed chamber may be elevated slightly above atmospheric to make sure that the solution enters the pores of the earlier stage particles. The earlier stage particles may then be trapped on a filter and dried using one of the three methods described below.

In some embodiments, to remove any trapped air within the reservoirs in the submerged earlier stage particles, the pressure within the chamber is reduced and then raised slightly above atmospheric pressure.

In some embodiments, after filling the solution into the pores of the earlier stage particles, drying is achieved by one or more of the following three methods. Water may be removed by evaporation under reduced pressure in a vacuum chamber, or by passage of a stream of warm air or an inert gas such as nitrogen over the surface particles collected on a filter, or by freeze drying. In the case of freeze drying, a flat heat exchanger may be placed in good thermal contact, e.g. directly below, the filter, on which the earlier stage particles have been collected. Refrigerant fluid at temperatures ranging from −20° C. to −60° C., such as Freon, or a cold liquid, such as liquid nitrogen, may be passed through the heat exchanger flowing into port and passing out port in order to freeze any water remaining within the pores. The pressure may be then reduced until all the water sublimes.

In some embodiments, for loading later stage particles into nanoporous earlier stage particles, a solution containing the earlier stage nanoporous particles, the later stage particles and a carrier liquid is prepared. The carrier liquid may be a physiological buffer, such as Tris-HCl. A concentration of the carrier liquid may be selected by using standard techniques to maximize loading of the later stage particle into the nanoporous earlier stage particles. For example, in some embodiments, for Tris-HCl, the optimal concentration may be selected from 1 to 500 mM.

Geometrical properties of the later stage particles, such as size and shape, may be selected to be compatible pore properties of the nanoporous earlier stage particles, such as pore density, pore size, and pore orientation.

In some embodiments, loading of the later stage particle into the nanoporous earlier stage particles is facilitated by agitating the solution containing both the later stage and earlier stage particles. Such agitation may be performed by spinning the solution in a rotating wheel. Agitation conditions, such as a rotation speed of the rotating wheel, may be optimized using standard techniques to achieve a desired loading degree and/or loading time.

In some embodiments, loading of the later stage particles into the earlier stage nanoporous particles is controlled by varying a concentration of the later stage particles in the solution. In some embodiments, the higher load may be achieved by using a higher concentration of the later stage particles in the solution. Yet, in some embodiments, one may achieve a higher load of the later stage particles by using a concentration of the later stage particles, which is lower than the highest possible concentration of the later stage particles in the solution. Determining a concentration maximizing loading of the later stage particles in the nanoporous earlier stage particles may be performed using standard methods.

In some embodiments, loading of the later stage particles into the earlier stage nanoporous particles is controlled by modifying a pore surface of the nanoporous earlier stage particles and/or a surface of the later stage particles in order to make them more compatible. Such modifying may be performed by modifying surface chemical groups on either surface and/or by modifying an electrical charge on either surface. For example, in some embodiments, to achieve a higher load of the later stage particle, one may use negatively charged surface of the later stage particles and positively charged porous surface of the earlier stage nanoporous particles or positively charged surface of the later stage particles and negatively charged porous surface of the earlier stage nanoporous particles. In some embodiments, a pore surface of the nanoporous earlier stage particles and a surface of the later stage particles are modified with chemical groups compatible with each other. For example, one of the pore surface of the nanoporous earlier stage particles and the surface of the later stage particles may be modified with carboxy groups; while the other may be modified with amino groups.

Active Agent

The active agent may be a therapeutic agent, an imaging agent or a combination thereof. The active agent may be any appropriate agent that may be released from a particle containing it. The selection of the active agent depends on the application.

When the active agent is not a particle of any stage per se, it may be introduced into particle using any appropriate technique. For example, when the active agent is doxorubicin, it may be introduced in a liposome particle using a protocol detailed in Working Example 4.

When the active agent is a particle of one of the stages of multistage delivery vehicle, the active agent may introduced using one of the methods disclosed above.

Therapeutic Agent

The therapeutic agent may be any physiologically or pharmacologically active substance that may produce a desired biological effect in a targeted site in an animal, such as a mammal or a human. The therapeutic agent may be any inorganic or organic compound, without limitation, including peptides, proteins, nucleic acids, and small molecules, any of which may be characterized or uncharacterized. The therapeutic agent may be in various forms, such as an unchanged molecules, molecular complex, pharmacologically acceptable salt, such as hydrochloride, hydrobromide, sulfate, laurate, palmitate, phosphate, nitrite, nitrate, borate, acetate, maleate, tartrate, oleate, salicylate, and the like. For acidic therapeutic agent, salts of metals, amines or organic cations, for example, quaternary ammonium, may be used. Derivatives of drugs, such as bases, esters and amides also may be used as a therapeutic agent. A therapeutic agent that is water insoluble may be used in a form that is a water soluble derivative thereof, or as a base derivative thereof, which in either instance, or by its delivery, is converted by enzymes, hydrolyzed by the body pH, or by other metabolic processes to the original therapeutically active form.

The therapeutic agent may be a chemotherapeutic agent, an immunosuppressive agent, a cytokine, a cytotoxic agent, a nucleolytic compound, a radioactive isotope, a receptor, and a pro-drug activating enzyme, which may be naturally occurring or produced by synthetic or recombinant methods, or any combination thereof.

Drugs that are affected by classical multidrug resistance, such as vinca alkaloids (e.g., vinblastine and vincristine), the anthracyclines (e.g., doxorubicin and daunorubicin), RNA transcription inhibitors (e.g., actinomycin-D) and microtubule stabilizing drugs (e.g., paclitaxel) may have particular utility as the therapeutic agent.

A cancer chemotherapy agents may be a preferred therapeutic agent. Useful cancer chemotherapy drugs include nitrogen mustards, nitrosorueas, ethyleneimine, alkane sulfonates, tetrazine, platinum compounds, pyrimidine analogs, purine analogs, antimetabolites, folate analogs, anthracyclines, taxanes, vinca alkaloids, topoisomerase inhibitors and hormonal agents. Exemplary chemotherapy drugs are Actinomycin-D, Alkeran, Ara-C, Anastrozole, Asparaginase, BiCNU, Bicalutamide, Bleomycin, Busulfan, Capecitabine, Carboplatin, Carboplatinum, Carmustine, CCNU, Chlorambucil, Cisplatin, Cladribine, CPT-11, Cyclophosphamide, Cytarabine, Cytosine arabinoside, Cytoxan, Dacarbazine, Dactinomycin, Daunorubicin, Dexrazoxane, Docetaxel, Doxorubicin, DTIC, Epirubicin, Ethyleneimine, Etoposide, Floxuridine, Fludarabine, Fluorouracil, Flutamide, Fotemustine, Gemcitabine, Herceptin, Hexamethylamine, Hydroxyurea, Idarubicin, Ifosfamide, Irinotecan, Lomustine, Mechlorethamine, Melphalan, Mercaptopurine, Methotrexate, Mitomycin, Mitotane, Mitoxantrone, Oxaliplatin, Paclitaxel, Pamidronate, Pentostatin, Plicamycin, Procarbazine, Rituximab, Steroids, Streptozocin, STI-571, Streptozocin, Tamoxifen, Temozolomide, Teniposide, Tetrazine, Thioguanine, Thiotepa, Tomudex, Topotecan, Treosulphan, Trimetrexate, Vinblastine, Vincristine, Vindesine, Vinorelbine, VP-16, and Xeloda.

Useful cancer chemotherapy drugs also include alkylating agents, such as Thiotepa and cyclosphosphamide; alkyl sulfonates such as Busulfan, Improsulfan and Piposulfan; aziridines such as Benzodopa, Carboquone, Meturedopa, and Uredopa; ethylenimines and methylamelamines including altretamine, triethylenemelamine, trietylenephosphoramide, triethylenethiophosphaoramide and trimethylolomelamine; nitrogen mustards such as Chlorambucil, Chlornaphazine, Cholophosphamide, Estramustine, Ifosfamide, mechlorethamine, mechlorethamine oxide hydrochloride, Melphalan, Novembiehin, Phenesterine, Prednimustine, Trofosfamide, uracil mustard; nitroureas such as Cannustine, Chlorozotocin, Fotemustine, Lomustine, Nimustine, and Ranimustine; antibiotics such as Aclacinomysins, Actinomycin, Authramycin, Azaserine, Bleomycins, Cactinomycin, Calicheamicin, Carabicin, Carminomycin, Carzinophilin, Chromoinycins, Dactinomycin, Daunorubicin, Detorubicin, 6-diazo-5-oxo-L-norleucine, Doxorubicin, Epirubicin, Esorubicin, Idambicin, Marcellomycin, Mitomycins, mycophenolic acid, Nogalamycin, Olivomycins, Peplomycin, Potfiromycin, Puromycin, Quelamycin, Rodorubicin, Streptonigrin, Streptozocin, Tubercidin, Ubenimex, Zinostatin, and Zorubicin; anti-metabolites such as Methotrexate and 5-fluorouracil (5-FU); folic acid analogues such as Denopterin, Methotrexate, Pteropterin, and Trimetrexate; purine analogs such as Fludarabine, 6-mercaptopurine, Thiamiprine, and Thioguanine; pyrimidine analogs such as Ancitabine, Azacitidine, 6-azauridine, Carmofur, Cytarabine, Dideoxyuridine, Doxifluridine, Enocitabine, Floxuridine, and 5-FU; androgens such as Calusterone, Dromostanolone Propionate, Epitiostanol, Rnepitiostane, and Testolactone; anti-adrenals such as aminoglutethimide, Mitotane, and Trilostane; folic acid replenisher such as frolinic acid; aceglatone; aldophosphamide glycoside; aminolevulinic acid; Amsacrine; Bestrabucil; Bisantrene; Edatraxate; Defofamine; Demecolcine; Diaziquone; Elfornithine; elliptinium acetate; Etoglucid; gallium nitrate; hydroxyurea; Lentinan; Lonidamine; Mitoguazone; Mitoxantrone; Mopidamol; Nitracrine; Pentostatin; Phenamet; Pirarubicin; podophyllinic acid; 2-ethylhydrazide; Procarbazine; PSK®; Razoxane; Sizofrran; Spirogermanium; tenuazonic acid; triaziquone; 2,2',2"-trichlorotriethylamine; Urethan; Vindesine; Dacarbazine; Mannomustine; Mitobronitol; Mitolactol; Pipobroman; Gacytosine; Arabinoside ("Ara-C"); cyclophosphamide; thiotEPa; taxoids, e.g., Paclitaxel (TAXOL®, Bristol-Myers Squibb Oncology, Princeton, N.J.) and Doxetaxel (TAXOTERE®, Rhone-Poulenc Rorer, Antony, France); Chlorambucil; Gemcitabine; 6-thioguanine; Mercaptopurine; Methotrexate; platinum analogs such as Cisplatin and Carboplatin; Vinblastine; platinum; etoposide (VP-16); Ifosfamide; Mitomycin C; Mitoxantrone; Vincristine; Vinorelbine; Navelbine; Novantrone; Teniposide; Daunomycin; Aminopterin; Xeloda; Ibandronate; CPT-11; topoisomerase inhibitor RFS 2000; difluoromethylornithine (DMFO); retinoic acid; Esperamicins; Capecitabine; and pharmaceutically acceptable salts, acids or derivatives of any of the above. Also included are anti-hormonal agents that act to regulate or inhibit hormone action on tumors such as anti-estrogens including for example Tamoxifen, Raloxifene, aromatase inhibiting 4(5)-imidazoles, 4 Hydroxytamoxifen, Trioxifene, Keoxifene, Onapristone, And Toremifene (Fareston); and anti-androgens such as Flutamide, Nilutamide, Bicalutamide, Leuprolide, and Goserelin; and pharmaceutically acceptable salts, acids or derivatives of any of the above.

Cytokines may be also used as the therapeutic agent. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-$\alpha$ and -$\beta$; mullerian-inhibiting substance; mouse gonadotropin-associated peptide; inhibin; activin; vascular endothelial growth factor; integrin; thrombopoietin (TPO); nerve growth factors such as NGF-$\beta$; platelet growth factor; transforming growth factors (TGFs) such as TGF-$\alpha$ and TGF-$\beta$; insulin-like growth factor-I and -II; erythropoietin (EPO); osteoinductive factors; interferons such as interferon-$\alpha$, -$\beta$ and -$\gamma$; colony stimulating factors (CSFs) such as macrophage-CSF (M-CSF); granulocyte-macrophage-CSF (GM-CSF); and granulocyte-CSF (GCSF); interleukins (ILs) such as IL-1, IL-1a, IL-2, IL-3, IL-4, IL-5, IL-6, IL-7, IL-8, IL-9, IL-11, IL-12, IL-15; a tumor necrosis factor such as TNF-$\alpha$ or TNF-$\beta$; and other polypeptide factors including LIF and kit ligand (KL). As used herein, the tern cytokine includes proteins from natural sources or from recombinant cell culture and biologically active equivalents of the native sequence cytokines.

Imaging Agent

The imaging agent may be any substance that provides imaging information about a targeted site in a body of an animal, such as a mammal or a human being. The imaging agent may comprise magnetic material, such as iron oxide, for magnetic resonance imaging. For optical imaging, the active agent may be, for example, semiconductor nanocrystal or quantum dot. For optical coherence tomography imaging, the imaging agent may be metal, e.g., gold or silver, nanocage particles. The imaging agent may be also an ultrasound contrast agent, such as a micro or nanobubble or iron oxide micro or nanoparticle.

Administration

The multistage delivery vehicle may be administered as a part of a composition, that includes a plurality of the vehicles, to a subject, such as human, via any suitable administration method in order to treat, prevent and/or monitor a physiological condition, such as a disease. The particular method employed for a specific application is determined by the attending physician. Typically, the composition may be administered by one of the following routes: topical, parenteral, inhalation/pulmonary, oral, vaginal and anal.

Embodiments of the multistage delivery vehicles may be particularly useful for oncological applications, i.e. for treatment and/or monitoring cancer or a condition, such as tumor associated with cancer. For example, skin cancer may be treated and/or monitored by topical application of, preferably, a viscous suspension; lung cancer may be treated and/or monitored by inhalation of an aerosolized aqueous microdevice suspension; cervical cancer may be treated and/or monitored by vaginal administration of a microdevice suspension; and colon cancer may be treated and/or monitored by rectal administration of such a suspension. The majority of therapeutic applications may involve some type of parenteral administration, which includes intravenous (i.v.), intramuscular (i.m.) and subcutaneous (s.c.) injection.

Administration of the multistage delivery vehicles may be systemic or local. The non-parenteral examples of administration recited above, as well as i.m. and s.c. injections, are examples of local administration. Intravascular administration may be either local or systemic. Local intravascular delivery may be used to bring a therapeutic substance to the vicinity of a known lesion by use of guided catheter system, such as a CAT-scan guided catheter. General injection, such as a bolus i.v. injection or continuous/trickle-feed i.v. infusion are typically systemic.

For intravenous administration, the multistage delivery vehicle may be formulated as a suspension that contains a plurality of the vehicles. Preferably, the vehicles are uniform in their dimensions and their content. To form the suspension, the vehicles as described above may be suspended in any suitable aqueous carrier vehicle. A suitable pharmaceutical carrier is one that is non-toxic to the recipient at the dosages and concentrations employed and is compatible with other ingredients in the formulation. Preparation of suspension of microfabricated particles is disclosed, for example, in US patent application publication No. 20030114366.

For oral administration, the multistage delivery vehicle may administered as a part of an oral composition made up of a plurality of the vehicles. Preferably, the vehicles in the composition are uniform in dimensions, i.e. the first stage particles of each vehicle have the same or substantially the same dimension; the second stage particles of each vehicle have the same or substantially the same dimensions. The composition may be made by mixing the vehicles with suitable non-aqueous carriers, such as oil or micronized powder, and filled in unit dose amounts into standard enteric-coated capsules or, alternatively, compressed into tablets and coated with an enteric coating material. The enteric coating ensures that the vehicles are transported in dry form through the low (acidic) pH environment of the stomach and released at pre-selected regions of the small or large intestine.

The composition may be coated with a protective polymer. This material may be applied by film coating technology to either tablets or capsules to protect the product from the effects of, or prevent release of drugs in, the gastric environment. Such coatings are those, which remain intact in the stomach, but may dissolve and release the contents of the dosage form once it reaches the small intestine. The purpose of an enteric coating may be to delay release of the first stage particle's content.

One of the most extensively used enteric polymer may be cellulose acetate phthalate (CAP). Another useful polymer may be polyvinyl acetate phthalate (PVAP), which is less permeable to moisture, more stable to hydrolysis and able to ionize at a lower pH than is CAP. These properties may allow more reliable release in the duodenum. Another example of currently used polymers may be those based on methacrylic acid-methacrylic acid ester copolymers with acid ionizable groups. Represented among these are polymers having the tradename Eudragit available through Rohm Pharma. Generally, the enteric coating may be applied from about 0.5% by weight to about 10% by weight of the tablet or capsule.

In some embodiments, a less water-soluble polymer, such as methylcellulose, could be used to delay release of the drug from the chambers following release of the particles in the duodenum. ChronSetRTM technology developed by ALZA Corporation (Mt. View, Calif.) may be used to release a bolus of the multistage delivery vehicles at designated times and at targeted sites after passage from the stomach into the small intestine. In this case, a suspension of the vehicles may be loaded into ChronSet capsules. After swallowing, the capsules pass intact through the stomach. The shell may be engineered to regulate the rate of water imbibition the osmotically permeable portion of the system. The osmotic engine may expand to push and separate two halves of the capsule. The length of the capsule halves may be specifically designed to produce separation at pre-selected times. The contents of each capsule may be expelled into the intestinal lumen at 2 to 20 hours after administration. Greater than 80% of contents (in this case a suspension of drug-filled microfabricated particles) may be expelled within 15 minutes time frame. This approach may provide a means of releasing the suspension of the vehicles at preselected areas of the small or large intestine. Such a system may be used to release the multistage delivery vehicles at sites in the small or large intestine that are optimal for binding, such as areas, which contain receptors for the muco-adhesive ligand grafted to the particles, and/or absorption, such as regions of the intestinal epithelium that are sensitive to the permeation enhancers contained inside the first stage particle.

Embodiments described herein are further illustrated by, though in no way limited to, the following working examples.

WORKING EXAMPLE 1

The following experiments were conducted to study loading and release of selected second stage particles into nanoporous silicon first stage microparticles. Biodegradation and biocompatibility of the nanoporous silicon first stage particles was also studied.

Materials and Methods

Z2 Analysis

Particles were counted in a Z2 Coulter® Particle Counter and Size Analyzer (Beckman Coulter). The aperture size used for particle analysis was 50 μm. The lower and upper size limits for analysis were set at 1.8 and 3.6 μm. For analysis,particles were suspended in the balanced electrolyte solution of the instrument (ISOTON® II Diluent) and counted. The total volume of original suspension of particles did not exceed 0.3% of the final analysis volume.

Oxidation of Silicon Microparticles

Silicon microparticles in IPA were dried in a glass beaker kept on a hot plate (80-90° C.). Silicon particles were oxidized in piranha (1 volume $H_2O_2$ and 2 volumes of $H_2SO_4$). The particles sonicated after $H_2O_2$ addition and then acid was added. The suspension was heated to 100-110° C. for 2 hours with intermittent sonication to disperse the particles. The suspension was then washed in DI water till the pH of the suspension is ~5.5-6. Particles were then transferred to appropriate buffer, IPA or stored in water and refrigerated till further use.

Surface Modification of Si Particles with APTES

Prior to the silanization process, the oxidized particles were hydroxylated in 1.5 M $HNO_3$ acid for approximately 1.5 hours (room temperature). Particles were washed 3-5 times in DI water (washing includes suspending in water and centrifuging, followed by the removal of supernatant and the repeating of the procedure).

The particles were suspended in IPA (isopropyl alcohol) by washing them in IPA twice. They were then suspended in IPA containing 0.5% (v/v) of APTES (3-aminopropyltriethoxysilane) for 45 minutes at room temperature. The particles were then washed with IPA 4-6 times by centrifugation and stored in IPA refrigerated. Alternatively, they were aliquoted, dried and stored under vacuum and dessicant till further use.

Attaching PEG to APTES Modified Particles

PEG was attached to the microparticles to provide a spacer for further coupling with anti-VEGFR2 antibody. Fmoc-PEG-NHS, which provided the NHS ester for rapid coupling to amine groups and an Fmoc group to protect the amine on the PEG, was useed. The 106-109 particles/ml of APTES modified microparticles were resuspended in PBS (pH-7.2) and Fmoc-PEG-NHS at a concentration of 1-10 mM added to the particles.

Coupling was carried out for 30 min to 1 h at room temperature, then unreacted Fmoc-PEG-NHS groups were washed by centrifugation 3-5 times in PBS. The Fmoc group on the distal end of PEG coupled to the silicon microparticles were deprotected with piperidine (20% v/v for 30 min) to provide a free amine on the PEG for further coupling with antibodies.

Fluorescent Tagging of Anti-VEGFR2

The antibody to VEGFR2 was conjugated with Alexa 488 using an antibody labeling kit from Invitrogen Corp. The fluorescent tag was conjugated to the antibody by following the procedure provided in the manual of the kit. 1 mg/ml of antibody was used for tagging. The amount of antibody conjugated to the fluorescent tag was determined by analyzing the antibody with a DU® 730 UV/Vis Spectrophotometer (Beckman Coulter Inc., CA, USA) at 280 and 494 nm. The amount of antibody conjugated was found to be 407 µg/ml.

Coupling Anti-VEGFR2 to PEG Modified Particles

Figure 3:
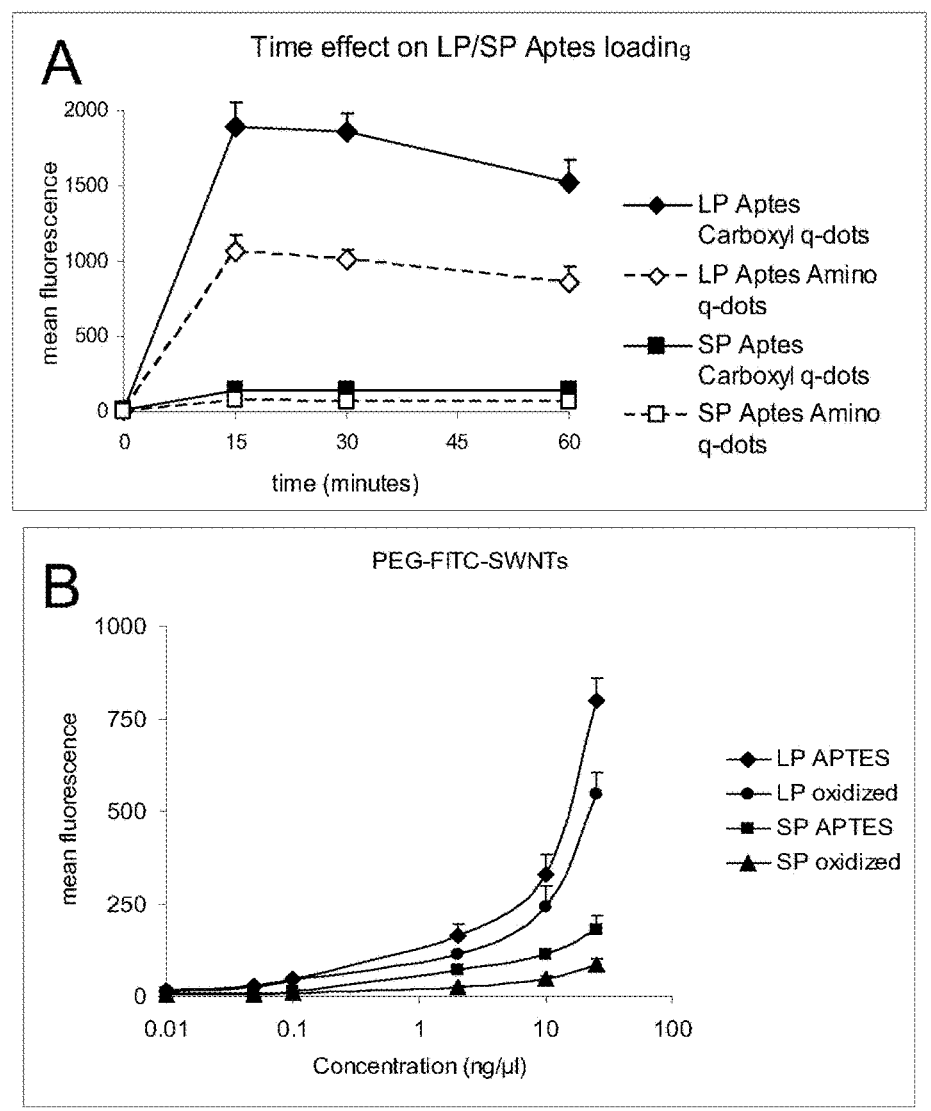
FIG. 3, Panel A, depicts time dependence of amino and carboxy modified quantum dots (q-dots) in APTES modified "large pore" LP and "small pore" nanoporous silicon first stage particle.

Silicon particles, resuspended in PBS, were treated with the heterobifunctional crosslinker ANB-NOS (dissolved in DMF and added to a final concentration of 10 mM) for 30 min to 1 h. The reaction was carried out in the dark to prevent the photolysis of the nitrophenyl azide group on the crosslinker The particles were then washed with PBS to remove unreacted crosslinker and mixed with the fluorescently labeled anti-VEGFR2. 4.6×106 particles were used for each experimental point. The different amounts of antibody used, were 0.814, 0.407, and 0.163 µg, corresponding to 2.7, 1.35, and 0.54 µg/ml respectively, and exposed to UV light for 10-15 min to couple the amine groups present on the antibody to the attached crosslinker Determining Buffer Cconcentration for Loading of Amino-PEG Quantum-dots (Q-dots) into Porous Silicon Microparticles In a low binding micro centrifuge tube, 3.0×10$^5$ large pore (LP) and small pore (SP) oxidized silicon (stored at the concentration of 300×10$^6$ particles/ml) or APTES modified microparticles (stored at the concentration of 200×10$^6$ particles/ml), and 2 µM Amino-PEG Q-dots or Carboxyl Q-dots were combined in a solution containing 10, 20, 50, 100 or 200 mM of TRIS-HCl at pH 7.3. Samples were incubated in a rotating wheel (20 rpm) for 15 minutes at 25° C. in a final volume of 20 µl for each experimental point. After incubation, the samples were diluted with Tris 20 mM, pH 7.3 to 150 µl and promptly read at a FACScalibur flow cytometer for fluorescence intensity. FIG. 3, Panel A, presents results of time dynamics for loading carboxy modified quantum dots and amino modified quantum dots into APTES modified LP and SP silicon particles. FIG. 4, Panels A-D present results of time dynamics for loading carboxy modified quantum dots and amino modified dots into (Panel A) LP oxidized silicon particles; (Panel B) LP APTES modified silicon particles; (Panel C) SP oxidized silicon particles and (Panel D) SP APTES modified silicon particles. Each of Panels A-D also presents time dynamics for loading PEG-FITC single wall carbon nanotubes, as described below.

Determining Concentration of Amino-PEG and Carboxyl Q-dots for Porous Silicon Microparticles Loading In a low binding micro centrifuge tube, 3.0×10$^5$ LP or SP oxidized silicon or APTES modified microparticles, were combined with 0.01, 0.1, 1, 10, 100, 1000 and 2000 nM Amino-PEG or Carboxyl Q-dots respectively, in 200 mM TRIS-HCl pH 7.3. Samples were incubated in a rotating wheel (20 rpm) for 15 minutes at 25° C. in a final volume of 20 µl for each experimental point. After incubation, the samples were diluted with Tris 20 mM, pH 7.3 to 150 µl and promptly read at a FACScalibur flow cytometer for fluorescence intensity.

Determining Time for Loading of Amino-PEG and Carboxyl Q-dots into Porous Silicon Microparticles In a low binding micro centrifuge tube, 1.2×10$^6$ LP and SP oxidized silicon or APTES modified microparticles, were combined with 2 µM Amino-PEG Q-dots or Carboxyl Q-dots in 200 mM TRIS-HCl pH 7.3 in a 80 µl final volume. Particles and Q-dots were incubated in a rotating wheel (20 rpm) and sampled out from the vial after 15, 30, 45 and 60 minutes at 25° C. After incubation, the samples were diluted with Tris 20 mM, pH 7.3 to 150 µl and promptly read at a FACScalibur flow cytometer for fluorescence intensity.

Loading of Amino-PEG and of Carboxyl Q-dots into Oxidized and APTES Modified Porous Silicon Microparticles 2.1×10$^6$ LP silicon microparticles either oxidized or APTES modified were combined with 2 µM Amino-PEG Q-dots or Carboxyl Q-dots respectively, in a TRIS-HCl 200 mM pH7.3 solution. Final incubation volume was 140 µl. Samples were incubated in a rotating wheel (20 rpm) for 15 minutes at 25° C. The microparticles were then washed in 1.4 mL deionized water (10 folds dilution), and centrifuged 5 minutes at 4200 RPM in a Beckman Coulter Allegra X-22 centrifuge. Particles pellet was resuspended in 70 µl of deionized water and 10 µl were taken out the vial, diluted with a TRIS 20 mM, pH 7.3 solution to 150 µl final volume. Sample's fluorescence was immediately read with Becton Dickinson FACScalibur flow cytometer and recorded as time 0 or loading fluorescence.

Figure 5:
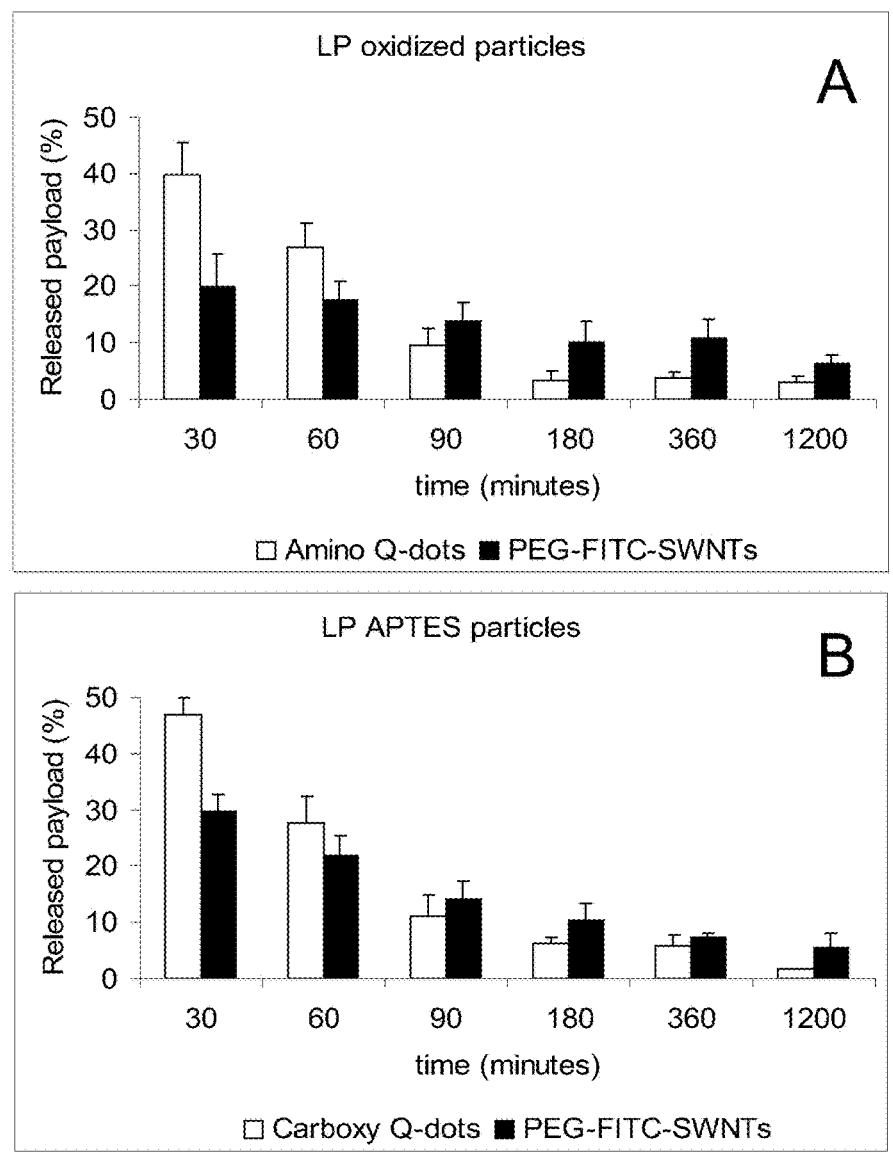
FIG. 5 demonstrates time dynamics of second stage nanoparticles release from LP oxidized nanoporous silicon first stage particles (Panel A) and LP APTES modified nanoporous silicon first stage particles (Panel B). In Panel A and Panel B, Y-axis reads released payload (%).

Release of Amino-PEG and of Carboxyl Q-dots from Oxidized and APTES Modified Porous Silicon Microparticles The residual 60 µl were diluted 10 times into 600 µL of TRIS-HCL 20 mM NaCl 0.9% release buffer. 100 µl were taken out this solution and additionally diluted 5 times by aliquoting the sample into tubes pre filled with 400 uL TRIS-HCL 20mM NaCl 0.9% release buffer. Final dilution at this point was 500 folds. Samples were put in a rotating wheel (20 rpm) for the given amount of time (15, 45, 90, 180, 360 and 1200 minutes) minutes at 37° C. At each time point the aliquots were centrifuged 5 minutes at 4200 RPM in a Beckman Coulter Allegra X-22 centrifuge. Each pellet was then resuspended in 150 µl of TRIS 20 mM and fluorescence was immediately read with a Becton Dickinson FACScalibur flow cytometer. FIG. 5A presents time dynamics of release of amino-modified quantum dots from LP oxidized silicon particles. FIG. 5B presents time dynamics of release of carboxy modified quantum dots from APTES modified LP silicon particles.

Determining Buffer Concentration for Loading of Poly (Ethylene Glycol) (PEG) Fluorescein Isothiocyanate (FITC) Conjugated Single Walled Carbon Nanotubes (SWNTs) into Porous Silicon Microparticles In a low binding micro centrifuge tube, $3.0 \times 10^5$ large pore oxidized silicon or APTES modified microparticles, were combined with 20 ng/µl PEG-FITC-SWNTs in a solution containing different molarities (20, 100, 200 mM) of TRIS-HCl pH 7.3. Final volume was 20 µl for each experimental point. Samples were incubated in a rotating wheel (20 rpm) for 15 minutes at 25° C. After incubation, the samples were resuspended in 150 µl of TRIS 20 mM and immediately read at a FACScalibur flow cytometer for fluorescence intensity.

Determining Time for Loading of PEG-FITC-SWNTs into Porous Silicon Microparticles In a low binding micro centrifuge tube, $1.2 \times 10^6$ large pore oxidized silicon or APTES modified microparticles, were combined with 20 ng/µl PEG-FITC-SWNTs in 20 mM TRIS-HCl pH 7.3 in a 80 µl final volume. Particles and SWNTs were incubated in a rotating wheel (20 rpm) and sampled out from the vial after 15, 30, 45 and 60 minutes at 25° C. After incubation, the samples were diluted with Tris 20mM, pH 7.3 to 150 µl and promptly read at a FACScalibur flow cytometer for fluorescence intensity.

Determining Concentration of PEG-FITC-SWNTs for Porous Silicon Microparticles Loading In a low binding micro centrifuge tube, $3.0 \times 10^5$ LP or SP oxidized silicon or APTES modified microparticles, were combined with 1, 10, 20 and 50 ng/µl PEG-FITC-SWNTs in 20 mM TRIS-HCl pH 7.3 in a final volume of 20 µl for each experimental point. After incubation, the samples were diluted with Tris 20 mM, pH 7.3 to 150 µl and promptly read at a FACScalibur flow cytometer for fluorescence intensity.

Determining Fluorescence Intensity and Quenching Effect of PEG-FITC-SWNTs Using Fluorimetry A concentration curve for PEG-FITC SWNTs in 20 mM TRIS-HCL pH 7.3 was determined using a SPECTRAmax fluorimeter. A serial dilution was performed, starting with 35 ng/µl and proceeding by a factor of 1:2 down to minimum detectable amount of 107 pg/µl. The aliquots were placed in a 96 well plate and the fluorescence was read using excitation at 485, and emission at 520. Fluorescence quenching was observed at the higher concentrations of SWNTs, as shown by their lower fluorescence.

Loading of PEG-FITC-SWNTs into Oxidized and APTES Modified Porous Silicon Microparticles $1.8 \times 10^6$ "large pore" (LP, approximately 30 nm) silicon microparticles were combined with 20 ng/µl PEG-FITC-SWNTs in a 20 mM TRIS-HCl pH7.3 solution. Final incubation volume was 120 µl. Samples were incubated in a rotating wheel (20 rpm) for 15 minutes at 25° C. The microparticles were then washed in 1.2 mL deionized water (10 folds dilution), and centrifuged 5 minutes at 4200 RPM in a Beckman Coulter Allegra X-22 centrifuge. After incubation, the supernatants were removed and placed in a 96 well plate for fluorescence reading using the SPECTRAmax plate reader.

Particles pellet was re-suspended in 60 µl of deionized water and 10 µl were taken out the vial, diluted with a TRIS 20 mM, pH 7.3 solution to 150 µl final volume. Sample's fluorescence was immediately read with Becton Dickinson FACScalibur flow cytometer and recorded as time 0 or loading fluorescence.

Release of PEG-FITC-SWNTs from Oxidized and APTES Modified Porous Silicon Microparticles The residual 50 µl were diluted 10 times into 500 µL of TRIS-HCL 20mM NaCl 0.9% release buffer. 100 µl were taken out this solution and additionally diluted 5 times by aliquoting the sample into tubes pre filled with 400 uL TRIS-HCL 20 mM NaCl 0.9% release buffer. Final dilution at this point was 500 folds. Samples were put in a rotating wheel (20 rpm) for the given amount of time (15, 45, 120, 240 and 1200 minutes) minutes at 37° C. At each time point the aliquots were centrifuged 5 minutes at 4200 RPM in a Beckman Coulter Allegra X-22 centrifuge. The supernatants were removed and placed in a 96 well plate for fluorescence reading using the SPECTRAmax plate reader. Each pellet was then resuspended in 150 µl of TRIS 20 mM and fluorescence was promptly read with a Becton Dickinson FACScalibur flow cytometer. FIG. 5A presents time dynamics of release of PEG-FITC-SWNTs from LP oxidized silicon particles. FIG. 5B presents time dynamics of release of PEG-FITC-SWNTs from APTES modified LP silicon particles.

Loading of Nanoliposomes into Oxidized and APTES Modified Porous Silicon Microparticles $1.5 \times 10^6$ LP and SP oxidized silicon microparticles were combined with 10 ng/µl of liposomes, containing an Alexa fluo 555 conjugated siRNA, in a 20 mM TRIS-HCl pH7.3 solution. Particles and nanoliposomes were incubated in a rotating wheel (20 rpm) and sampled out from the vial after 15, 30 and 60 minutes at 25° C. After incubation, the samples were diluted with Tris 20 mM, pH 7.3 to 150 µl and promptly read at a FACScalibur flow cytometer for fluorescence intensity.

Degradation $5 \times 10^6$ LP and SP oxidized silicon particles were either mixed in a solution containing 2.5 mM TRIS and 0.9% NaCl at pH 7.3 (Saline) or in cell culture media supplemented with 10% FBS (CCM). The mixture was incubated in a rotating wheel (8 rpm) at 37° C. and sampling for SEM, Z2 and ICP was performed at time 0 and after 6, 18 and 24 hours.

The experiment was designed in order to have enough material to perform the three types of analysis for the degradation study in parallel at the same time, thus avoiding differences due to uncontrolled or unnoticed variables. This protocol therefore applied to the samples obtained for SEM, Z2 and ICP.

An additional degradation experiment was performed to provide material for the toxicity experiment with HUVEC cells. For each experimental point. we incubated $3 \times 10^6$ LP, oxidized or Aptes modified, or SP, oxidized or Aptes modified, silicon particles in CCM in a rotating wheel (8 rpm) at 37° C. for 24.

ICP

To understand whether the porous Silicon particles disappeared from the solutions, they were incubated in, the porous Silicon particles were dissolved in Silicic Acid and studied by a technique called Inductive Coupled Plasma Atomic Emission Spectrometry (ICP-AES).

This methodology allows quantifying the absolute amount of any given element present in a solution. Amples were withdrawn at the same time points, the Z2 and the SEM analysis and centrifuged them to pellet down the particles that were not degraded yet. The surnatants filtered through a 0.450 µm filter unit were analyzed with ICP.

Cell Culture

Half a million freshly isolated Human Umbelical Vein Endothelial Cells (HUVEC) (Clonetics™ Cambrex Bio Science Walkersville, Inc) were plated in M199 medium (Gibco/Life Technologies Inc.) supplemented with 10% foetal calf serum (FCS, Gibco), containing 100 IU/ml penicillin (Sigma), 100 g/ml streptomycin (Sigma), 7.5 IU/ml heparin (Sigma), 2 ng/ml epidermal growth factor (EGF) (R&D system) and 250 pg/ml endothelial cell growth factor (-ECGF) (BioSource, USA), referred to as complete medium. Confluent cells were detached with trypsin (Sigma) for subculturing. The cells were expanded until passage 6 and used for the biocompatibility studies.

Microscopy

Cells were analyzed in bright field contrast with an Olympus CKX41 microscope with a 40× magnification lens. Images were taken with an SP-350 Olympus True-Pic TURBO Image Processor camera.

LDH Toxicity Assay

For the calibration of the toxicity assay, different amount of cells (125, 250, 500, 1000, 2000) were seeded in three 96 well plates. After 12, 24 and 48 hours the cell culture media was replaced with fresh media containing 1% Triton. The cells were incubated at room temperature (RT) for 10 minutes then spun down for 3 minutes at 1200 rpm and 100 μl of cell culture media were transferred into a replica plate kept on ice. 100 μl of a solution containing the reconstituted catalyst and the dye (Biovision LDH Cytotoxicity Assay Kit) was added to each well and the plate was transferred on an orbital shaker, covered with foil and shaked at RT for 20 minutes. The plate was then transferred in a SPECTRAmax fluorimeter and absorbance at 490 nm was read. All the experiments were done in triplicate and results expressed as mean values with standard deviations.

For the experiment, 1000 cells were seeded and, after the cells attached on the surface (approximately 6 hours), different amount of LP oxidized, SP oxidized, LP APTES and SP APTES Silicon particles (1000, 5000 and 10000, corresponding to a 1:1, 1:5, 1:10 cells:particles ratio) resuspended in 2 μl of sterile, deionized $H_2O$ were added to the media. As a positive control, 2 μl of sterile, deionized $H_2O$ were added to the cells while as a negative control we added 50 μg/ml of Cis-platinum to cell culture media.

The plates were incubated at 37° C. and, at the time points of 12, 24, 48 and 72 hours, the toxicity assay was performed as described for the calibration assay with the exception of Triton addition. All the experiments were done in triplicate and results expressed as mean values with standard deviations.

MTT Assay

For the calibration of the MTT assay, different amount of cells (125, 250, 500, 1000, 2000) were seeded in three 96 well plates. After 12, 24 and 48 hours the cell culture media was replaced with fresh media containing 50 μl of MTT dye. The cells were incubated at 37° C. for 4 hours then the media and MTT were removed and 200 μl of DMSO and 25 μl of a 0.1M glycine, 0.1 M NaCl, pH 10.5, solution were added to each well and the plate was incubated at RT for 10 minutes. The plate was then transferred in a SPECTRAmax fluorimeter and absorbance at 570 nm was read. All the experiments were done in triplicate and results expressed as mean values with standard deviations.

For the experiment 1000 cells were seeded and, after the cells attached on the surface and generated a 50% confluent cell bed (approximately 6 hours), different amount of LP oxidized, SP oxidized, LP APTES and SP APTES Silicon particles (1000, 5000 and 10000, corresponding to a 1:1, 1:5, 1:10 cells:particles ratio) resuspended in 2 gl of sterile, deionized $H_2O$ were added to the media. As a positive control, 2 μl of sterile, deionized $H_2O$ were added to the cells while as a negative control we added 50 μg/ml of Cis-platinum to cell culture media.

The plates were incubated at 37° C. and, at the time points of 12, 24, 48 and 72 hours, the medium was removed from the well and the cells extensively washed with sterile PBS to remove Silicon particles. The proliferation assay was then performed as described for the calibration assay. All the experiments were done in triplicate and results expressed as mean values with standard deviations.

Propidium Iodide Staining $0.6 \times 10^6$ cells were seeded in 25 $cm^2$ flasks and when the cells were attached (approximately 6 hours later, when the cells generated a 60% confluent cell bed), $3 \times 10^6$ of either LP oxidized, SP oxidized, LP APTES or SP APTES Silicon particles (1:5 ratio) resuspended in 20 μl of sterile, deionized $H_2O$, were added to the medium of each flask. As a positive control 20 μl of sterile, deionized $H_2O$ were added to the cells while as a negative control we added 50 μg/ml of Cis-platinum to cell culture media. As an additional control, the same amount of HUVEC cells was seeded in 75 $cm^2$ flasks to allow them to freely grow without reaching confluency during the experiment.

After 12, 24, 48 and 72 hours cells were washed 3 times with 5 ml of sterile PBS then were trypsinized, harvested and centrifuged. After an additional washing step with PBS, each cell pellet was resuspended in 250 μl of PBS and 750 μl of ice-cold methanol were added to cell suspensions while gently vortexing. Fixation was carried on for 20 minutes then the cells were spun down and washed twice with PBS. A solution containing (50 μg/ml propidium iodide in 10 mM Tris, 5 mM $MgCl^2$, pH 7.3 and 75 μg/ml RNAse) was then added to the cell pellet and the suspension was incubated in dark on a rotating wheel (5 rpm) for 60 minutes. Samples were then transferred into FACS tubes and immediately read with a Becton Dickinson flow cytometer.

Flow Cytometry Setup

Particles were assessed for fluorescence using a FACS Calibur (Becton Dickinson). Bivariate dot-plots defining log SSC versus log FSC were used to evaluate the size and shape of the Silicon particles (3 microns in diameter, 1.5 in height) used and to exclude from the analysis non-specific events. Control rainbow BD CalibriteTM beads (3.5 micron in size) were analyzed as a standard.

A polygonal region (R1) was defined around the centre of the population excluding the events that were to close to the noise signal of the instrument. For each sample, the number of particles detected in the R1 region was above 80%.

For mean fluorescence intensity (MFI) determination, log FL1 and FL2 versus log FSC dot-plots were created by gating on the events falling within the defined region (R1). The peaks generated by each of the samples were analyzed in the corresponding fluorescent histogram and the geometric mean values recorded.

For particles detection, detectors used were forward scatter (FSC) E-1 and side scatter (SSC) with 474V voltage set. The fluorescent detector FL1 was set at 800V.

Green fluorescence (FITC and Q-dots525) was detected using FL1, 530/30 nm band-pass filter. Orange and red fluorescence (Q-dots D565 and Propidium Iodide) was detected using FL2. As single color detection only was being analyzed compensation was set at zero. Instrument calibration was carried out before, in between and after each series of acquisition using rainbow BD Calibrite™ beads.

For cells detection, detectors used were linear forward scatter (FSC) E00 with an amplification gain of 4.59 and linear side scatter (SSC) with the voltage set at 474V with an amplification gain of 1.07. The fluorescent detectors FL2 was set at 449V with the amplification gain set at 1.32.

Cell and particle debris were electronically gated from the analysis on basis of scatter properties. In all the experiments at least 20,000 particles or cells were analyzed. All the experiments were performed in triplicate. The results are presented as mean fluorescence intensity of intact particles or viable cells only. Data analysis was carried out with CellQuest software (BD Biosciences).

Fluorescent Microscopy

Fluorescent imaging of particles was performed with a Nikon Eclipse TE2000-E with a DQC-FS Nikon CCD Camera kept at −30.1° C. All the samples were mounted immediately before the analysis and the images acquired with a 63× immersion oil objective. The microscope settings were kept constant throughout all the experiments. Numerical Aperture was set at 1.4, Refractive Index at 1.515, Exposure Time at 500 ms, Readout Speed at 10 MHz and Conversion Gain at 1/6×. The images were analyzed and measured with the NIS Elements AR 2.3 Software.

Results

Antibody Conjugation

The total number of particles used for conjugating APTES modified particles with the anti-VEGFR2 was ~7.03×10⁶. Two different amounts of anti-VEGFR2 were used for the conjugation as listed in Table 3 below.

TABLE 3

Amount of anti-VEGFR2 added to particles

| Particles ID | Anti-VEGFR2 added (µg) | Anti-VEGFR2 per $10^6$ particles (µg) |
|---|---|---|
| APTES1 | 2.04 | 0.29 |
| APTES2 | 0.407 | 0.058 |

In a different experiment, after conjugation, the particles were washed and centrifuged in phosphate buffer containing 0.5% Triton X-100 6 times followed by 4 washes in plain phosphate buffer and then read on the plate reader. Two different amounts of anti-VEGFR2 were used for the conjugation as listed in Table 4 below.

TABLE 4

Amount of anti-VEGFR2 conjugated to particles as detected by plate reader based on fluorescence assay of the anti-VEGFR2.

| Particles ID | No. of particles | Amt. of Anti-VEGFR2 (µg) | Anti-VEGFR2 per $10^6$ particles (µg) |
|---|---|---|---|
| APTES1 | $7.42 \times 10^5$ | 0.065 | 0.088 |
| APTES2 | $7.42 \times 10^5$ | 0.022 | 0.03 |

As indicated by Table 4, there was a significant reduction in the number of particles in all the cases during the conjugation. This might be due to losses incurred during the numerous washing steps involved in removing unbound antibody from the solution.

TABLE 5

Zeta Potential of microparticles and nanoparticles used in loading experiments

| Particle | Size of nanopores (nm) | Zeta potential (mV) | Buffer conidition at pH~7.3 |
|---|---|---|---|
| LP oxidized Si | 20-40 | −10.1 | 20 mM Tris |
| | | 1.31 | 200 mM Tris |
| LP APTES modified Si | 20-40 | 6.52 | 20 mM Tris |
| | | 5.19 | 200 mM Tris |

TABLE 5-continued

Zeta Potential of microparticles and nanoparticles used in loading experiments

| Particle | Size of nanopores (nm) | Zeta potential (mV) | Buffer conidition at pH~7.3 |
|---|---|---|---|
| LP MPTMS modified Si | 20-40 | −16.9 | 20 mM Tris |
| | | −6.17 | 200 mM Tris |
| SP oxidized Si | 5-7 | −11.15 | 20 mM Tris |
| | | −13 | 200 mM Tris |
| SP APTES modified Si | 5-7 | 6.42 | 20 mM Tris |
| | | −7.42 | 200 mM Tris |
| SP MPTMS modified Si | 5-7 | −18.3 | 20 mM Tris |
| | | −8.21 | 200 mM Tris |
| Amino qDots | NA | −1.21 | 20 mM Tris |
| | | 1.3 | 200 mM Tris |
| Carboxy qDots | NA | −32.8 | 20 mM Tris |
| | | −10.1 | 200 mM Tris |
| SWNTs | NA | −9.21 | 20 mM Tris |

Load and Release

Quantum dots (Qdots) and single-wall carbon nanotubes (SWNT) were used as second stage nanovectors for their distinct and excellent properties. Q-dots are light-emitting semiconductor nanocrystal (CdSe or CdTe), and many research has been conducted on in-vitro and in-vivo molecular and cellular imaging because of their high brightness, photostability and the capacity of multiplexed color coding. Q-dots were coated with hydrophilic polyethylene glycol (PEG) to increase biocompability. The zeta potential was -1mV for Amino-PEG Qdots in 20 mM Trs buffer, and −32.8 mV for carboxyl PEG Q-dots. The hydrodynamic size was measured by the diffusion coefficient of colloidals in solution using scattering light dynamic light scattering technique. Amino and Carboxyl Q-dots show similar hydrodynamics size (13 and 17 nm respectively).

SWNT is well-ordered hollow "rolled-up" structures, and has high aspect ratio, high surface area, high mechanical strength, ultra light weight, excellent chemical/thermal stability. Many protocols have been studied to functionalize the SWNT surface with peptides, proteins and drugs. In this study, SWNT was of diameter 2-4 nm and lengths between 30 and 100 nm, the surface was functionalized with PEG-amine, providing solubility in water and physiological saline and further linked to FITC for fluorescent imaging. The zeta potential measurement shows −9.2 mV in 20 nM TRIS buffer.

The effect of Tris concentration on the loading of quantum dots in large pores particles was first investigated. Tris was selected as a buffering agent because, it may give the highest stability to the quantum dots (Q-dots) compared to other buffering agents. The mean fluorescence of Q-dots loaded particles was studied as a function of Tris concentration. The fluorescence signal on the particles increased as the Tris concentration increases. The concentration of 200 mM Tris gave the best effect in terms of loading and was therefore selected for all the subsequent experiments.

The loading capacity of "large porous" silicon particles was evaluated by using "small porous" silicon particles as the control. The hydrodynamic size of Q-dots is 13-15 nm, and should not be able to get into the small pores (<5 nm) but stay on their surface. The concentration effect of Q-dots for the loading was performed by changing the amount of Q-dots from 10 picomolar to 2 micromolar and incubating all the reactions in the same final volume (20 µl ). Sample's loading was analyzed at FACS and the quantum dot concentration of 2 µM resulted in the highest level of loading and therefore used for all the subsequent experiments.

The loading time/dynamics of particles with Q-dots were studied by different incubation time (15 min, 30 min and 60 min). The loading of Q-dots in the particles was a very fast process that reached its maximum within 15 min. After that, the fluorescence signal drops slowly with time as shown in FIG. 21, Panels a-d.

The surface properties of particles also proved to be important in the loading kinetics. As shown in FIG. 21, Panels a-d, carboxyl PEG Q-dots showed little loading into the oxidized particles. This may be attributed to the electrostatic force since both particles were negatively charged. When the surface of the silicon particles was modified with amino groups (APTES), the zeta potential became positive (+5~+6 mV) as shown in Table 5. The loading of carboxyl Q-dots significantly increased into APTES treated particles. The charge of amino-PEG Q-dots is almost neutral (zeta potential −1~+1 mV), and the APTES treatment of silicon particles had only a minor impact on the loading (zeta potential changed from −11 mV to +6 mV).

The kinetics of amino quantum dots release from LP oxidized particles were exponential like with a 33% decrease of the amount of loaded nanoparticles after 20 minutes and of 67.5% after 45 minutes. After 20 hours only a residual 1% of the initial fluorescence was found associated to the particles demonstrating that all the quantum dots could be released from the nanoporous silicon particles.

Fluorescence Quenching

Figure 6A:
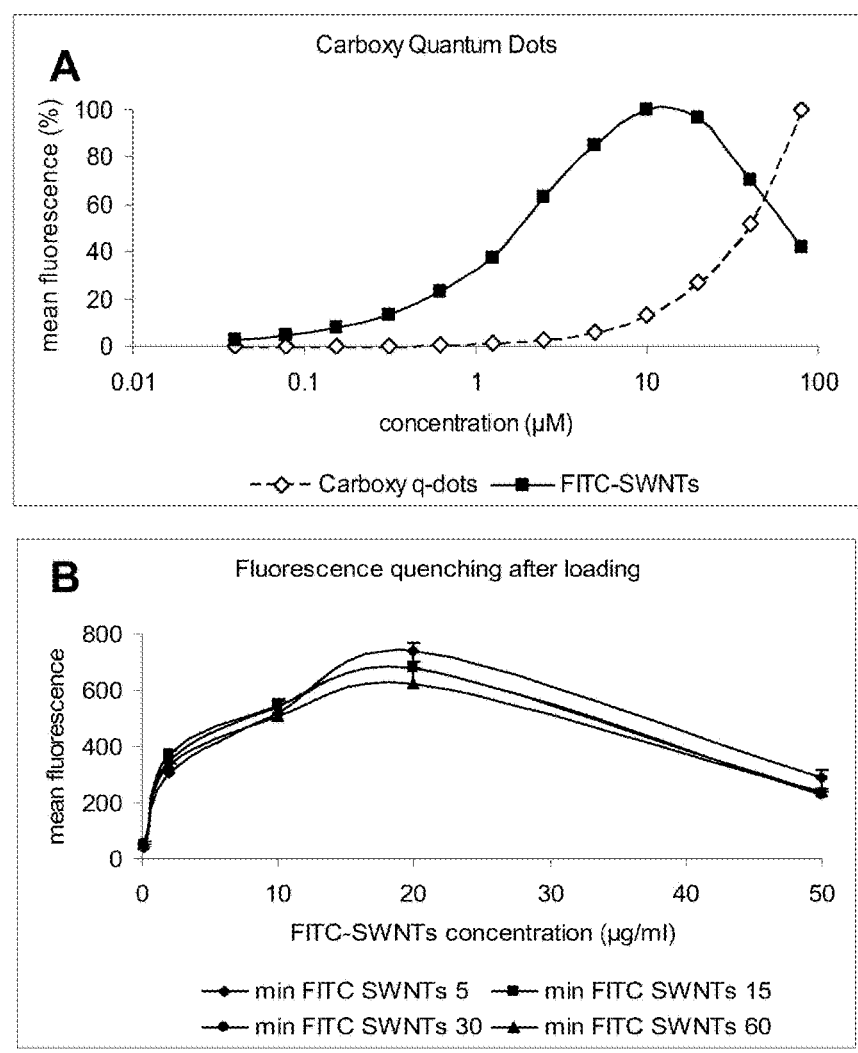
FIG. 6A, Panel A, presents the concentration effect of loading carboxy modified quantum dots and FITC-conjugated single wall carbon nanotubes (SWNTs). Y axis in Panel A reads mean fluorescence (%).
Figure 20:
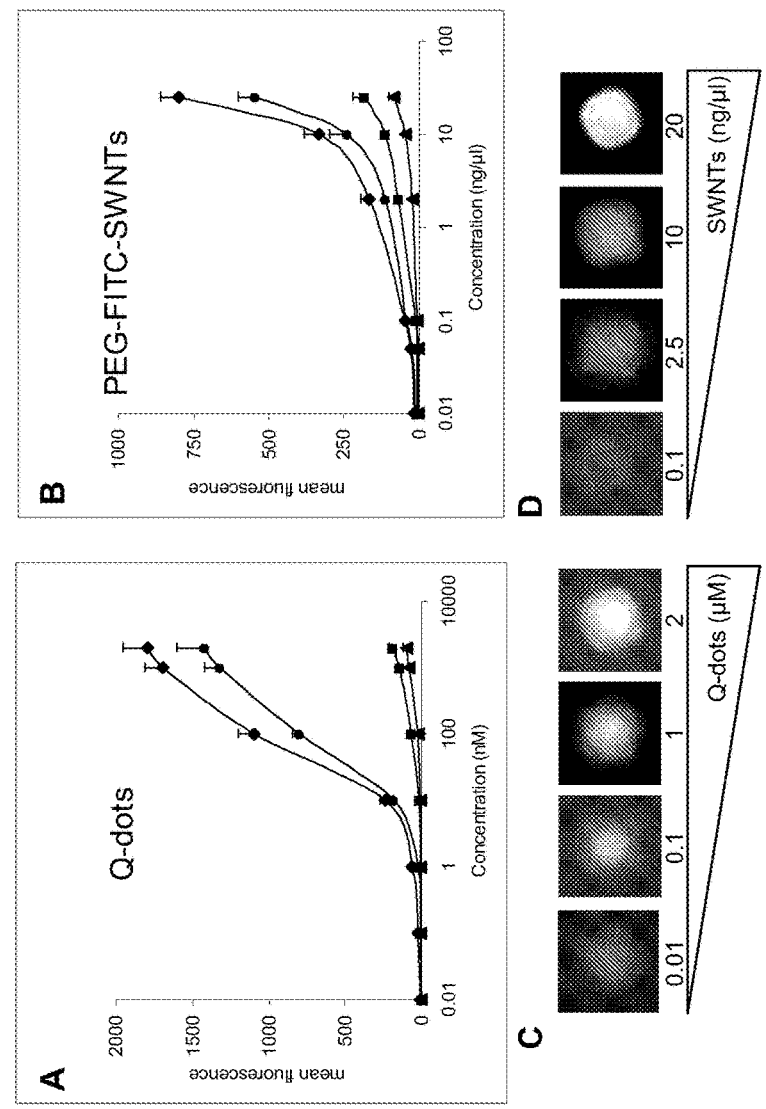
FIG. 20 presents results of flow cytometric and fluorescence microscopy analysis of loading of fluorescently labeled Q-dots and PEG-FITC-SWNTs into nanoporous silicon particles. An increase in the amount of nanoparticles in the loading solution resulted in an increase in the mean fluorescence of silicon particles (.diamond-solid. LP APTES+Carboxyl Q-dots LP oxidized+Amino Q-dots .box-solid. SP APTES+Carboxyl Q-dots .tangle-solidup. SP oxidized+Amino Q-dots) measured by flow cytometry (Panels A and B). Fluorescent microscopy (Panels C and D) confirmed that the fluorescence associated to first stage particle was dimmer when the amount of nanoparticles used was lower. Y axis in Panels A and B reads mean fluorescence.
Figure 21A:
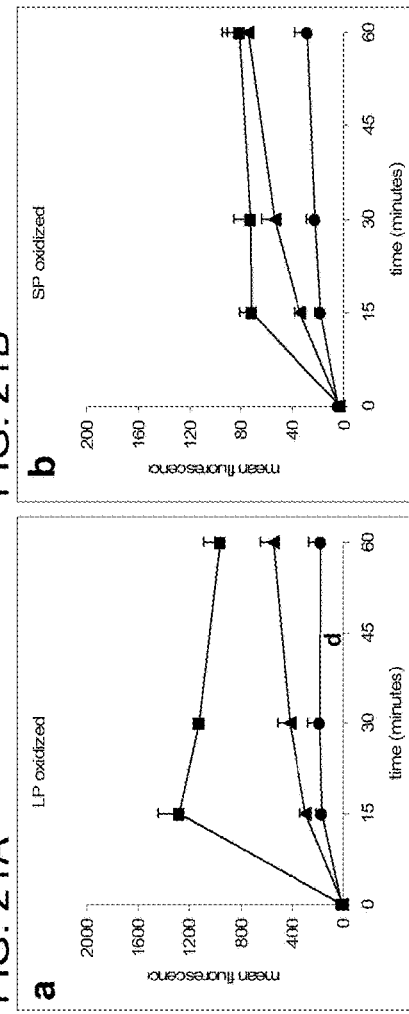
FIGS. 21A-21H present time dependent loading and releasing of second stage particles in nanoporous silicon first stage particles. Four different types of nanoporous silicon first stage particles (LP oxidized (A), LP APTES (B), SP oxidized (C), and SP APTES (D) were loaded with different second stage nanoparticles (Carboxyl q-dots, .box-solid. Amino q-dots, tangle-solidup. PEG-FITC-SWNTs) and their fluorescence measured by flow cytometry. Histograms in 21E-21H represent a percentage of second stage particles released from the first stage silicon particles with the passage of time.
Figure 21B:
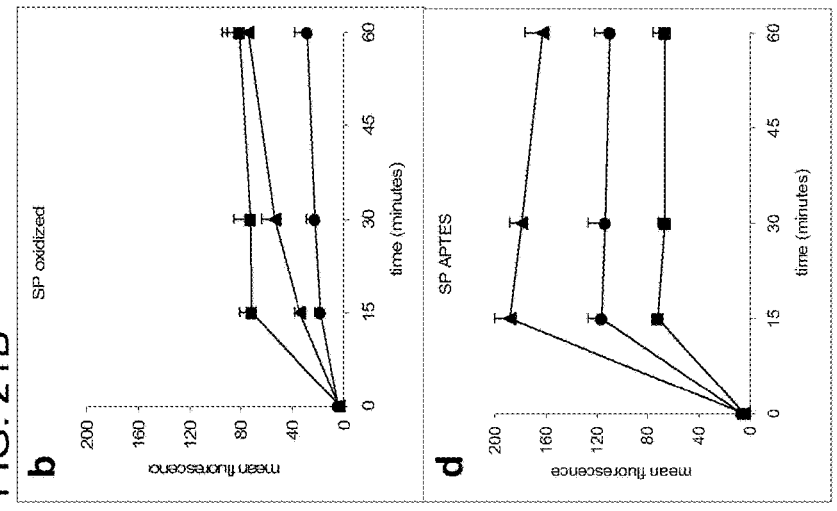
Figure 21C:
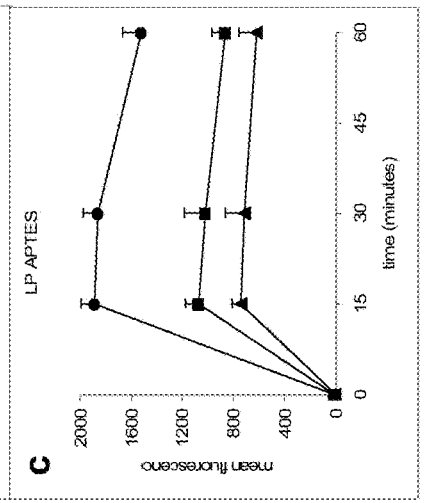
Figure 21D:
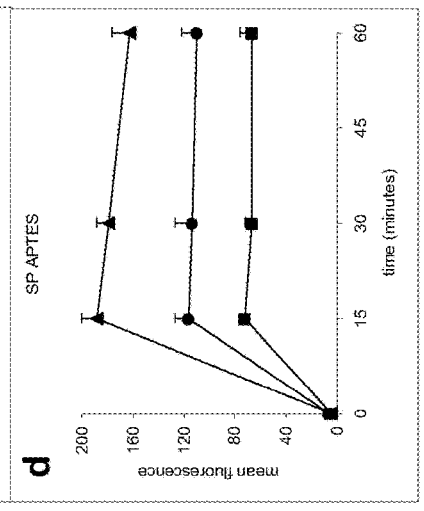
Figure 21E:
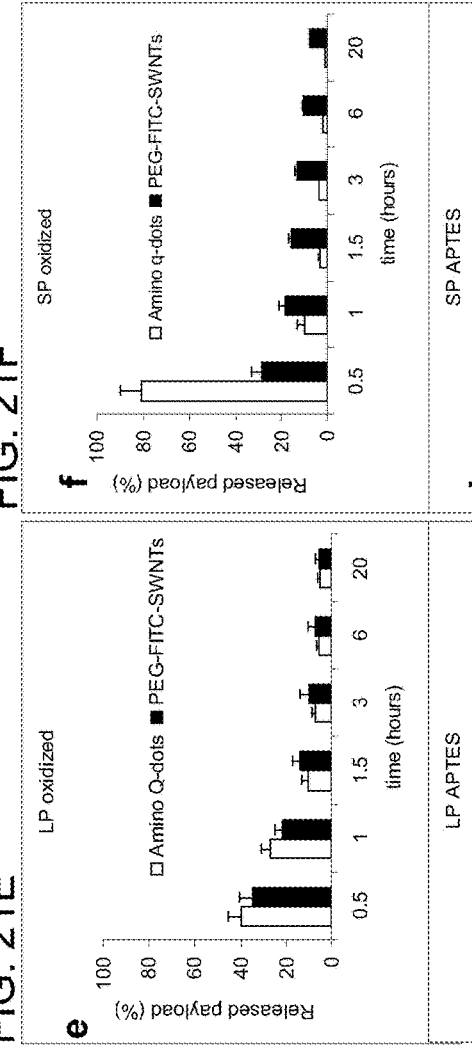
Figure 21F:
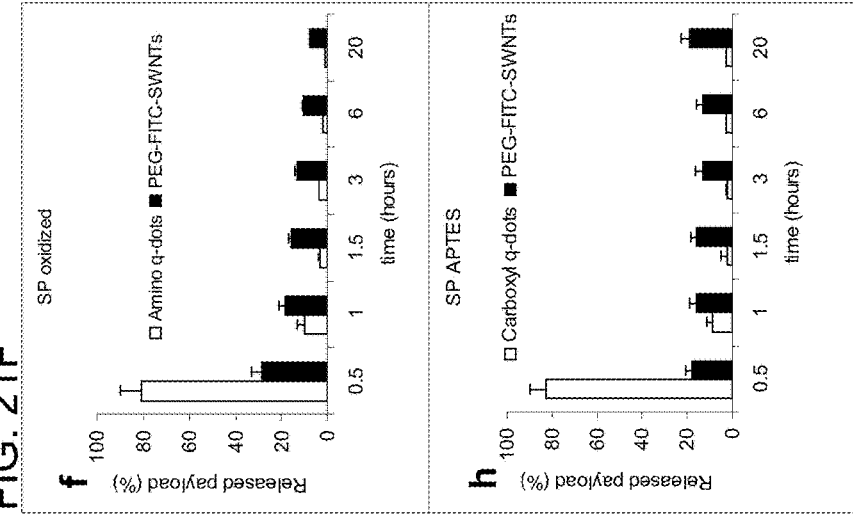
Figure 21G:
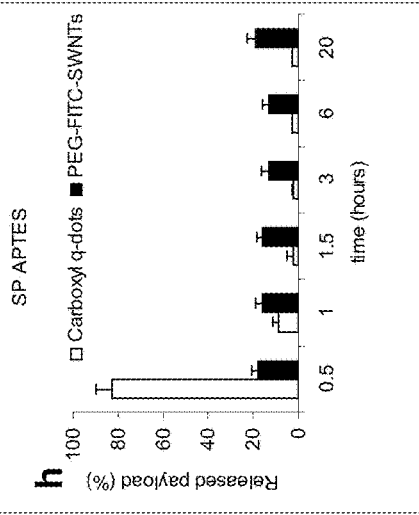
Figure 21H:
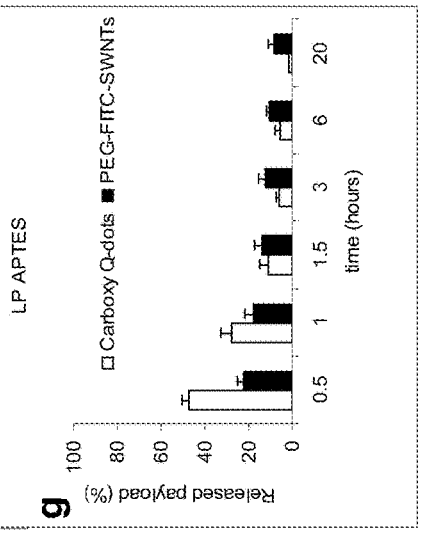

The fluorescence of a solution containing 35 µg/ml of FITC conjugated single wall carbon nanotubes (FITC-SWNTs) and of a serial dilution of them (ranging from 1:2 to 1:2048) in milliq pure water was measured (FIG. 6A, Panel A). The fluorescence values of the first 3 and more concentrated samples (respectively 35, 17.5 and 8.725 µg/ml) were lower than the values of less concentrated solution. This is a phenomenon known as fluorescence quenching. As a control the same readings were performed with a series of solutions of carboxy pegylated quantum dots ranging from 8 µM to 4 nM that showed a linear decrease of the fluorescence value along with the dilution. The fluorescence quenching dynamics in the loading of APTES modified LP particles with FITC-SWNTs was evaluated. The experiments were performed as previously described. The profiles of the curves suggested that the loading of the higher amount of FITC-SWNTs induced fluorescence quenching thus resulting in decreased fluorescence of the silicon particles. The concentration of 20 µg/ml was selected for all the subsequent experiments (FIG. 6A, Panel B and FIG. 20, Panel B).

Figure 6B:
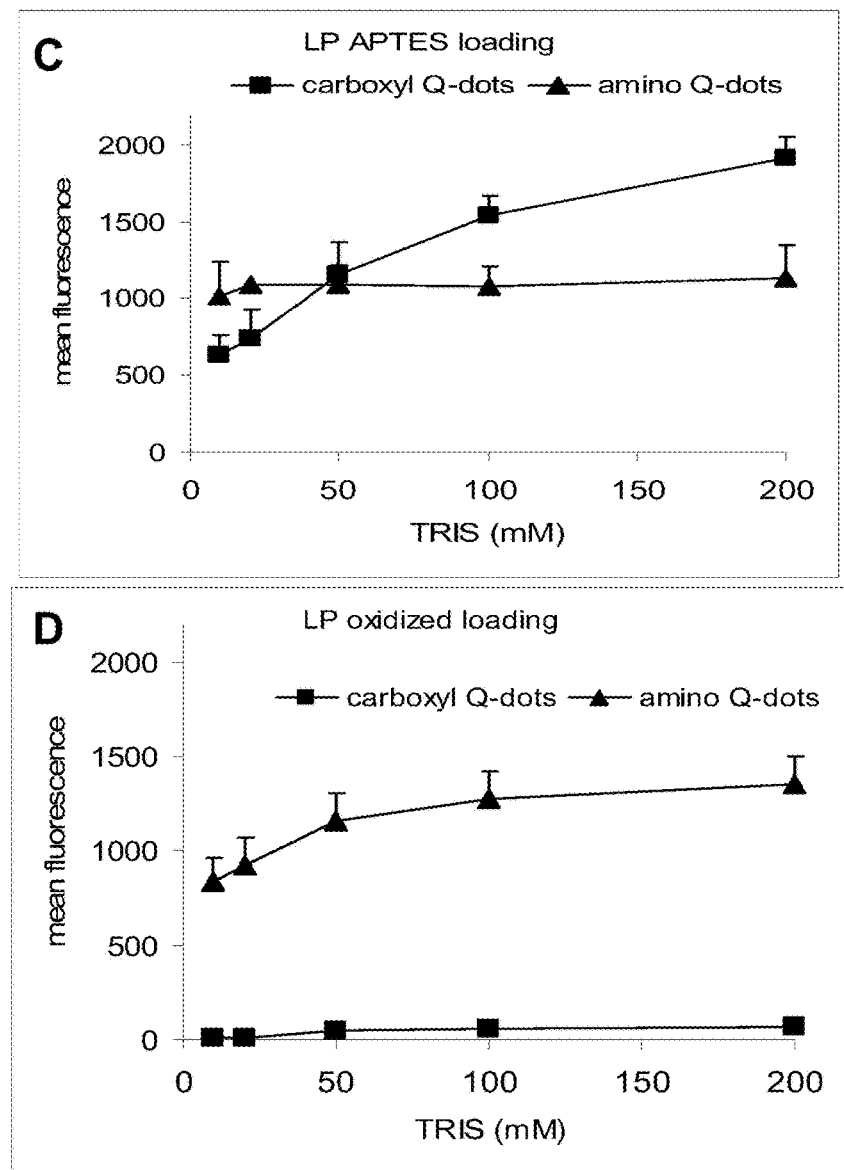
FIG. 6B relates to optimization of chemical condition for loading of second stage particles into nanoporous silicon particles. Nanoporous silicon particles were mixed with second stage nanoparticles (Q-dots in FIG. 6B, Panel C and Panel D; PEG-FITC-SWNTs in Panel E and Panel F) in the presence of increasing concentration of TRIS. High concentration of TRIS helped in increasing the amount of Q-dots loaded into the first stage silicon particles (Panel C and Panel D). On the contrary, loading efficiency of PEG-FITC-SWNTs reached its peak at 20 Mm TRIS and then decreased at higher TRIS concentrations, Panel E and Panel F. Y axis in Panels B-F reads mean fluorescence.

The effect of Tris concentration on the loading of PEG-FITC-SWNTs and q-dots in large pores particles was also investigated, see FIG. 6B, Panels C-F. Panel E and Panel F show the mean fluorescence of PEG-FITC-SWNTs loaded particles in LP APTES modified and LP oxidized silicon particles as a function of Tris concentration. The fluorescence signal on the particles decreased as the Tris concentration increased. The concentration of 20 mM Tris gave the best effect in terms of loading and was therefore selected for all the subsequent experiments.

Carbon Nanotubes Loading

The dynamics of the loading of both oxidized and APTES modified LP and SP particles with FITC-SWNTs was evaluated. The experiments were performed as previously described using 20 µg/ml of fluorescent nanoparticles (see FIG. 4, Panels A-D). In this experimental setting, the loading time dynamics were fast for the LP APTES particles that showed a similar decrease at later time points (FIG. 4, Panel B, and FIG. 21). A different kinetic was observed for the LP oxidized particles loading that increased during the whole duration of the experiment and reached its maximum at the 60 minutes time point (FIG. 4, Panel A, and FIG. 21).

The same loading patterns were occurring during the loading of small pore particles (SP). The APTES modified particles loaded very quickly and then lost some of their associated fluorescence through time (FIG. 4, Panel D, and FIG. 21), while the oxidized SP loading increased over time as happened with the LP particles suggesting that APTES modification played a crucial role in the loading process (FIG. 4, Panel C, and FIG. 21).

Figure 7:
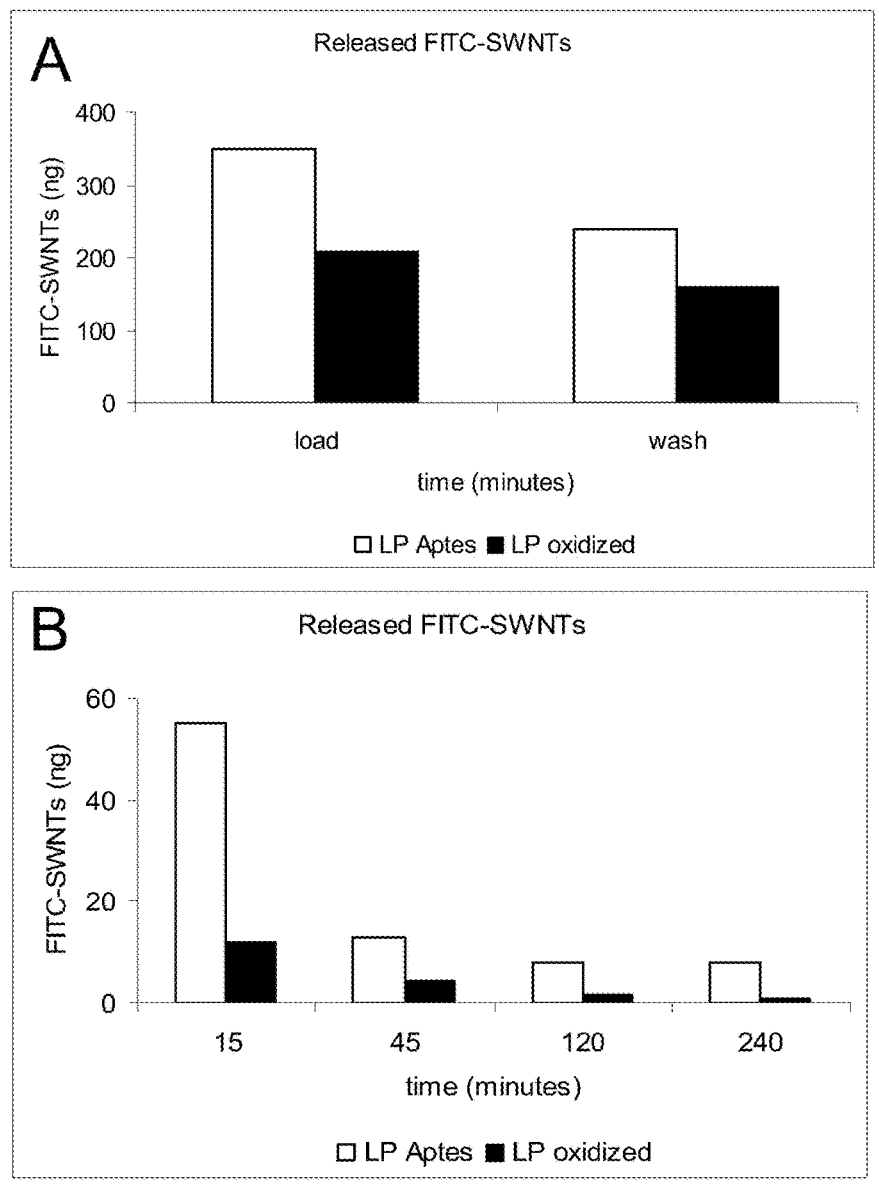
FIG. 7 demonstrates data for loading and release respectively FITC conjugated with SWNT second stage particles into LP nanoporous silicon first stage particles. Panel A presents load columns, corresponding to the amount of FITC-SWNT initially loaded in the nanoporous silicon first stage particles after exposure to a FITC-SWNT solution prior to washing. Wash columns in Panel A corresponds to the amount of FITC-SWNT after washing the first stage particles. The actual load of the FITC-SWNT in the first stage particles is the amount of FITC-SWNT retained in the first stage particles after washing, i.e., a difference between the respective values in the load column and in the wash column. Panel B shows data for release of FITC-SWNT from the first stage particles over time. The total amount of FITC-SWNT released from the first stage particles over time, i.e., a sum of all the columns in Panel B, substantially matches the difference between respective load and wash columns in Panel A. Y axis in Panels A and B reads amount of FITC-SWNTs (ng).

The kinetics of PEG-FITC-SWNTs release from LP oxidized particles were exponential like in the first time points. The release slowed down in later time points. After 20 hours only a residual 20% of the initial fluorescence was found associated to the particles suggesting that some of the payload could be retained into the nanoporous silicon particles (FIG. 7B and FIG. 21)

Nanoliposomes also loaded into LP particles with the same dynamics as described above. The fluorescence associated with the Silicon particles were visualized by means of fluorescence microscopy (FIG. 8A, Panels A and B, FIG. 8B, Panels E and F).

Degradation

Porous Silicon (PSi) is known to be fully biodegradable (Mayne 2000; Low, Williams et al. 2006) and biocompatible (Canham 1995). The oxidation process, that was performed according with protocols already described for Silicon wafers (Canham 1997), introduced hydroxil groups (OH) on the exposed Silicon surface and these groups, in the presence of water, are subjected to hydrolysis thus converting solid Silicon into highly soluble Silicic acid.

SEM

Figure 10A:
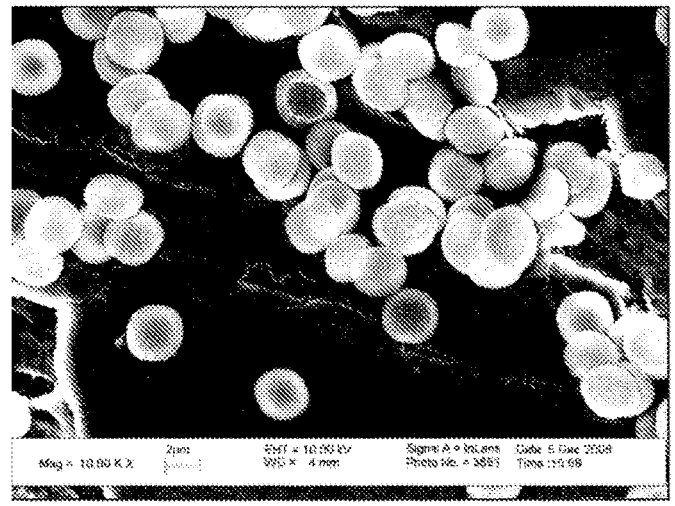
Figure 10B:
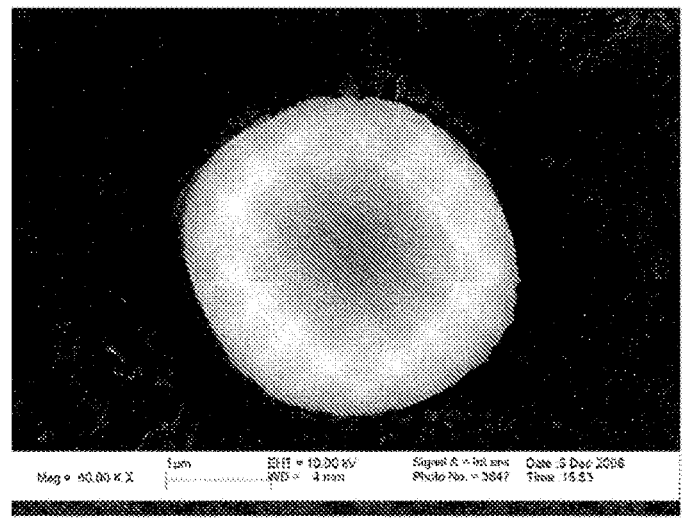
Figure 11A:
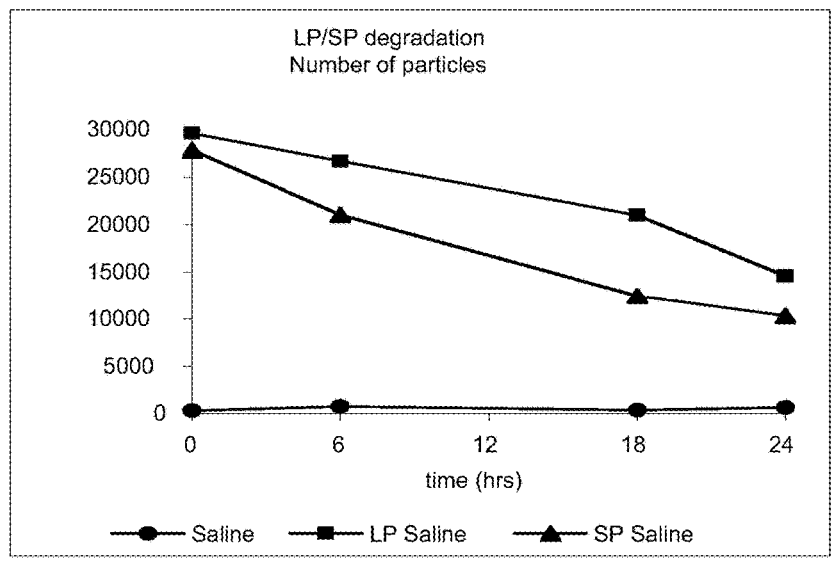
FIGS. 11A-11D demonstrate degradation of nanoporous silicon particles measured using Z2 Coulter.RTM. Particle Counter. Y axis in 11A and 11B reads number of particles. Y axis in 11C and 11D reads volume of particles.
Figure 11B:
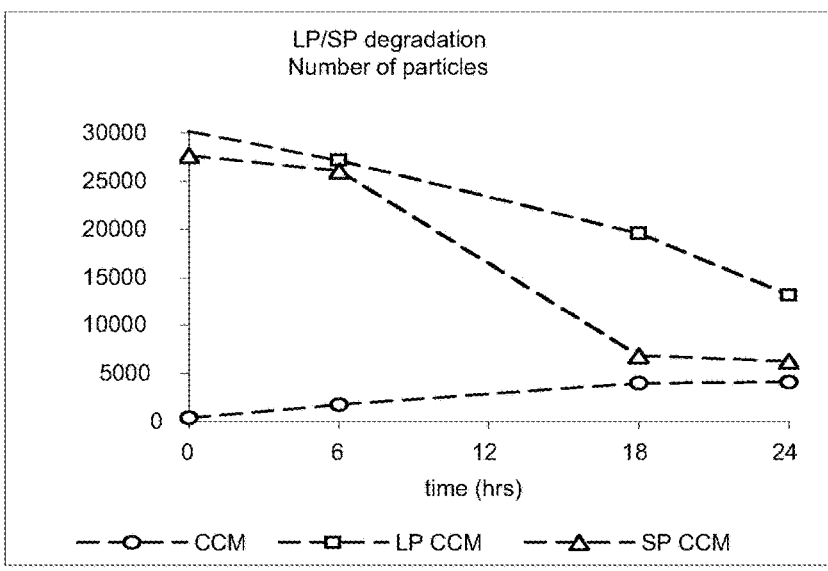
Figure 11C:
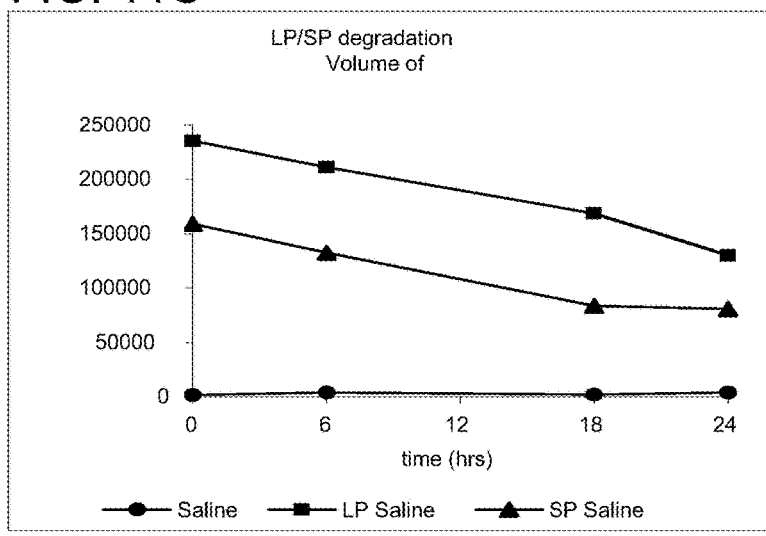
Figure 11D:
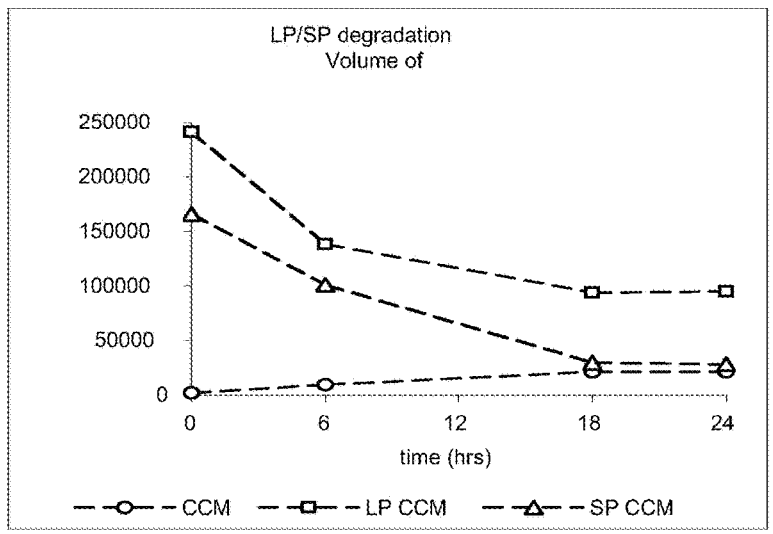

The study of the modifications in the size, shape and overall aspect of the particles was performed by Scanning Electron Microscopy (SEM) (FIGS. 9 and 10). The images showed that the particles degraded along time starting from the areas with high porosity and then degradation spread to particles edges where the porosity is lower and the size of the pores smaller. It is suprising to notice that the overall shape of the particles remained almost intact until the end of the degradation process occurred. Although the present inventions arenot limited by a theory of their operation, this surprising observation may be explained by the fact that corrosion of oxidized Silicon surfaces progressively consumed the walls in between the pores thus creating bugs and holes in the center of the particles. The same process took more time to dissolve the sides of the particles, where the number of pores is smaller and the walls between the pores are thicker.

Z2 Coulter

The characterization of nanoporous Silicon particles degradation was performed through several techniques. The measurement of a decrease in the number of particles and in their volume was performed with Z2 Coulter® Particle Counter and Size Analyzer (Beckman Coulter). The particles were kept for 24 hours in a rotating wheel (8 rpm) at 37° C. in two different solution: TRIS 2.5 mM, 0.9% NaCl at pH7.3 (Saline) and Cell Culture Media with 10% FBS (CCM). To understand, if the size of the pores had a role in the degradation kinetics, both Silicon particles with smaller pores of 7-10 (SP) nanometers and particles with larger pores of 20-30 nanometers (LP) were used.

The particles incubated in Saline did not show any significant decrease in their median size distribution, either in the case of LP and in the SP. On the contrary, their number went progressively down throughout time (FIG. 11, Panel A). These results combined together may mean an overall loss of Silicon particles mass of 50% or more for both LP and SP particles at 24hrs, as indicated in FIG. 11, Panel C.

In the experiment performed with particles incubated in CCM, a decrease in both their median size and number (FIG. 11, Panel B). These results combined together indicated a loss of particles mass of 60% for the LP particles and more than 90% for SP particles.

ICP

Figure 12A:
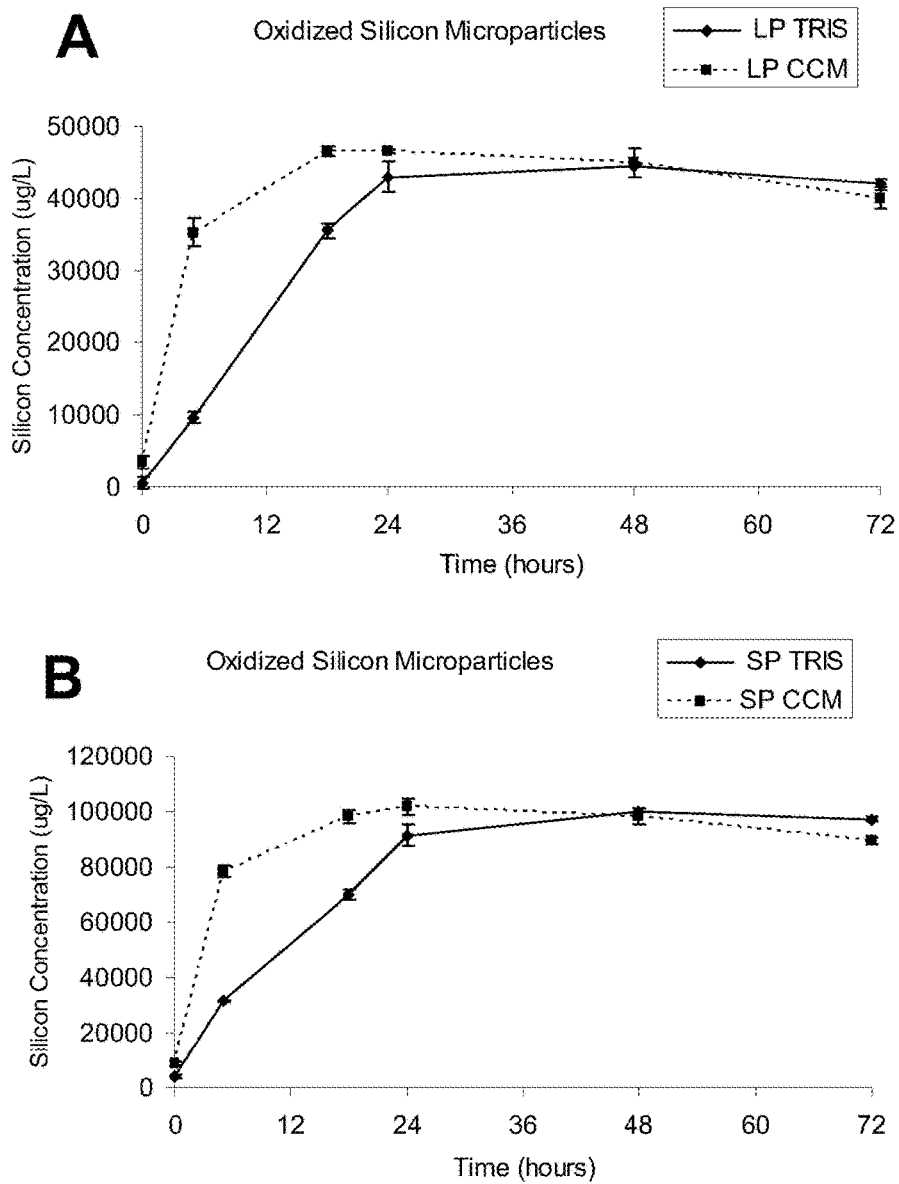
FIGS. 12A-B demonstrate degradation of nanoporous silicon particles measured using Inductive Coupled Plasma—Atomic Emission Spectrometry.
Figure 12B:
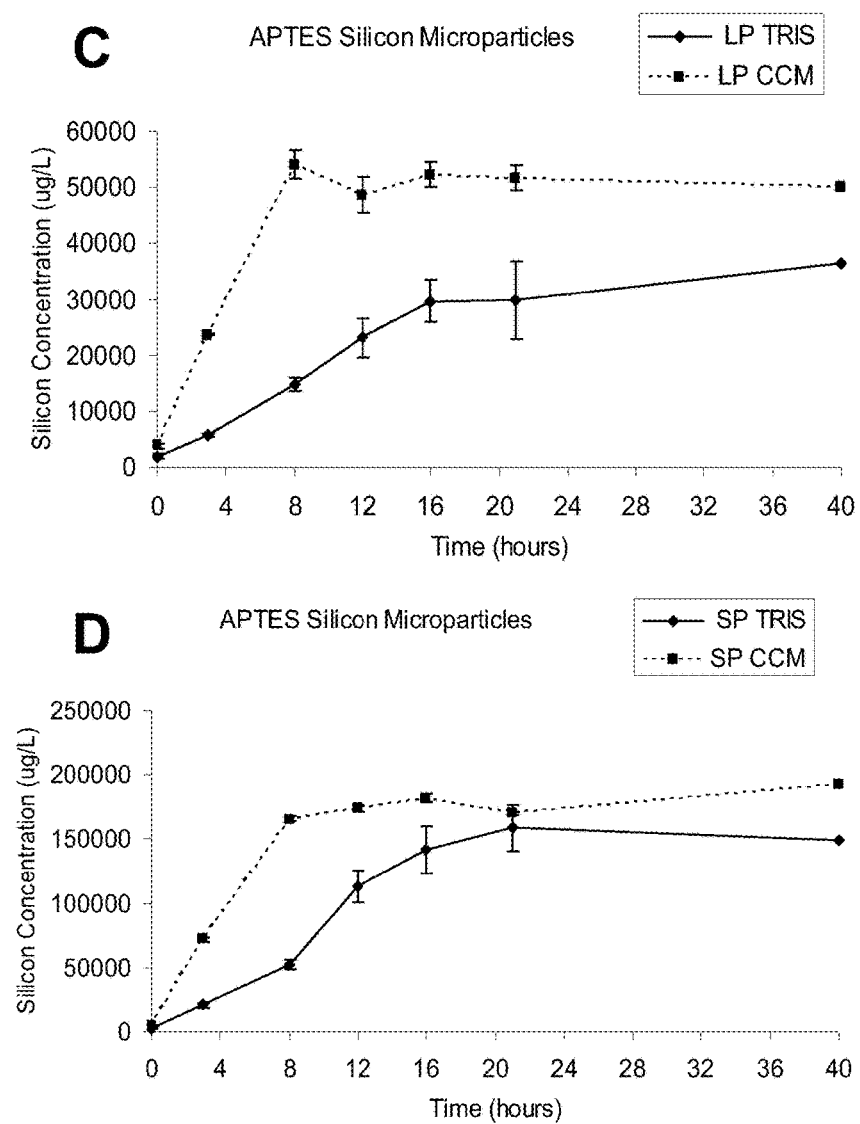

The readings at the ICP showed a linear increase in the amount of silicon present after degradation. These data confirmed the ability of the ICP-AES method for verification of degradation. The data were regular, with low standard deviations, and had a strong correlation with the Z2 readings of particles count and size during the test. The increased degradation that occurred in cell culture media as opposed to TRIS buffer suggested high biodegradability of these particles in cell culture conditions (FIG. 12A, Panels A-B and FIG. 12B, Panels C-D).

Biocompatbility

Silicon nanoporous particles induced cell toxicity by means of Lactate Dehydrogenase (LDH) toxicity assay (Biovision Inc.), cell proliferation by means of MTT assay (Promega) and apoptosis and cell cycle by means of Propidium Iodide staining.

Bright Field Microscopy

Figure 13:
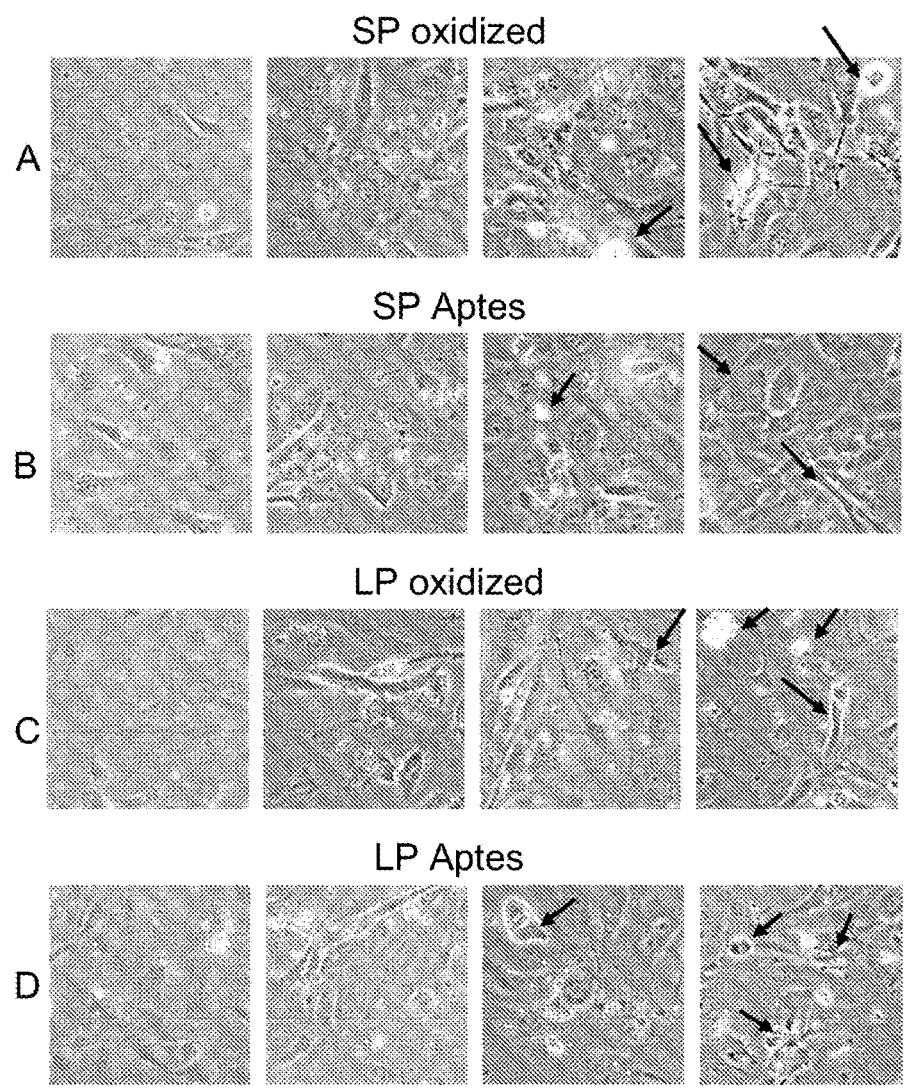
FIG. 13 demonstrates biocompatability of nanoporous silicon first stage particles by presenting bright field microscopy images of selected nanoporous silicon particles and Human Umbilical Vein Endothelial Cells (HUVEC) cells. In particular, Panel A demonstrates images for small pore oxidized silicon nanoparticles; Panel B demonstrates images for small pore APTES modified silicon nanoparticles; Panel C demonstrates images for large pore oxidized silicon nanoparticles; Panel D demonstrates images for large pore APTES modified silicon nanoparticles. In each Panel A-D, from left to right: first image day 0 (2 hrs after particles addition), second image day 1; third image day 2; fourth image day 3.

Cells grown in the presence of porous Silicon particles did not show any significant or abnormal type of morphological change (FIG. 13, Panels A-D) during time. The cells were at 50% confluency after 12 hours and they reached almost 100% confluency after 24 hours. Some signs of apoptosis or, more generally, of cell death were visible at 48 hours and even more at 72 hours (bright, rounded, reflectant cells or cells with large, multilobular nuclei or with high narrowing of the cell body) as indicated by the white arrows in the FIG. 13, Panels A-D. This was mainly due to the fact that the cells had already reached confluency and could not find any space to grow further and thus underwent some processes of cell degradation.

LDH Toxicity Assay

LDH is a cytoplasmic enzyme that is released into the cytoplasm upon cell lysis. The LDH assay, therefore, is a measure of membrane integrity. The basis of the LDH assay are oxidization of lactate to pyruvate by LDH, pyruvate reaction with the tetrazolium salt to form formazan, and the spectrophotometrical detection of the water-soluble formazan. (Decker, T. & Lohmann Matthes, M. L. (1988) J. Immunol Methods 15:61-69; Korzeniewski, C. & Callewaert, D. M. (1983) J. Immunol Methods 64:313-320).

Figure 14A:
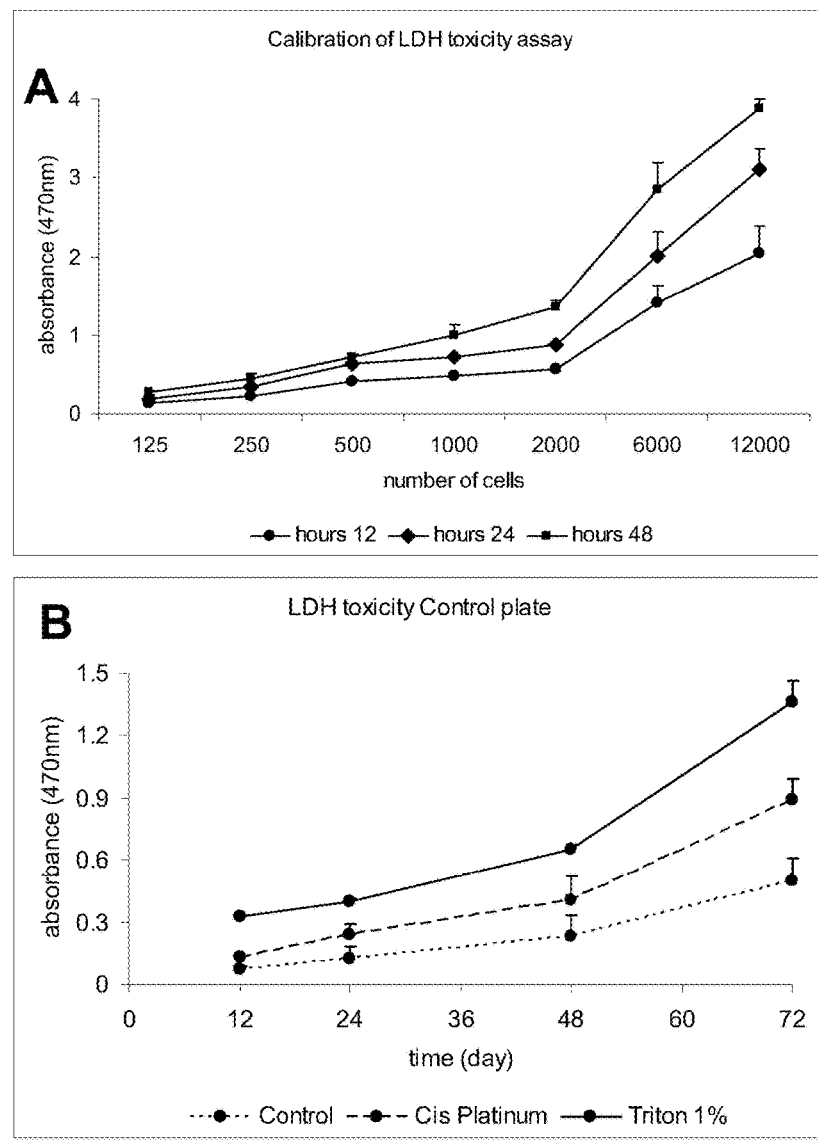
FIGS. 14A-B demonstrate biocompatibility of nanoporous silicon particles by presenting data for Lactate Dehydrogenase (LDH) toxicity assay on HUVEC cells incubated with nanoporous silicon nanoparticles. Y axis in Panels A-F reads absorbance at 490 nm.
Figure 14B:
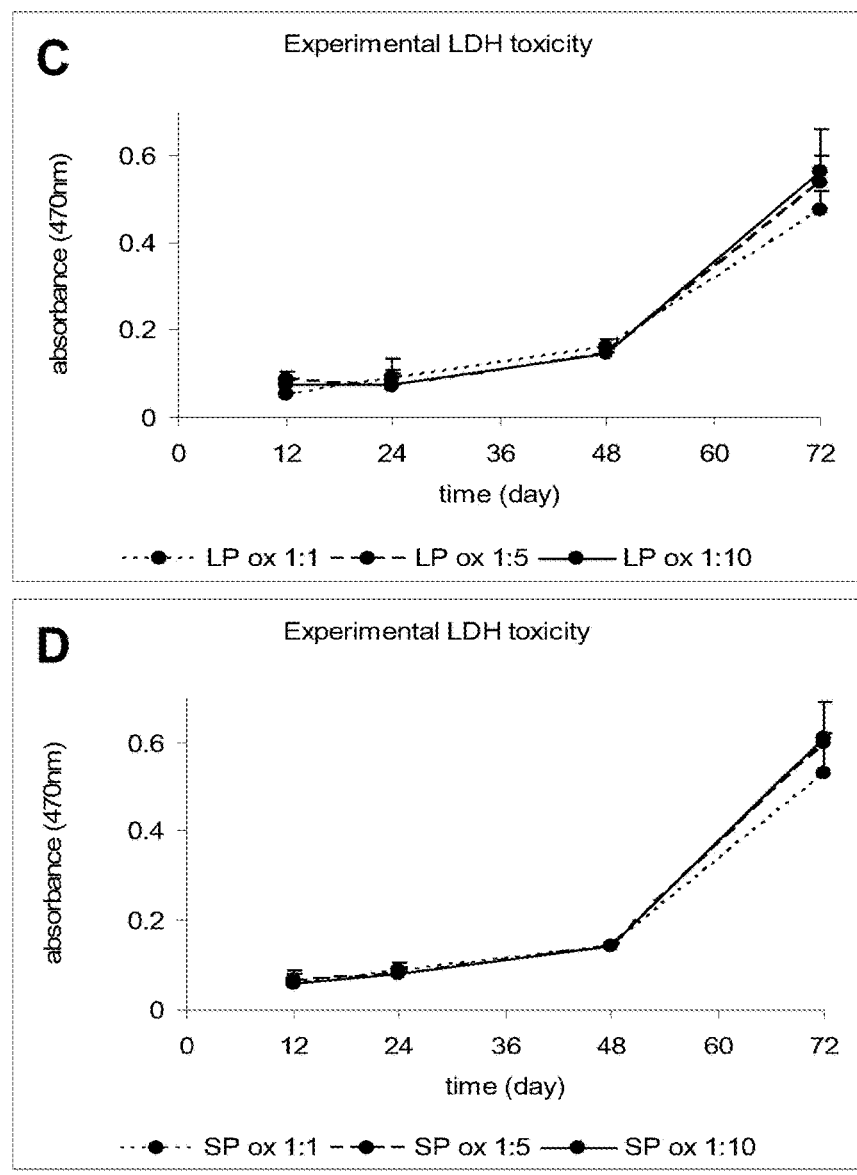

A toxicity calibration curve (FIG. 14A, Panel A) was made to correlate the absorbance values read at fluorimeter with the number of cells that were lysed by 1% Triton incubation. From this calibration curve, the amount of cells that were releasing the LDH enzyme during particles incubation was derived. At 12 and 24 hours, the toxicity signal was very low and could be mainly due to unbound cells that did not recover from trypsinization and seeding (background toxicity). This was confirmed by comparing the toxicity values coming from the experimental plates with those measured in the control plates (FIG. 14A, Panel B). The toxicity of HUVEC cells grown in the 96 well plates without any particles (positive control) showed at 72 hours a mean absorbance of 0.496 at 470nm. That was almost the same value as from cells incubated with a 1:1 ratio (0.507). At the higher cells:particles ratios (1:5 and 1:10) the mean values for toxicity were 0.55 and 0.57 respectively (FIG. 14A, Panel B and FIG. 14B, Panels C-F). The same toxicity pattern was observed in all the experimental conditions thus showing that porosity and surface chemistry did not either increased or decreased cell toxicity. All together these results did not suggest any massive toxicity due to exposition of cells to particles.

MTT Proliferation Assay

MTT is a yellow water-soluble tetrazolium dye that is reduced by live cells to a water insoluble purple formazan. The amount of formazan may be determined by solubilizing it in DMSO and measuring it spectrophotometrically. Comparisons between the spectra of treated and untreated cells may give a relative estimation of cytotoxicity. (Alley et al. (1988) Cancer Res. 48:589-601). A toxicity calibration curve (FIG. 15, Panel A) to correlate the absorbance values read at fluorimeter with the number of growing cells. From this calibration curve, the amount of cells that were metabolically active was derived.

Figure 15A:
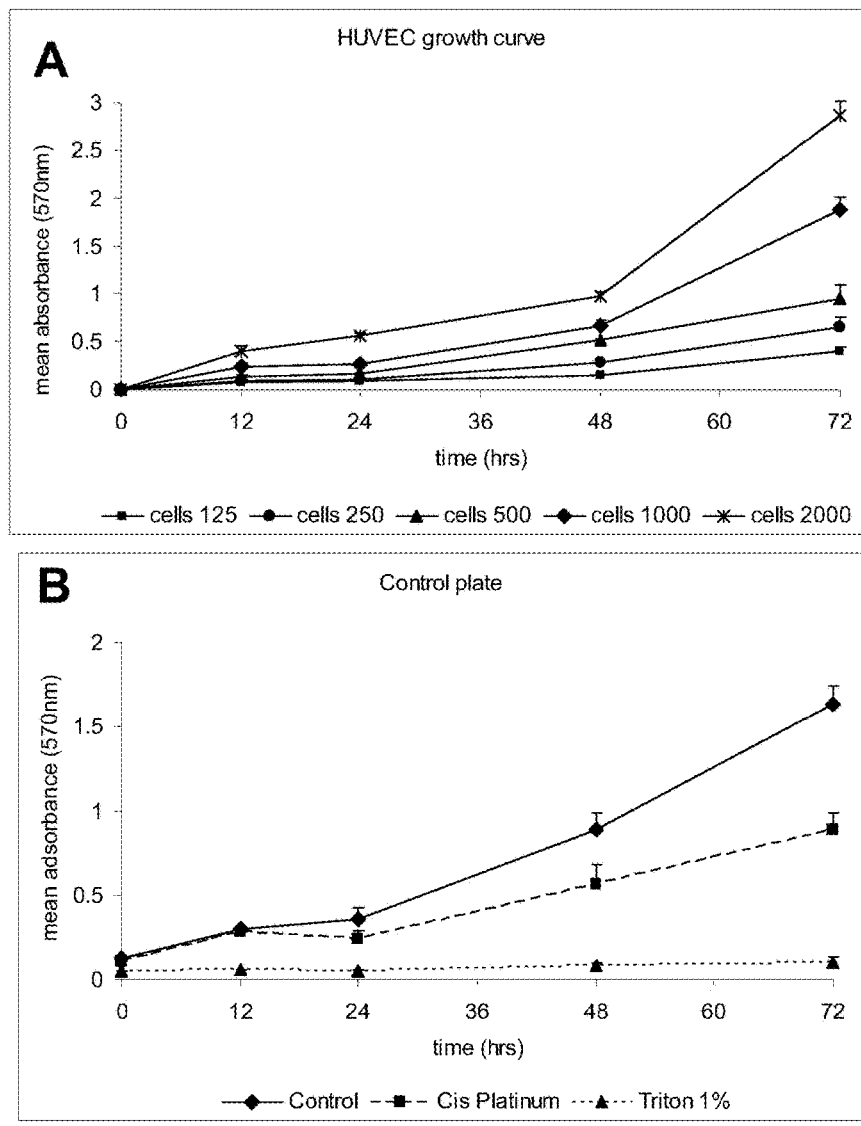
FIGS. 15A-B present data for MTT proliferation assay on HUVEC cells incubated with nanoporous silicon nanoparticles. Y axis in FIG. 15A, Panels A-B and FIG. 15B, Panels C-F reads absorbance at 570 nm.
Figure 15B:
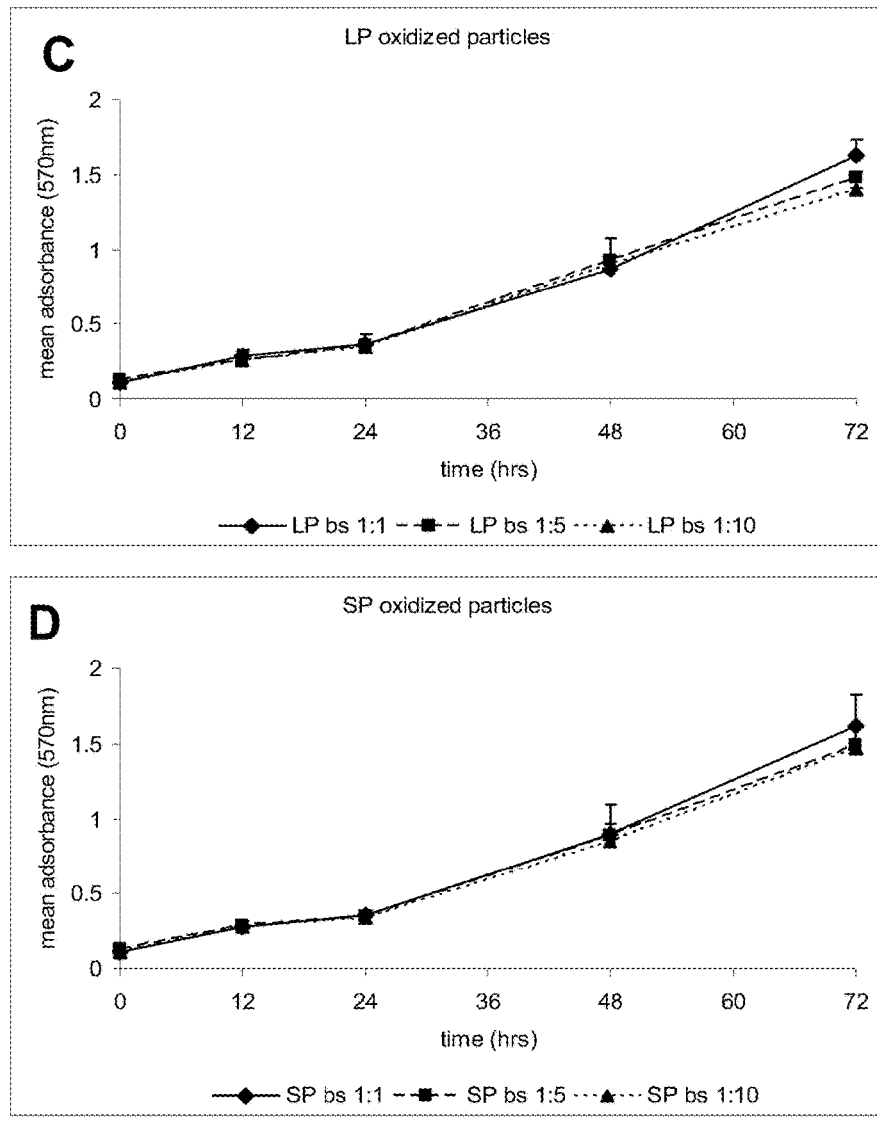
Figures 1, 16A:
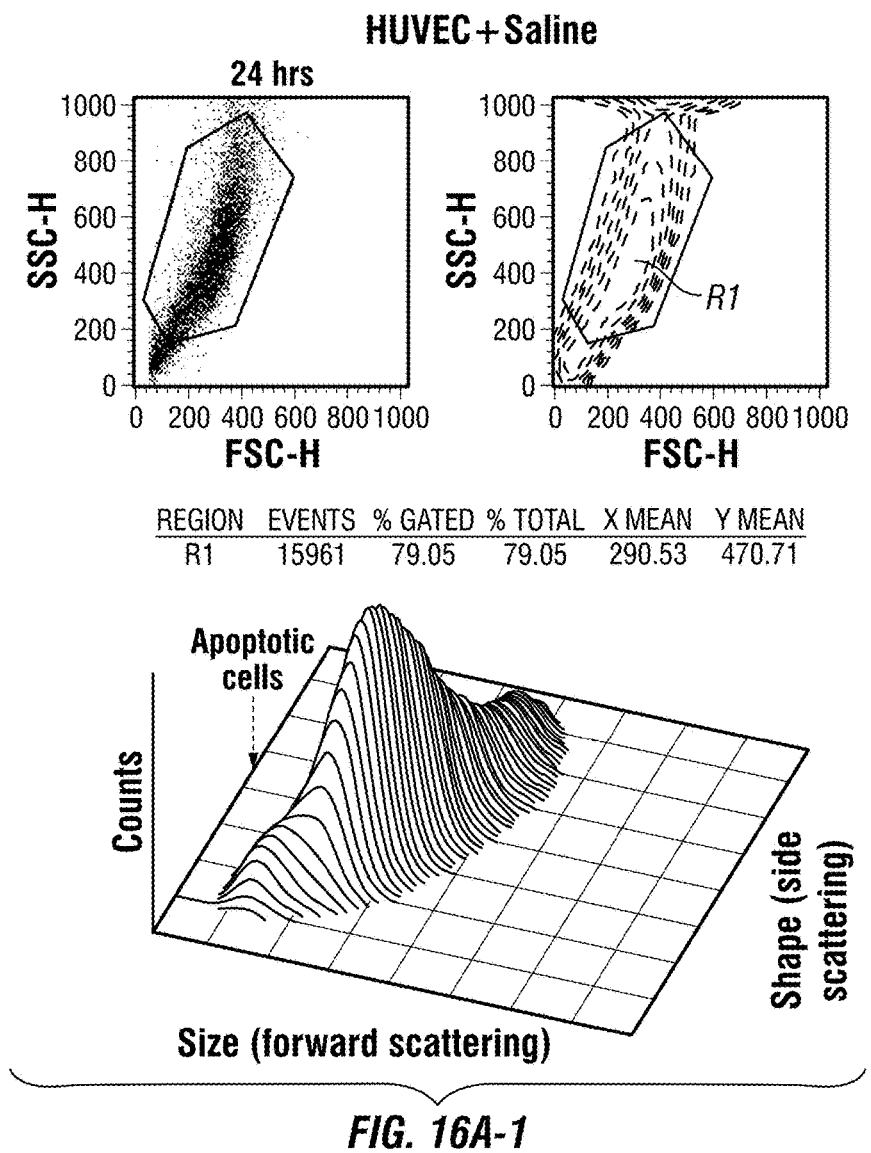
Figures 2, 16A:
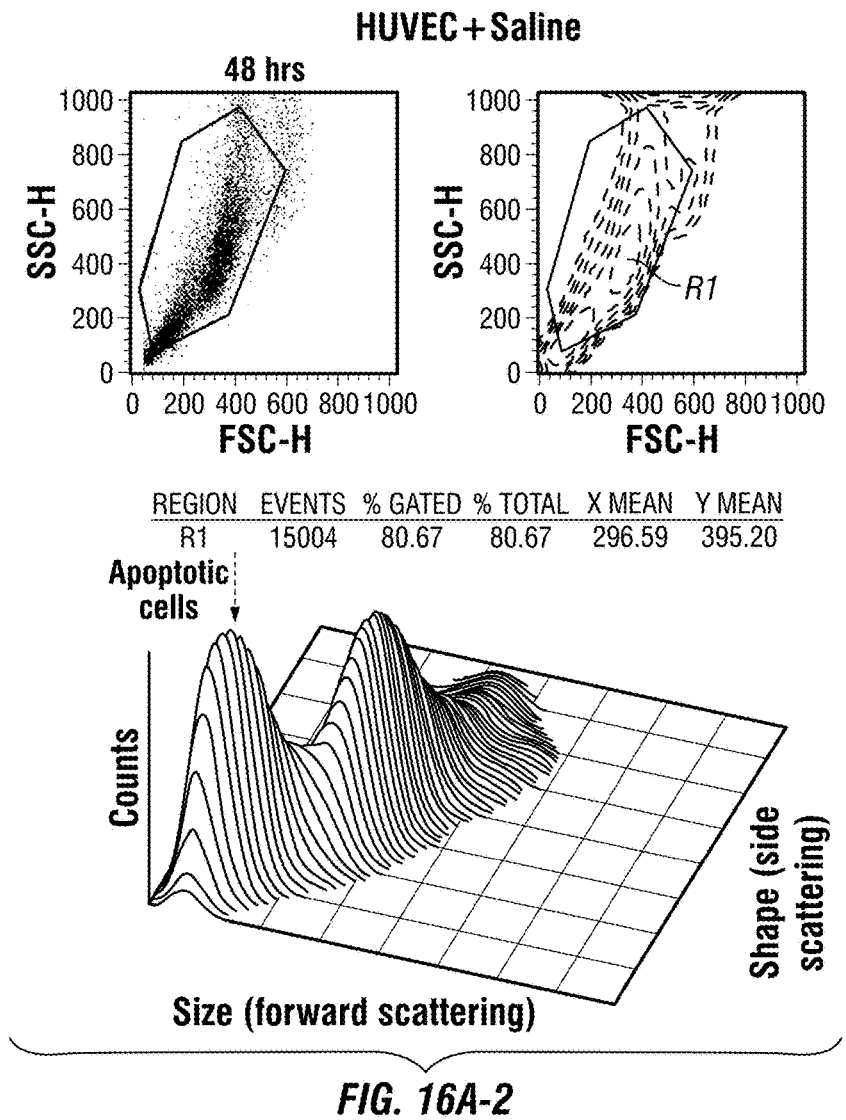
Figures 3, 16A:
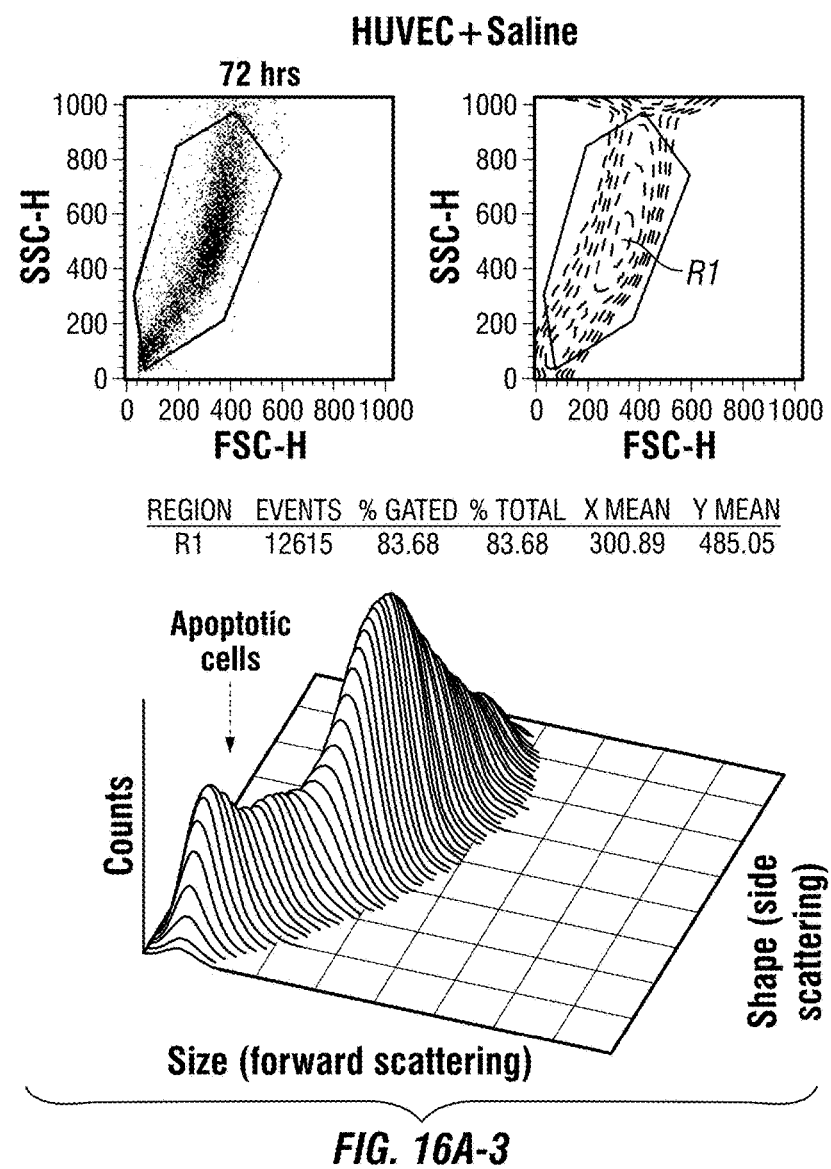
Figures 1, 16B:
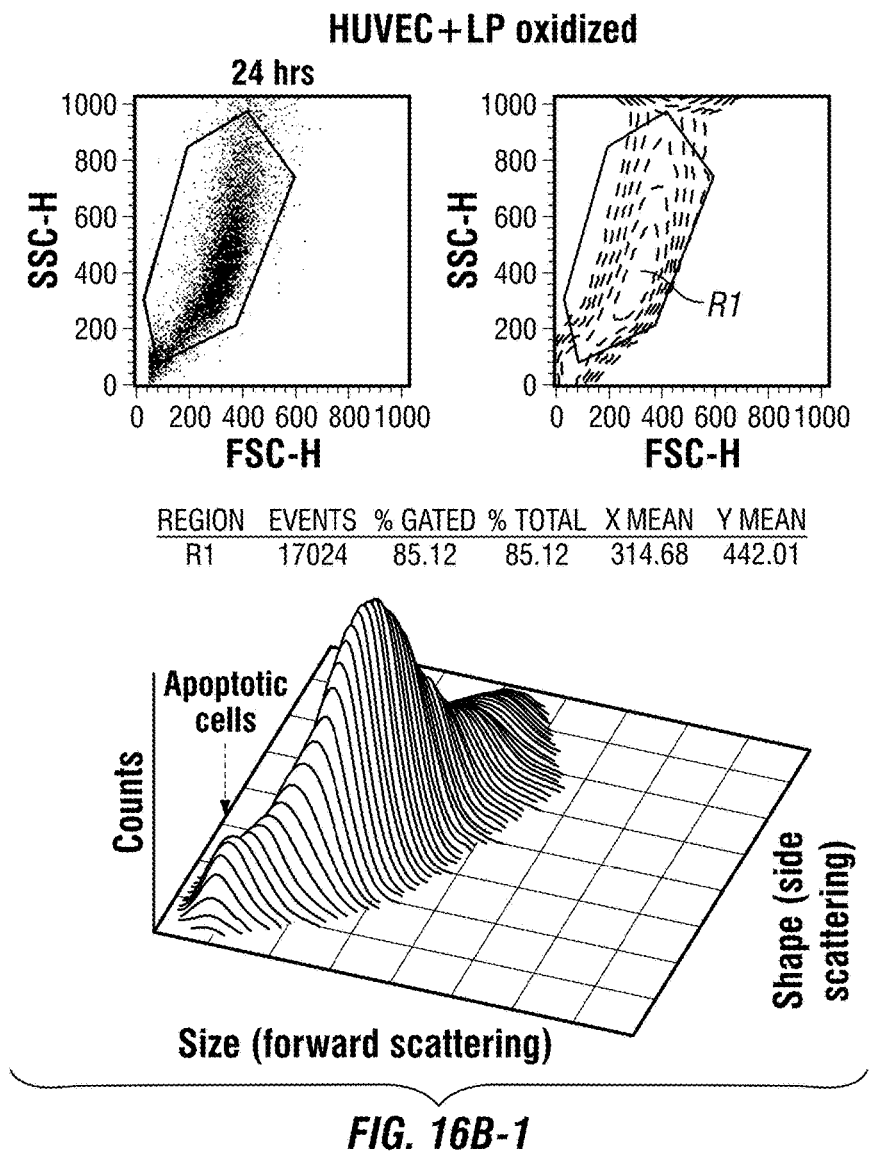
Figures 2, 16B:
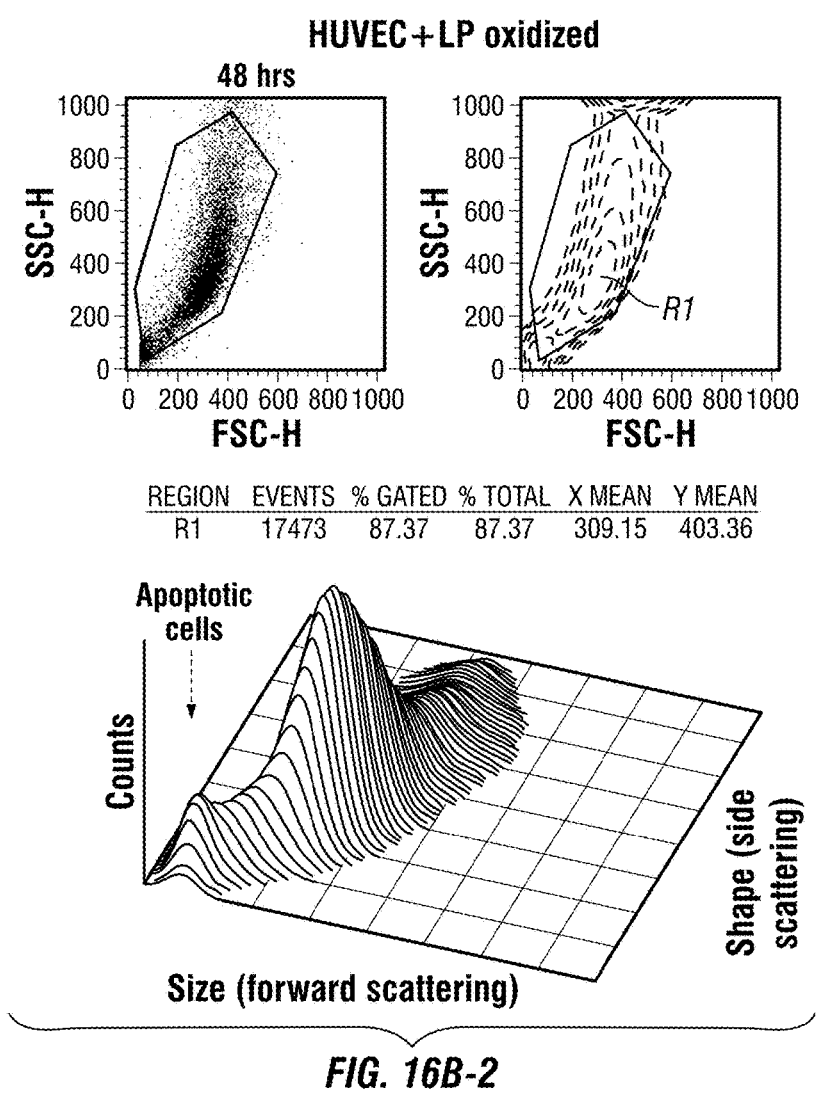
Figures 3, 16B:
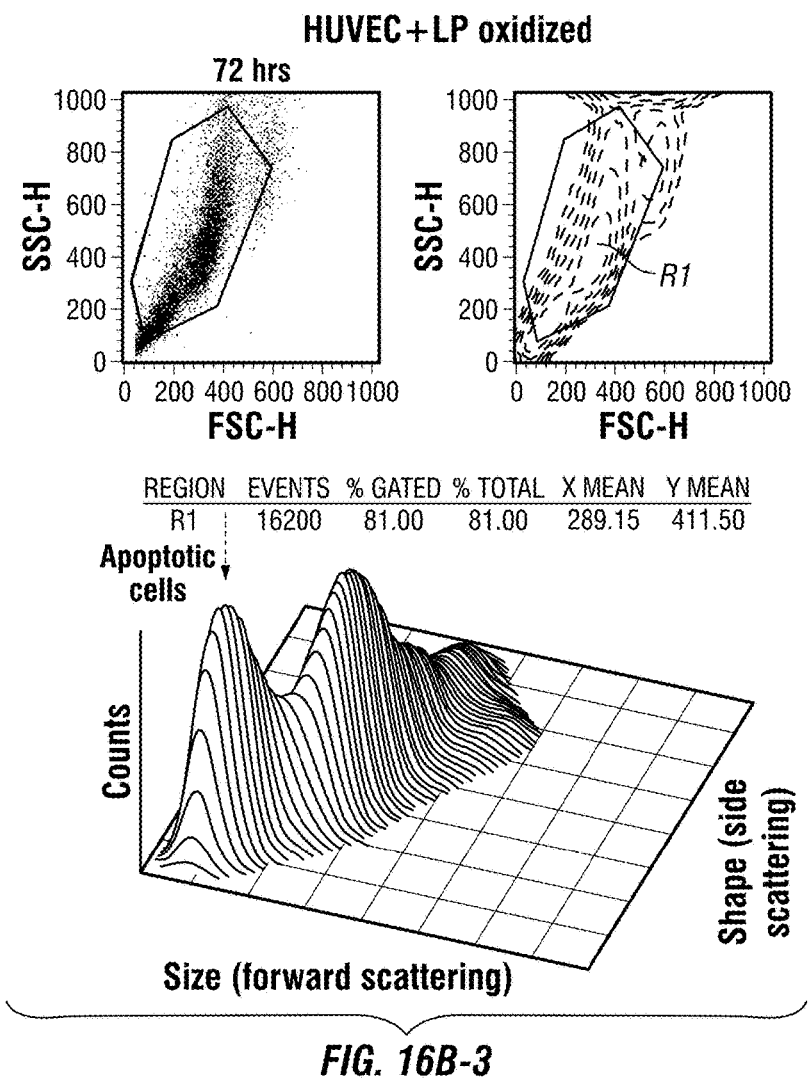
Figures 1, 16C:
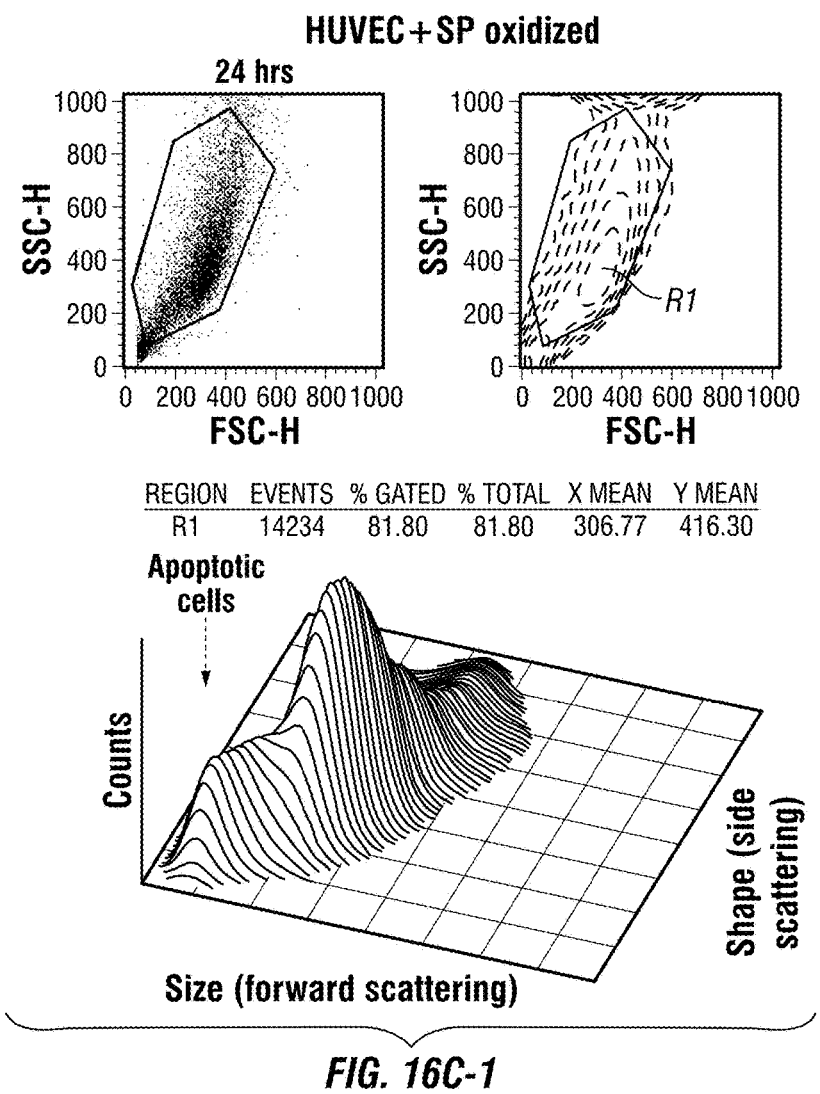
Figures 2, 16C:
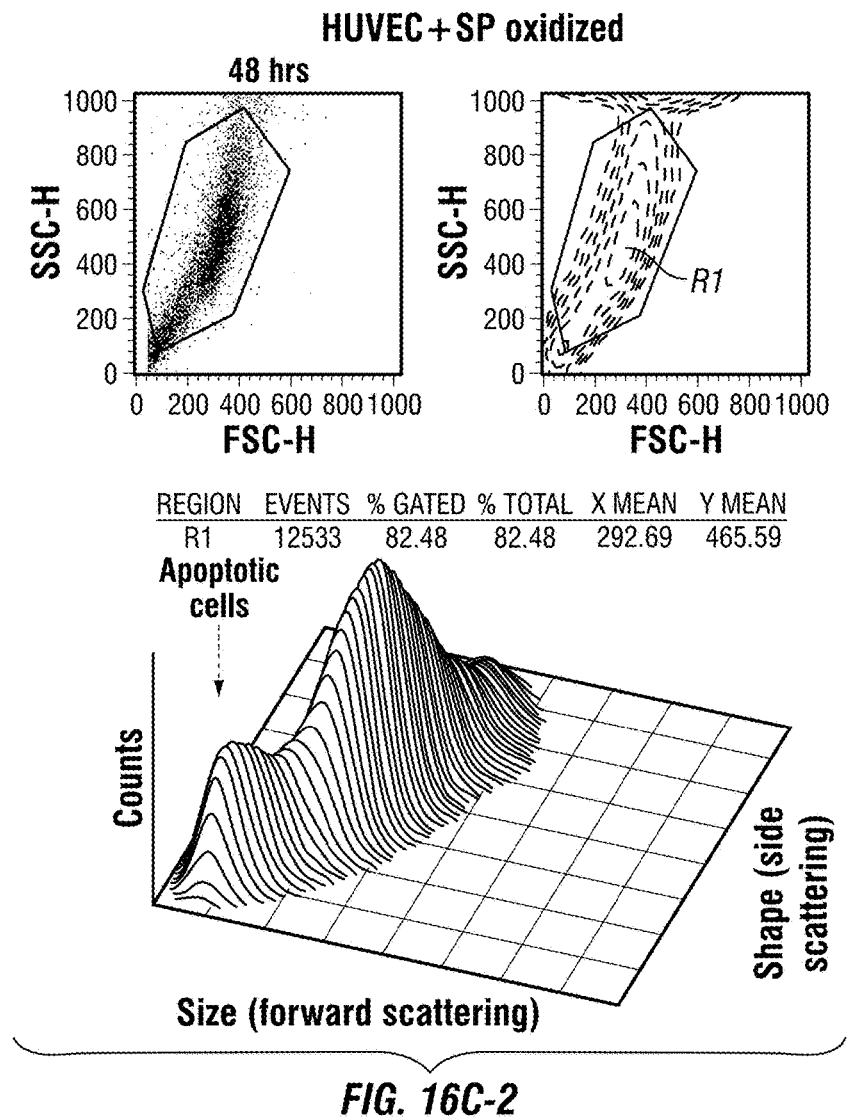
Figures 3, 16C:
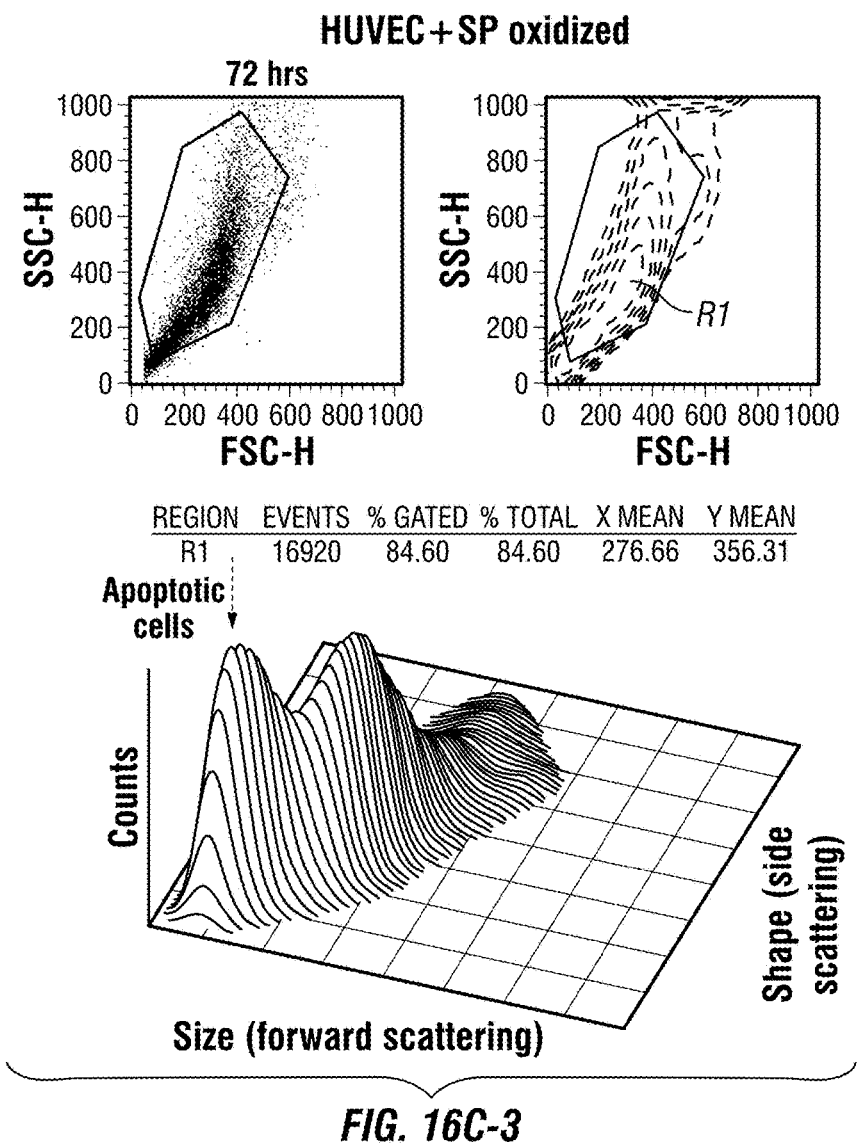

At 12, 24 and 48 hours, the proliferation of cells incubated with particles was exactly the same that in the control plate (FIG. 15, Panel B). At 72 hours the mean absorbance at 570 nm was 1.635 for HUVEC cells cultured without any particles (positive control) while it was 1.623 from cells incubated with a 1:1 ratio. At higher cells:particles ratios (1:5 and 1:10) HUVEC gave an absorbance value equal to 1.46 and 1.41 respectively (FIG. 15, Panels B-F). These lower values correlated with a slight decreased in cell proliferation when the cells were cultured in presence of a high number of particles. This was in accordance with the little increase in toxicity measured with the LDH assay at 72 hours (FIG. 14A, Panel B and FIG. 14B, Panels C-F).

The same proliferation pattern was observed in all the experimental conditions thus showing that porosity and surface chemistry did not either increased or decreased cell growth. All together these results did not suggest any significant change in cell viability due to exposition of cells to particles.

Cell Cycle and Apoptosis

HUVEC cells exposed for 12, 24, 48 and 72 hours to a 1:5 ratio of particles (LP and SP either oxidized or APTES modified) were analyzed after fixation and propidium iodide staining at FACS. The forward scattering (FSC) and side scattering (SSC) in a dot plot and in a contour plot were first analyzed (FIGS. 16A-1-FIGS. 16C-3, Panels A-C). FSC parameter provided an information of the size of the cells while SSC provided an information of the shape of the cells. The 3D plot on the bottom of each panel indicated on the z-axis the counts or events and provided an information on the overall distribution of the cells analyzed at FACS.

The peaks of necrotic/apoptotic cells that were characterized by a smaller and less homogeneous shape are indicated with the red arrows. The data reported in FIGS. 16A-1-FIGS. 16C-3, Panels A-C, are relative to HUVEC cells incubated with Saline (control) and with LP and SP oxidized Silicon particles. Cells distribution along time changed significantly, with a major accumulation in the low SSC, low FSC region at 48 and 72 hours. No significant difference in the distribution of cells among the 3 groups was noticed and the same results were obtained from the cells treated with LP and SP APTES modified particles. Although the present inventions are not bound by their theory of operation, the induction of cell death at later time points could be attributed to overconfluency. This could be expected since the seeded cells were at 60% confluency at day 0 in order to keep the experiment as close as possible to a physiologic solution, in which the particles would contact the endothelial walls of capillaries.

The distribution of the treated HUVEC cells in the different phases of the cell cycle was also measured quantitatively (FIG. 17A-17D). By comparing the data coming from control cells (FIGS. 16A-1-FIGS. 16C-3, Panel A, HUVEC+Saline) with the ones coming from LP and SP treated cells it was confirmed that exposure to Nanoporous Silicon Particles was not toxic and did not induce any significant increase in the amount of cell death. It was also demonstrated that there were no alterations in the cell cycle phases between treated and untreated cells.

Figure 17A:
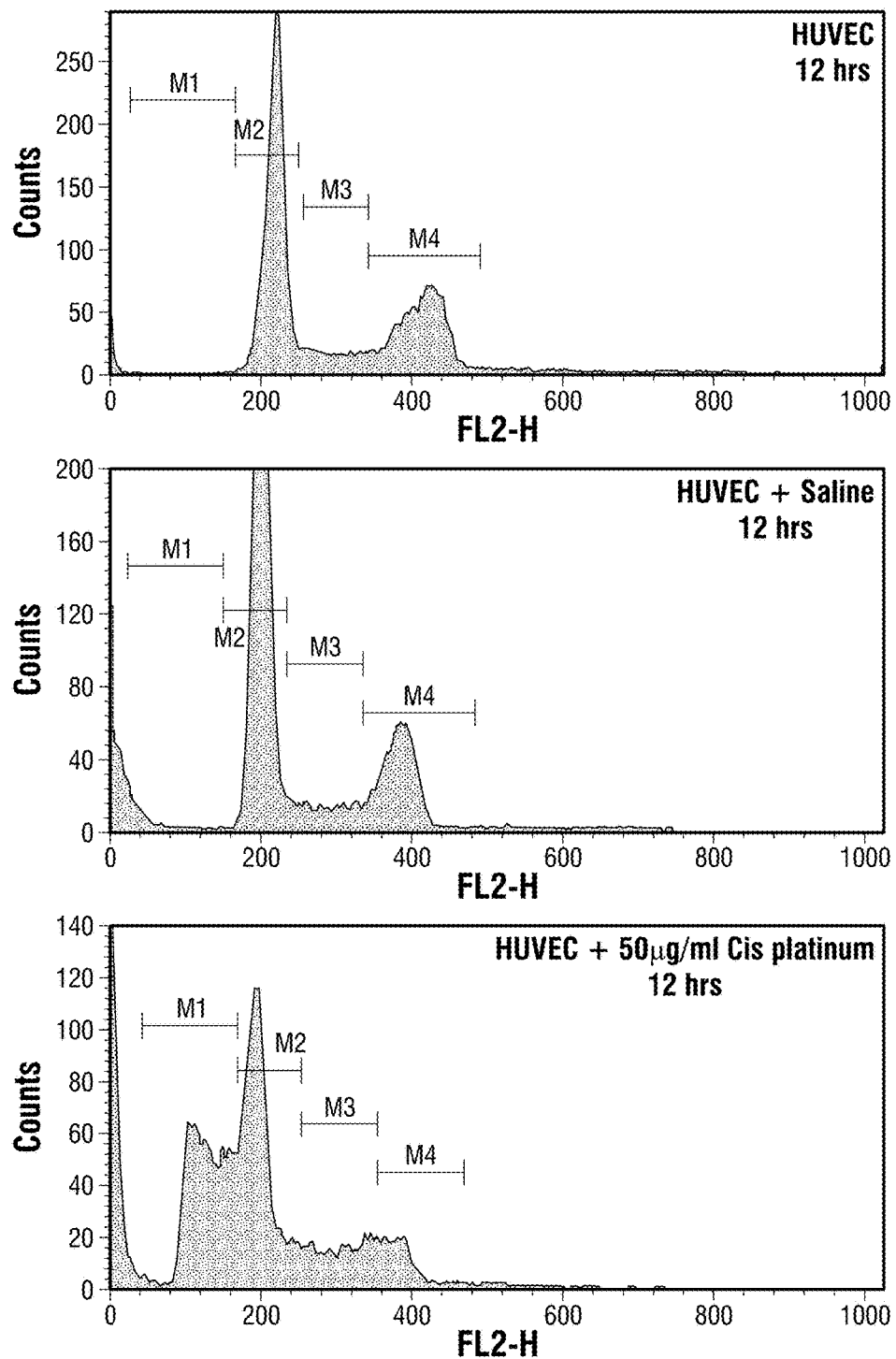
FIGS. 17A-17I present FACS 3D Profiles of HUVEC cells incubated with Nanoporous Silicon First Stage Particles and stained with propidium iodide to study cell cycle.
Figure 17B:
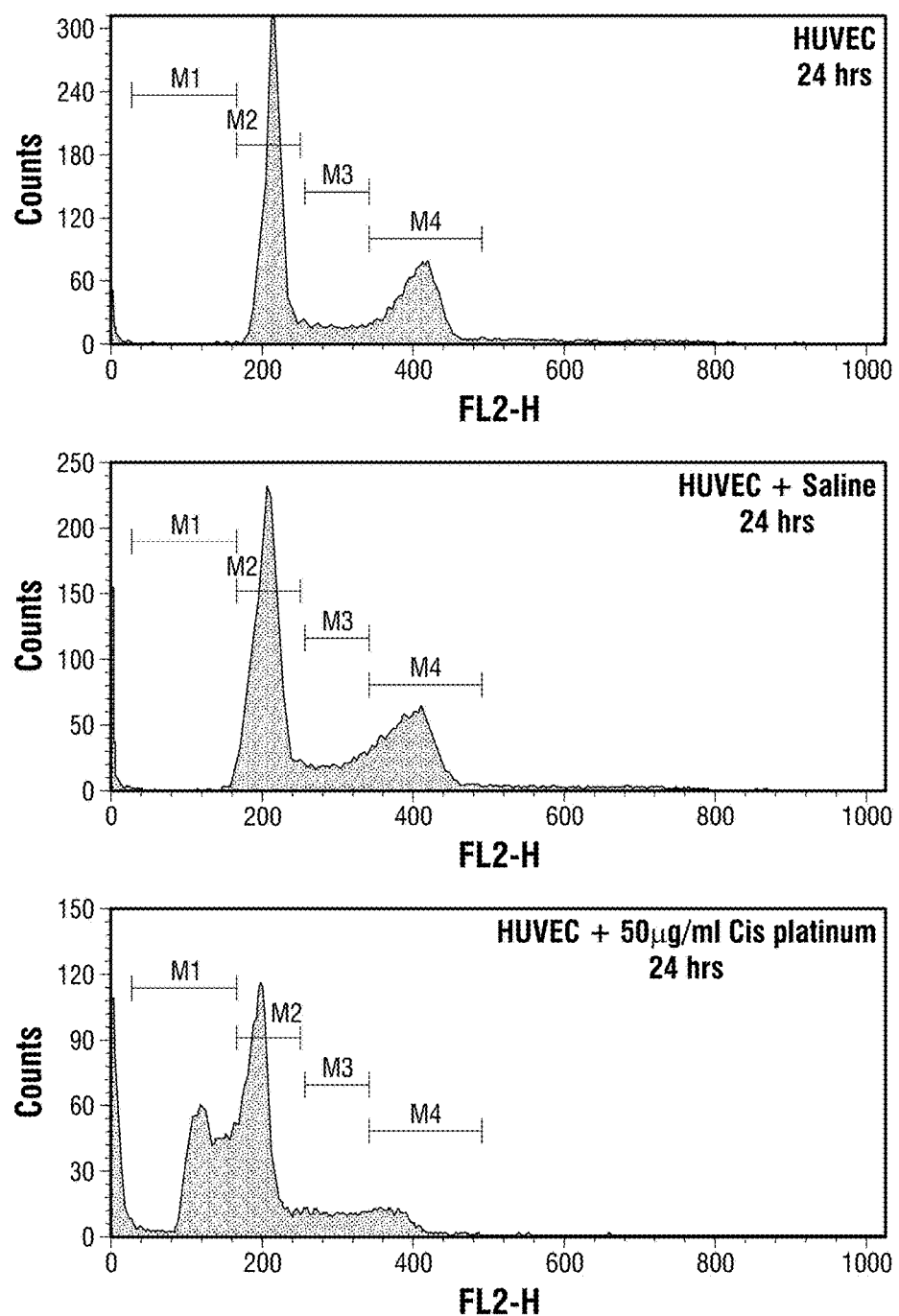
Figure 17C:
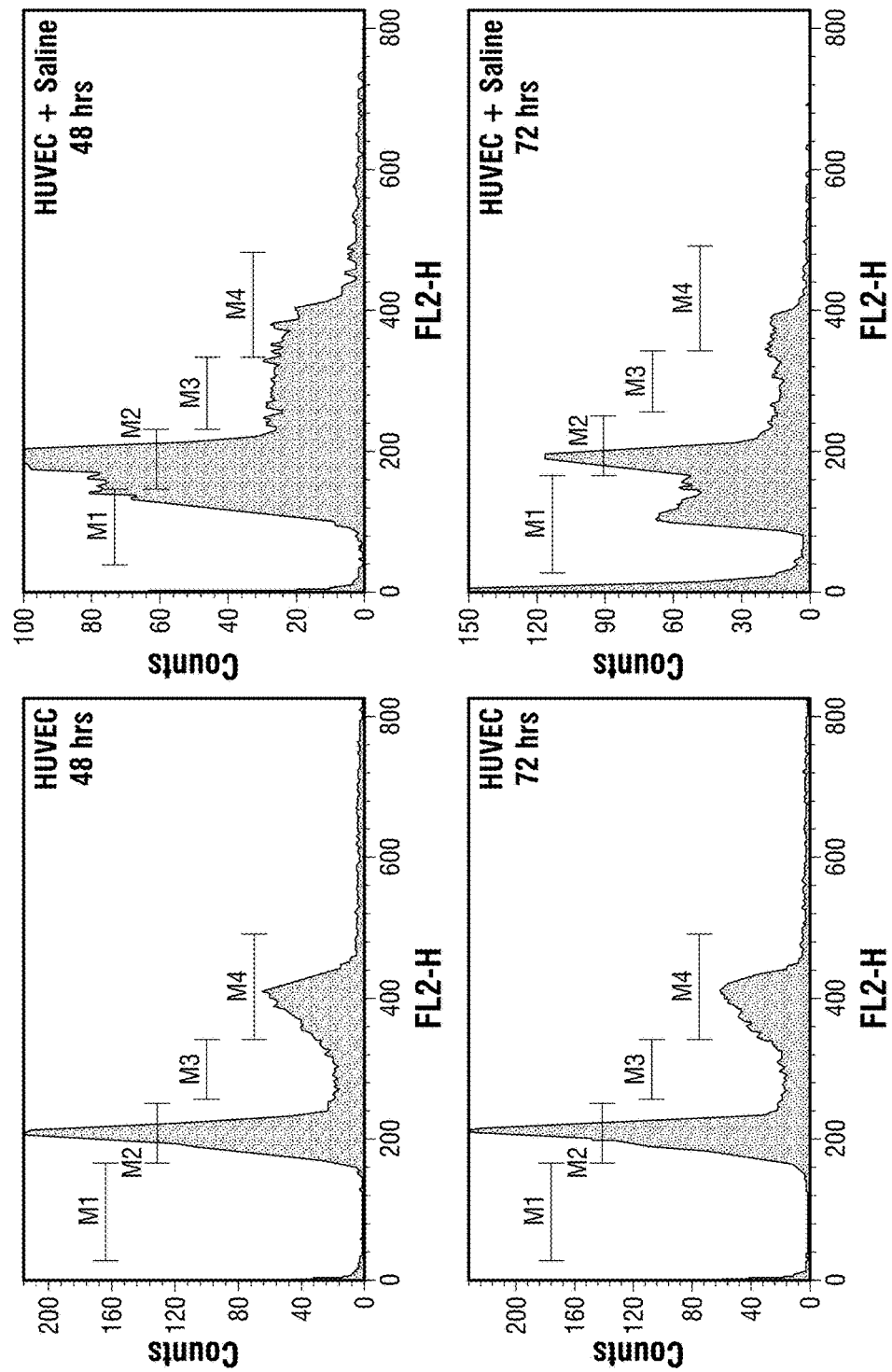
Figure 17D:
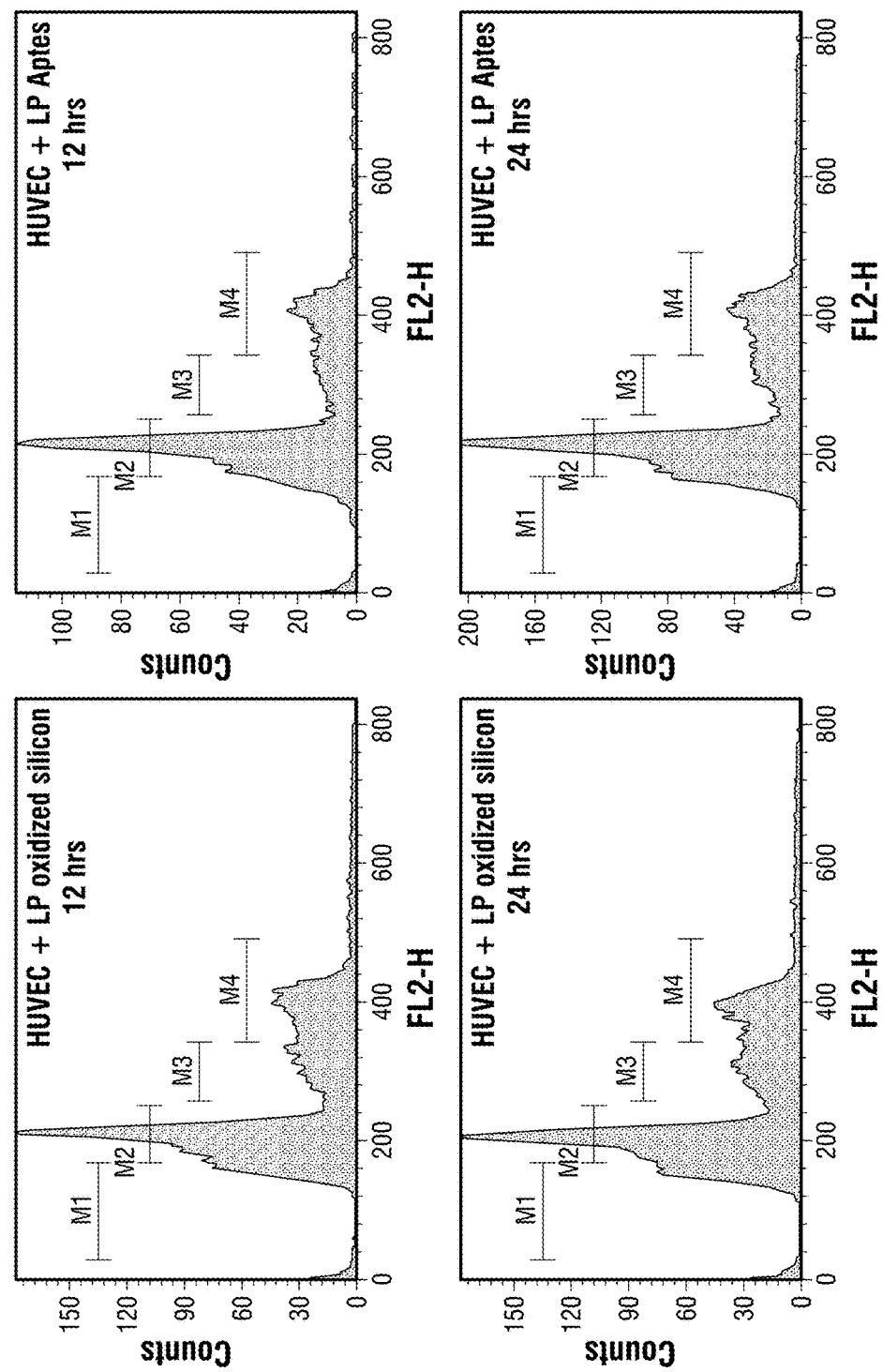
Figure 17E:
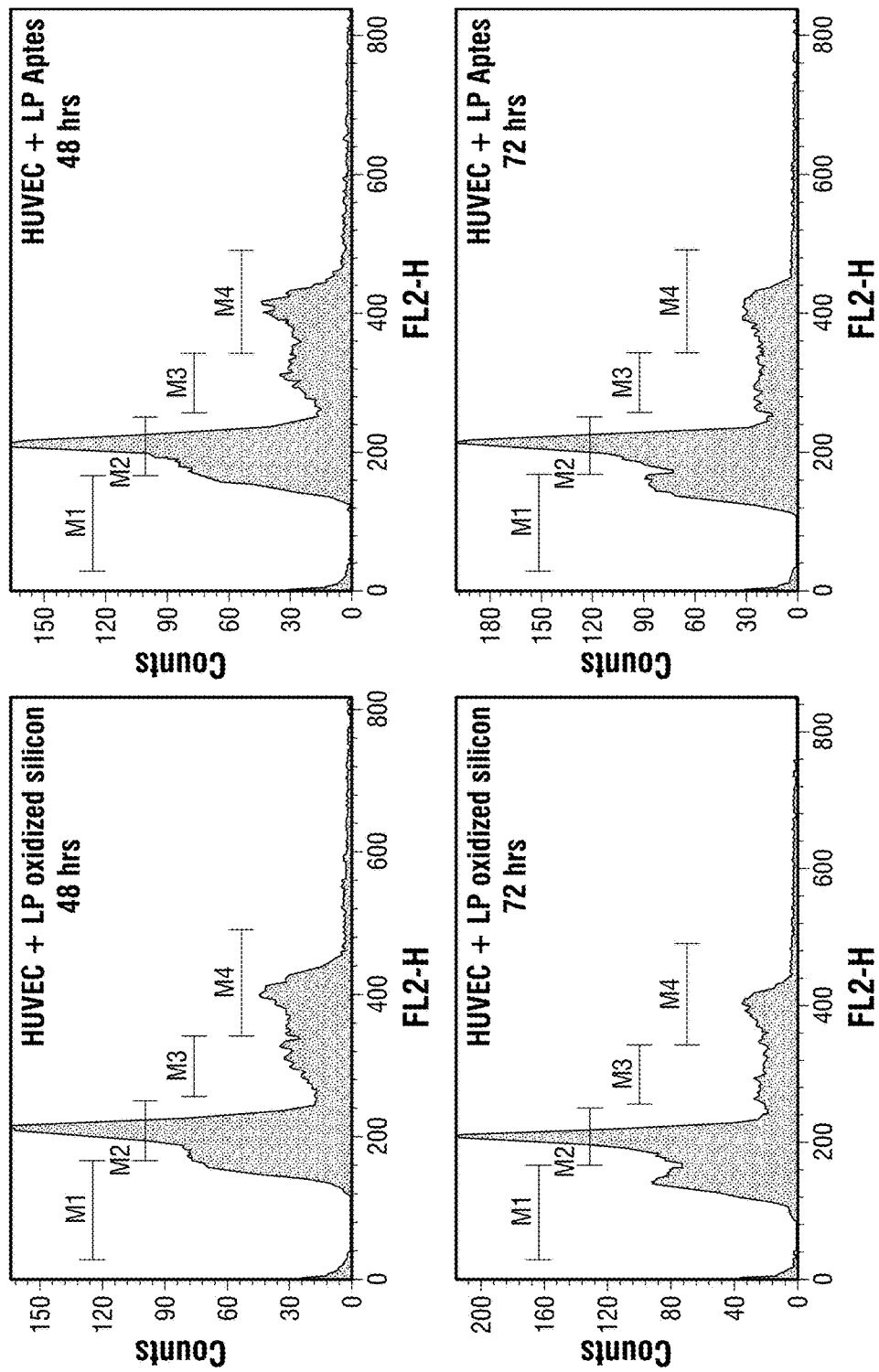
Figure 17F:
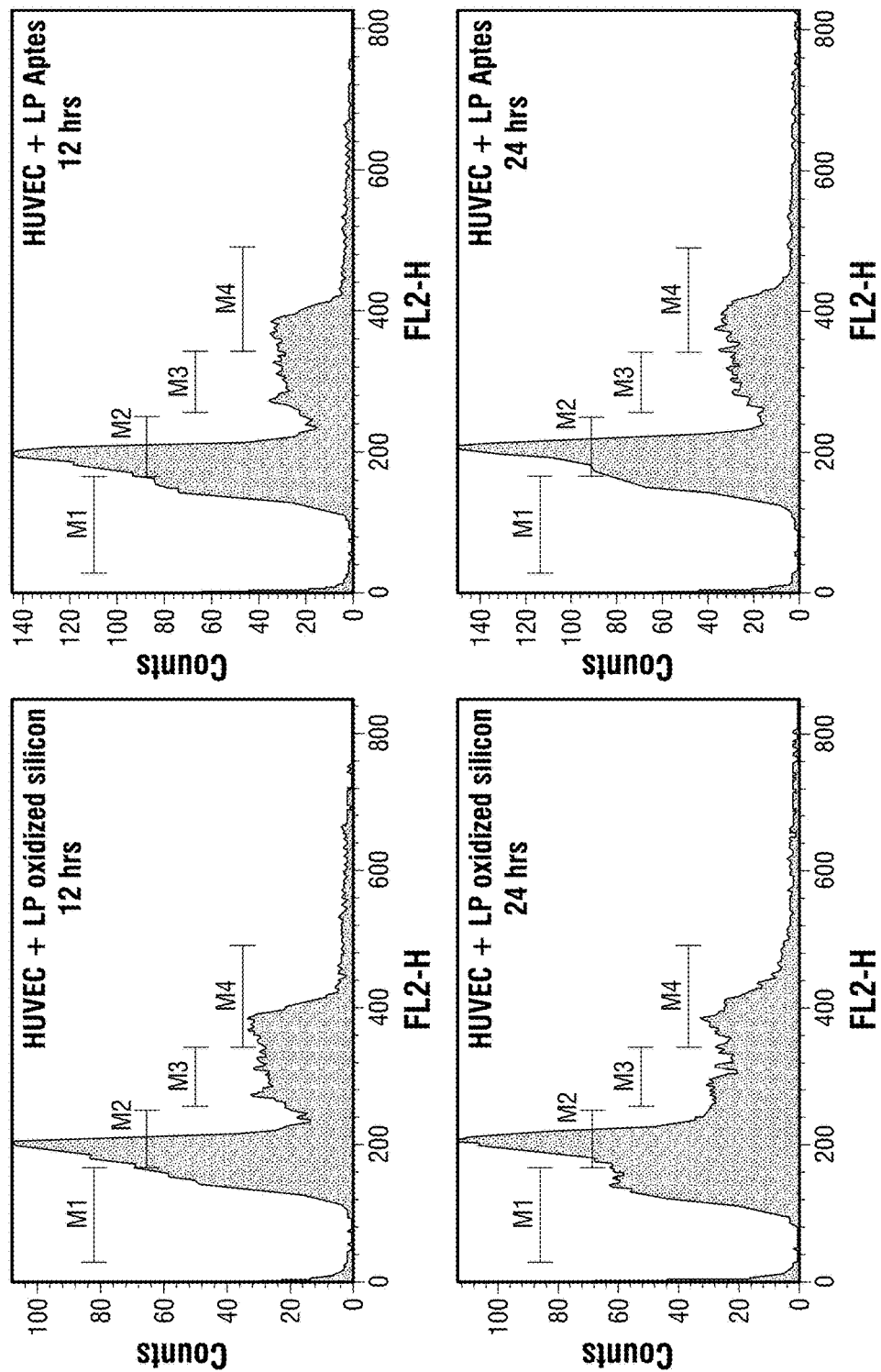
Figure 17G:
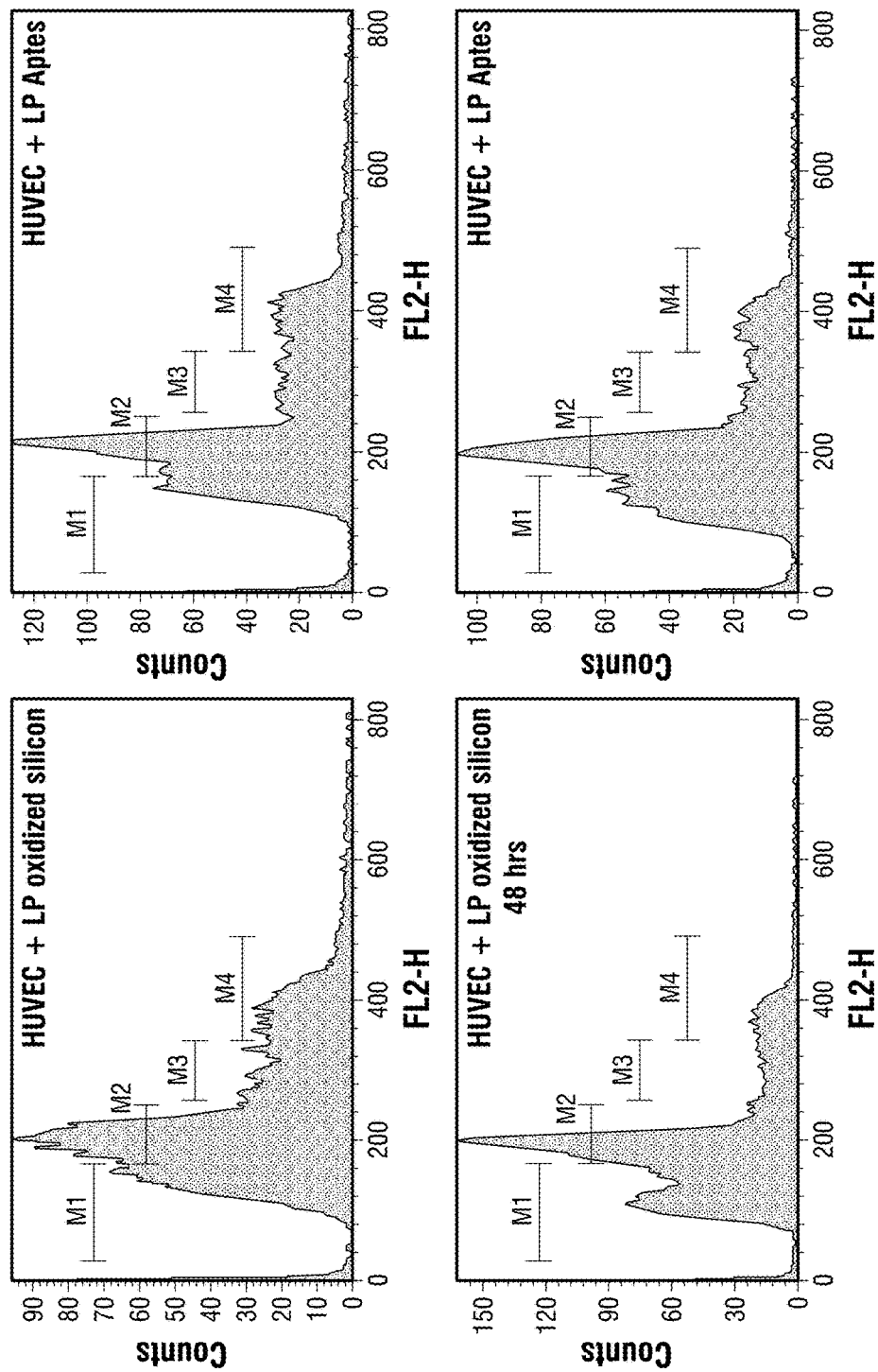
Figure 17H:
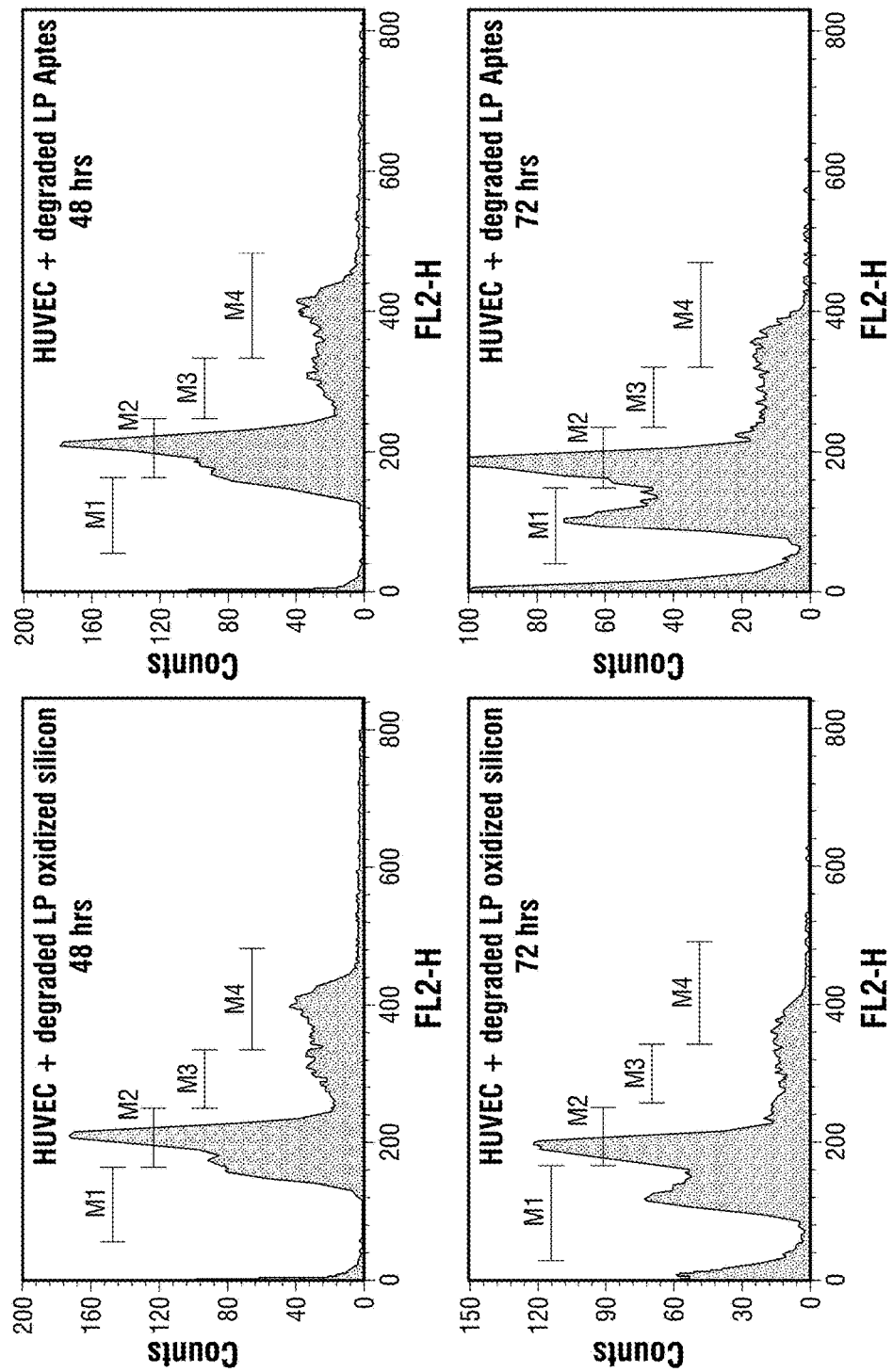
Figure 17I:
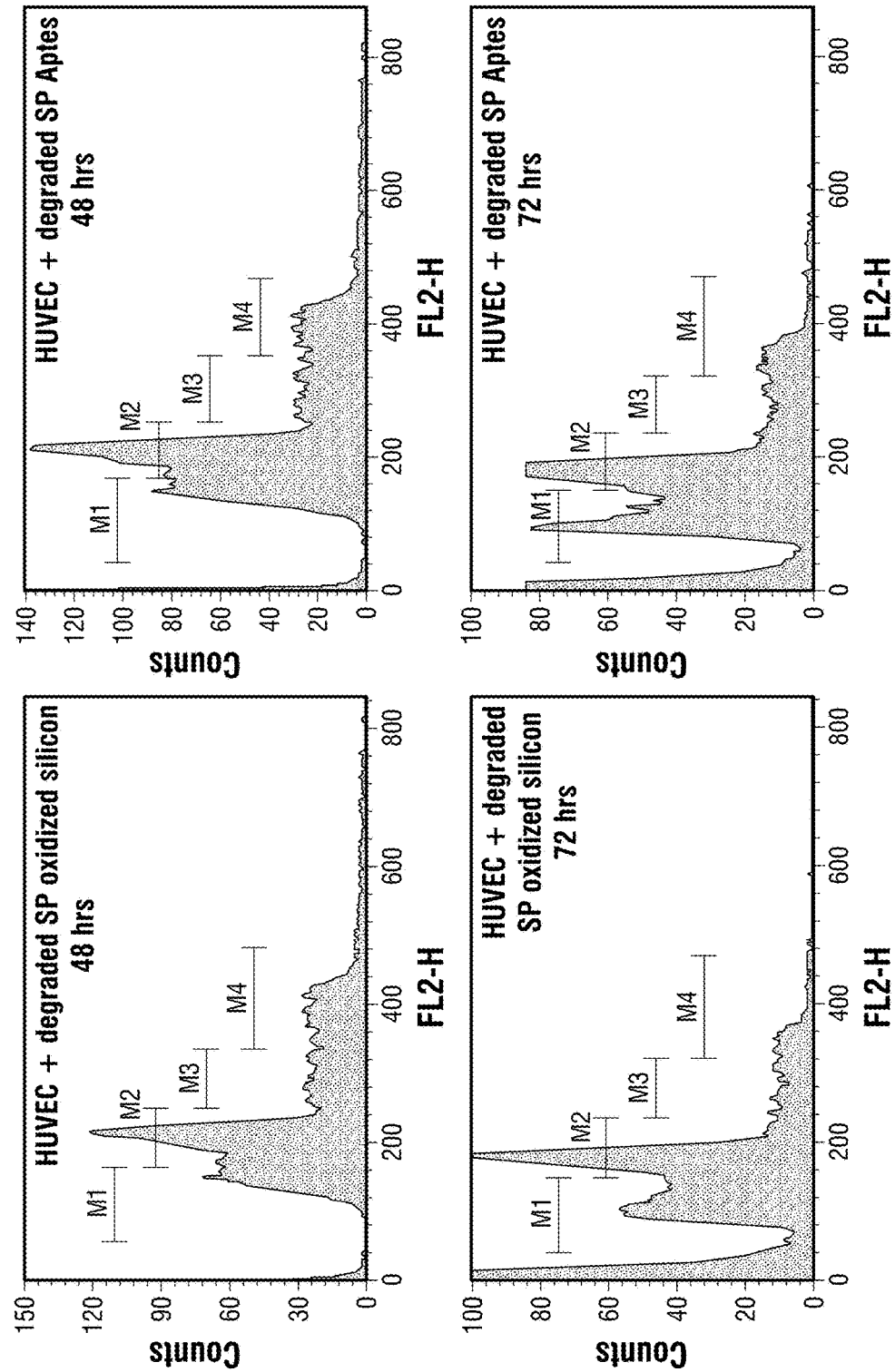
Figure 18A:
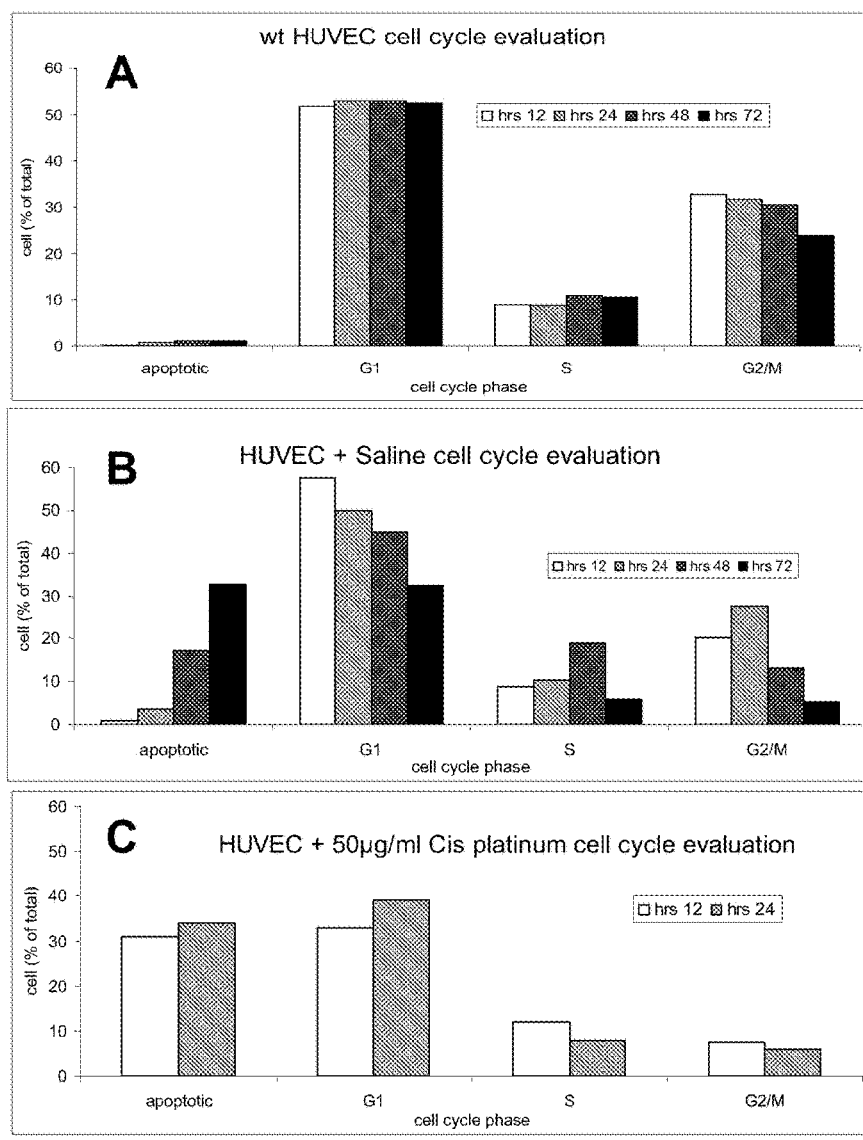
FIGS. 18A-C present statistical analysis of different phases of the cell cycle of cells exposed to nanoporous silicon first stage particles. Y axis in FIG. 18A, Panels A-C, FIG. 18B, Panels D-G, and FIG. 18C, Panels H-K reads % of total cell population.
Figure 18B:
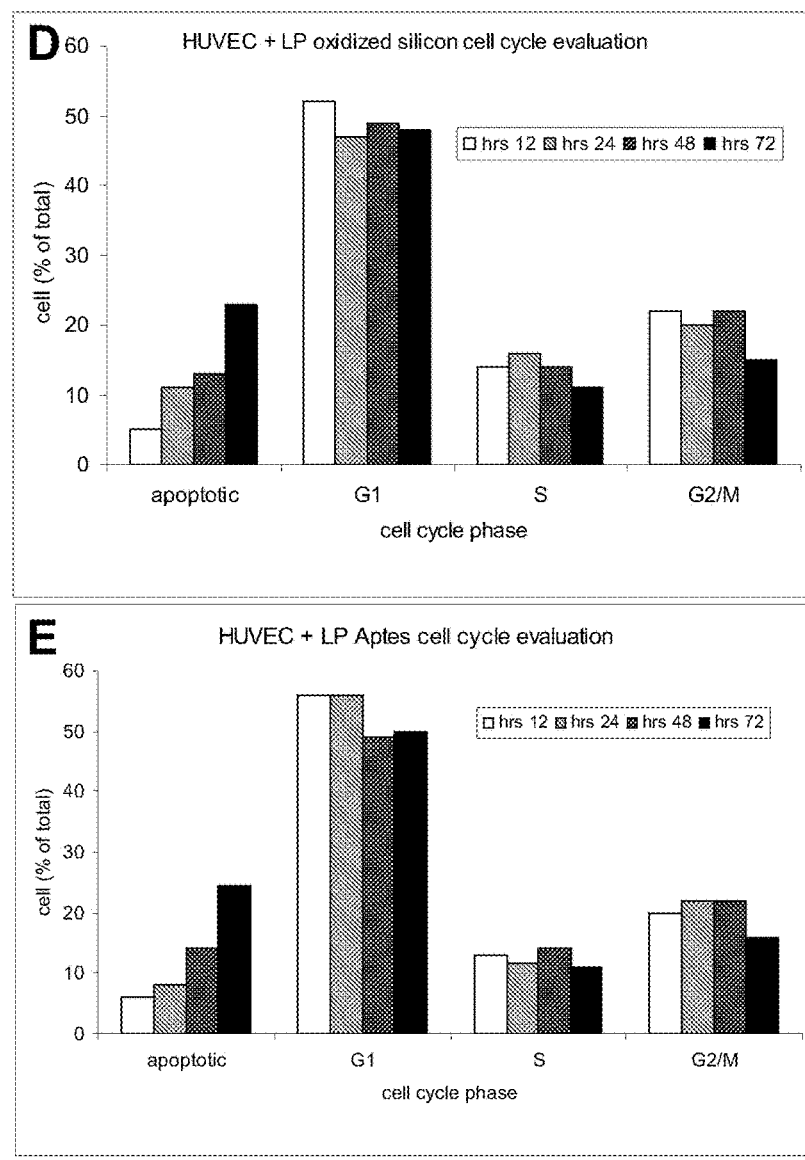
Figure 18C:
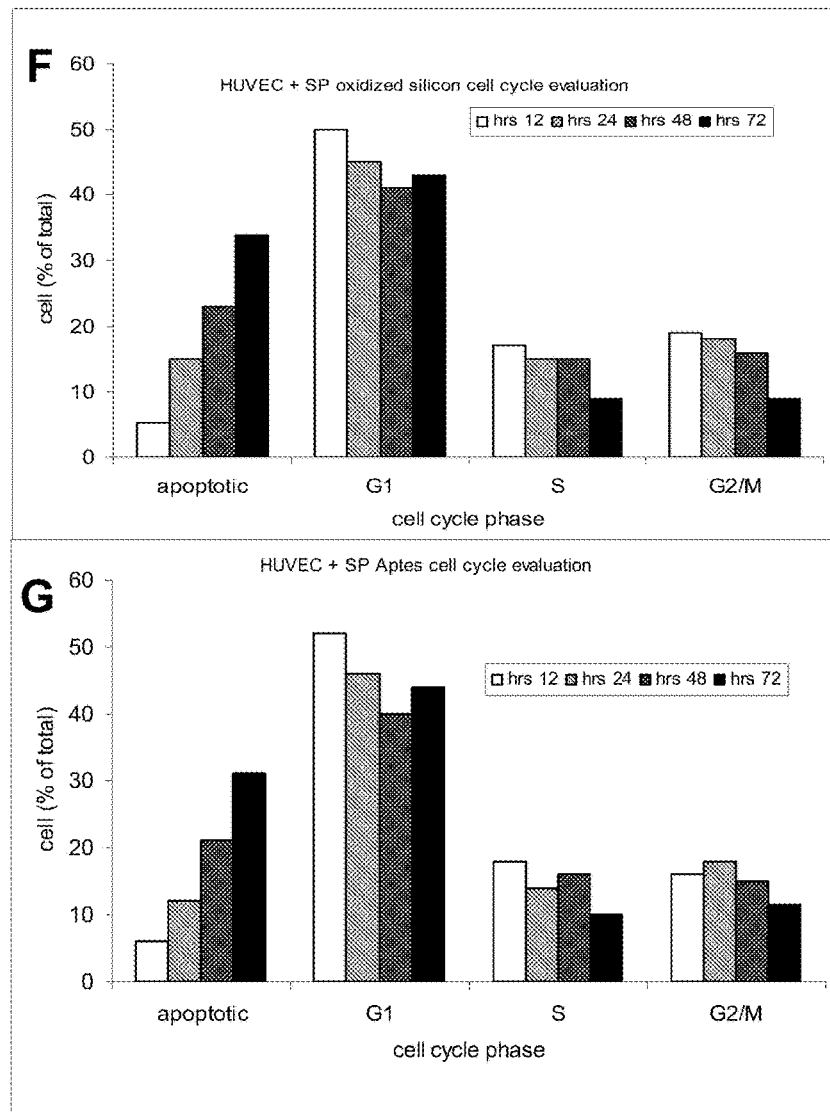

In order to demonstrate that not only the intact particles, but also their degradation products did not induce any toxicity, HUVEC cells were incubated with CCM containing the degradation product of all the particles type and confirmed the results described so far (FIG. 17D). A slight increase was measured in the amount of cells in the apoptotic region when the cells were incubated for 72 hours with the degradation product of SP oxidized and SP and LP APTES modified particles. It may be possible that smaller Silicon fragments produced during the degradation process induced some kind of toxicity[45-48].

WORKING EXAMPLE 2

A multi-stage delivery system based on biodegradable silicon particles containing nanopores of specific size as first stage carriers that may load, carry, release and deliver into cells multiple types of nanoparticles with a precise control was developed. The first stage silicon nanoporous particles may be simultaneously loaded with different types of second stage nanoparticles, which are released in a sustained fashion over time. The major physical, chemical, and electrostatic mechanisms that control the loading and release of second stage nanoparticles were defined. Finally, it was shown that the porous silicon carriers are able to locally delivery the second stage nanoparticles into the cytoplasm. Taken together, these studies provide evidence that silicon nanoporous particles may be used as cargoes for the simultaneous deliver of different types of nanovectors into cells. This system may offer unprecedented methods to achieve intracellular delivery of multiple therapeutics and/or imaging agents.

Introduction

Since its development in the last decade, nanotechnology has being used in a wide variety of applications in biomedical research for disease detection, diagnosis, and treatment[1-3]. The objectives of many studies involving the development and refinement of nanoparticles have focused on their use as agents for delivery of therapeutic or imaging molecules to organs, tissues, and cells[4,5]. A number of different nanovectors have been evaluated for therapeutic uses, including liposomes of various sizes and composition[6,7], quantum dots (Q-dots)[8,9], iron oxide[10], single wall carbon nanotubes (SWNTs)[11], gold nanoshells[12,13] and several other types of nanoparticles[14]. The progress thus far has given rise to the field defined as "molecularly targeted therapeutics"[15-18], however the accomplishment of the original objective, which is to selectively deliver a therapeutic agent using a nanovector-based delivery system, has not been fully realized[19,20].

The integration of nanovectors into nanoporous silicon particles may allow the nanovectors to evade the natural biological barriers that may normally retard their therapeutic effects. Such approach may provide protection of therapeutic agents from surrounding fluids and molecules that may normally degrade them prematurely and from uptake by the Reticulo Endothelial System (RES). This may lead to a greater stability of the active agents, while providing increased delivery and concentrated dosage of therapeutic agents to a targeted tissue.

The multiple and simultaneous loading of second stage nanoparticles into first stage silicon nanoporous particles was achieved. The second stage particles (Q-dots and SWNTs) were slowly released over time periods sufficient for the first stage particle to reach a specific biological target site. The main physical, chemical and electrostatic mechanisms that govern the loading and release processes were. The nanodelivery system was able to locally release its payload into cells.

Results

First and Second Stage Particles

Figure 19:
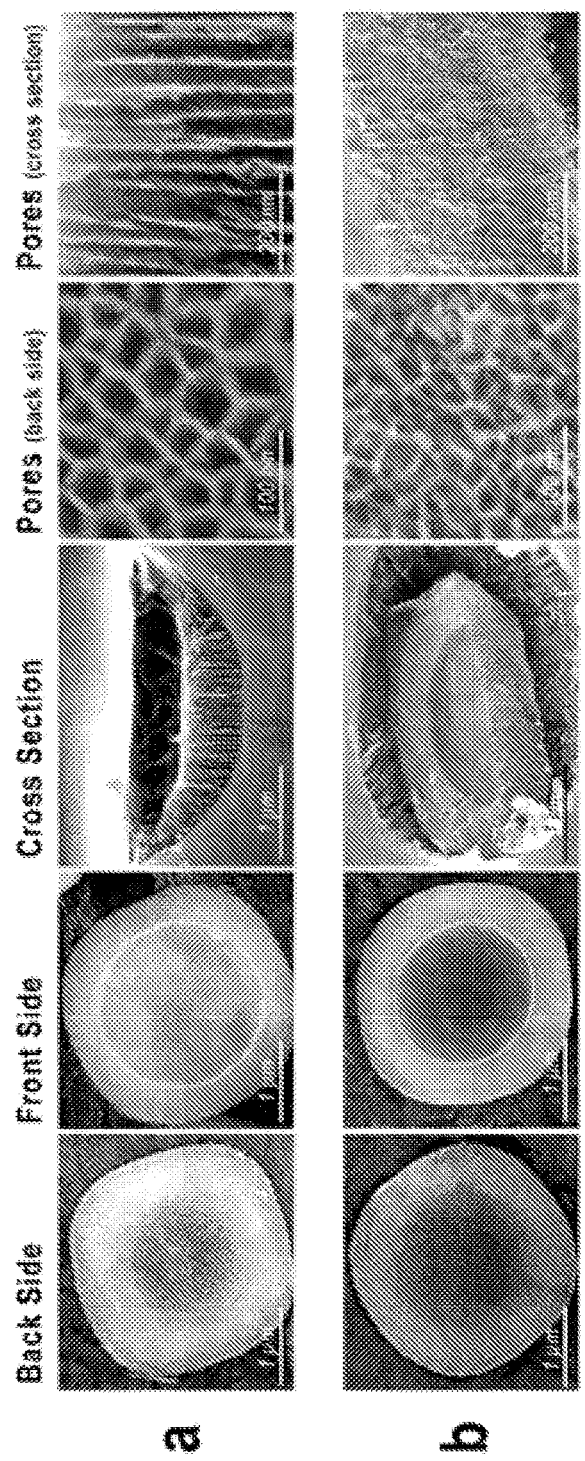
FIG. 19, Panels a and b, demonstrate SEM images of a porous silicon particle. "Large pore" (LP, FIG. 19a) and "small pore" (SP, Panel b) particle images showing (from left to right) the back side, front side, a cross-section, a closer view of the pores on the back side and of the pores in the cross-section. The size and shape of the LP and SP particles are the same, the size and structure of the pores are significantly different.

Silicon microparticles were characterized by Z2 Coulter® Particle Counter and Size Analyzer to measure their volume, size and concentration and by Scanning Electron Microscopy (SEM) to evaluate their morphology in detail. FIG. 19, Panels a and b, show representative SEM images of the back and front sides and of the cross sections of "large pore" (LP) and "small pore" (SP) silicon particles respectively. These particles are highly porous and hemispherical in shape. The diameter of LP particles is approximately 3.5 µm, with pores of straight profile, which cross the particles perpendicularly to their external surface and have pore size ranging from 20 to 30 nm (FIG. 19, Panel a). SP silicon particles have a mean diameter of 3.2 µm, and have a flatter shape than LP silicon particles as a consequence of anodization and electropolishing processes used to produce them, with pore sizes less than 10 nm (FIG. 19, Panel b). Both LP and SP silicon particles have a thickness of 0.5-0.6 µm. According to BET analysis, the surface area is 156 m2 g-1 for LP particles and 294 $m^2$ $g^{-1}$ for SP particles. Pore volume is 0.542 $cm^3$ $g^{-1}$ for LP particles and 0.383 cm3 g-1 for SP particles. The pore density, size, shape and profile may be finely tuned by changing electrical current, etching time, and doping, which is reproducible from batch to batch. Non-oxidized silicon is a hydrophobic material but a variety of surface treatment protocols are available for silicon-based materials to be stabilized and further functionalized with oligonucleotides[27], biomolecules[28], antibodies[29,30], and polyethylene glycol (PEG) chains[31]. Oxidized silicon particles have a negative zeta potential value (−10.1 for LP; −11-25 for SP) due to the presence of the hydroxyl groups on the surface of the particles[32]. The particles that were modified with APTES have a positive zeta potential value (6.52 for LP; 6.45 for SP) as a consequence of the introduction of amino groups on their surface. The hydrodynamic size of Q-dots was measured by the diffusion coefficient of colloidal in solution using dynamic light scattering technique. Diameter was 13 nm for Amino-PEG Q-dots, and 16 nm for Carboxyl Q-dots. Size of PEG-FITC-SWNTs was evaluated by AFM microscopy. The diameter of non PEGylated SWNTs is around 1 nm but due to the PEG surrounding the nanotubes, PEG-FITC-SWNTs used for this study had a mean diameter of 4 nm, and a mean length of 30 nm. The SWNTs were functionalized using PEG-amine through carboxylic acids obtained via the SWNT cutting process and were conjugated to FITC to allow for their fluorescent imaging. Second stage nanoparticles with fluorescent properties were selected to quantify loading into and release from silicon nanoporous particles using established techniques, such as flow cytometry, fluorimetry, as well as both fluorescence and confocal microscopy. Physical and chemical of first and second stage particles are summarized in Table 6.

TABLE 6

| 1st Stage Particle | Chemical Modification | Pore size, nm | Zeta potential, mV |
|---|---|---|---|
| "Large pore" (LP) | oxidized | 20-40 | −10.1 |
| LP | APTES | 20-40 | 6.52 |
| "Small pore" (SP) | oxidized | 5-7 | −11.15 |
| SP | APTES | 5-7 | 6.42 |

| 2nd Stage Particle | | Size, nm | |
|---|---|---|---|
| Q-dots | Amino PEG | 13 | −1.21 |
| Q-dots | Carboxyl PEG | 16 | −32.8 |
| SWNTs | PEG-FITC | Diameter 4 Length 30 | −9.21 |

Loading Second Stage Nanoparticles into First Stage Silicon Particles

Protocols to efficiently load nanoparticles inside the pores of first stage silicon particles were developed. One of the factors affecting the loading process was the amount of second stage particles in the media surrounding the particles. The analyzed fluorescent intensity of silicon particles loaded with increasing amounts of both Q-dots (FIG. 20, Panel A) and PEG-FITC-SWNTs (FIG. 20, Panel B) and demonstrated that particles loading was directly correlated with the second stage particles concentration. By raising the concentration of the second stage particles, progressively higher levels of loading were achieved as assessed by flow cytometry (FIG. 20, Panels A and B) and by direct visualization with fluorescent microscopy (FIG. 20, Panels C and D).

These studies also demonstrated that surface chemical properties of both the first stage silicon particles and second stage particles affected loading efficiency and stability of the assembled multi-stage nanoparticulate carrier system. These observations were confirmed by the results shown in FIG. 21, Panel a and Panel c, in which Carboxyl Q-dots, which had a negative surface charge (zeta potential −32.8 mV), and PEG-FITC-SWNTs, with a negative surface charge (zeta potential −9.21 mV) could be more efficiently loaded into LP APTES modified silicon particles, than into the LP oxidized silicon particles, which had a negative surface charge. Given the wide range of protocols available to modify porous silicon[27,29-35], it is possible to efficiently load any kind of second stage particles by exploiting first and second stage surface chemistries.

Loading of second stage nanoparticles was a very rapid process. FIG. 21, Panels a and c illustrate the results obtained when LP oxidized silicon particles and LP APTES modified silicon particles were incubated with a fixed amount of both Amino and Carboxyl Q-dots and PEG-FITC-SWNTs. Complete loading of the first stage porous silicon particles occurred within 15 min if the combination of first stage porous silicon particles and second stage particles matched the electrostatic criteria described above. The loading of SP oxidized silicon particles and SP APTES modified silicon particles with second stage nanoparticles was also evaluated (FIG. 21, Panels c and d, respectively). Q-dots size was between 13 and 16 nm so they could not be loaded into the pores of SP silicon particles (5-7 nm). On the contrary, the pores of LP silicon particles (20-40 nm) were sufficiently large to allow Q-dots loading. As a consequence, SP particle mean fluorescence was only 6% of LP particles. Conversely, the smaller size of the PEG-FITC-SWNTs was compatible with SP particle pores, resulting in increased loading (25% of the PEG-FITC-SWNTs loaded into the LP silicon particles).

Releasing Second Stage Nanoparticles from First Stage Silicon Particles

To evaluate the multistage delivery system as a tool for drug delivery, the kinetics of release of the second stage particles from the nanoporous silicon first stage particles was investigated. In order to mimic physiologic conditions, all the experiments were performed at 37° C. in buffered saline and the release solution was replaced at each time point. FIG. 21, Panels e-h, demonstrate that both types of second stage particles were released over time from the first stage silicon particles. Surprisingly, the release process was sustained, with complete release reached after 20 hours. In addition, the release kinetics significantly differed between Q-dots and PEG-FITC-SWNTs, with Q-dots being released significantly faster than SWNTs.

Control experiments performed with SP oxidized silicon particles (FIG. 21, Panel f) and SP APTES modified silicon particles (FIG. 21, Panel h) confirmed that Q-dots were not loaded inside the pores. Detachment of Q-dots from the surfaces of SP silicon particles was massive and rapid (>80% in 15 min) suggesting that they were loosely interacting with the silicon particle surface. In contrast, the kinetics of release of the PEG-FITC-SWNTs second stage nanovectors from LP and SP silicon particles were comparable, confirming that PEG-FITC-SWNTs were loaded into the pores of first stage SP particles.

Figure 22:
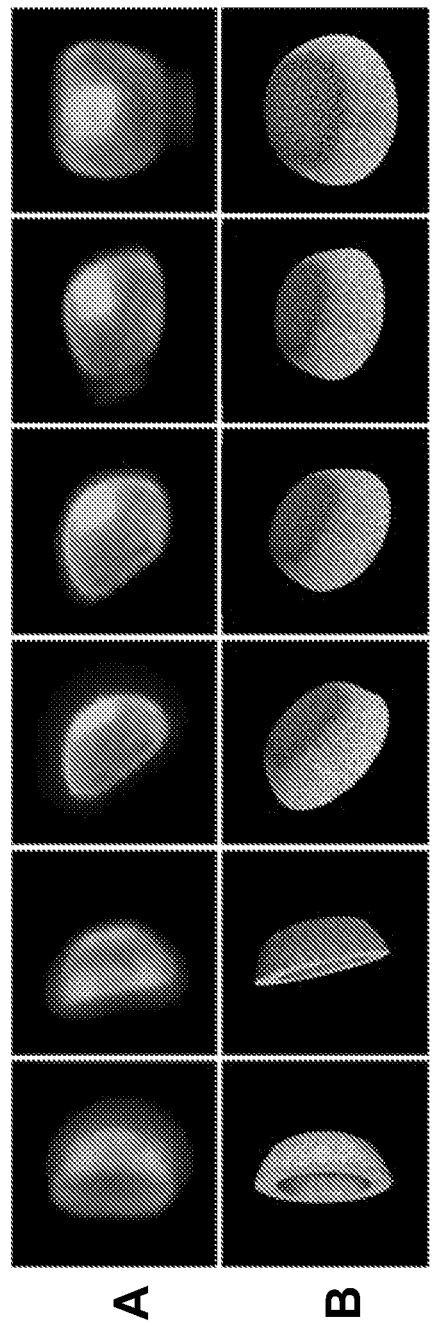

Confocal microscopy was used to further characterize loading of the second stage nanoparticles into the pores of the silicon carriers. FIG. 22, Panels a-b, show a series of 3 dimensional projections and rotations of LP APTES silicon particles loaded with Carboxyl Q-dots. A more intense fluorescence signal was detected in the central region of the back face of the silicon particles, where larger pores are, see FIG. 19, Panel a. The less intense signal coming from the surrounding areas was due either to partial loading into smaller pores or by the interaction of Q-dots with the surface of the silicon particle.

Multiple Loading

Figure 23A:
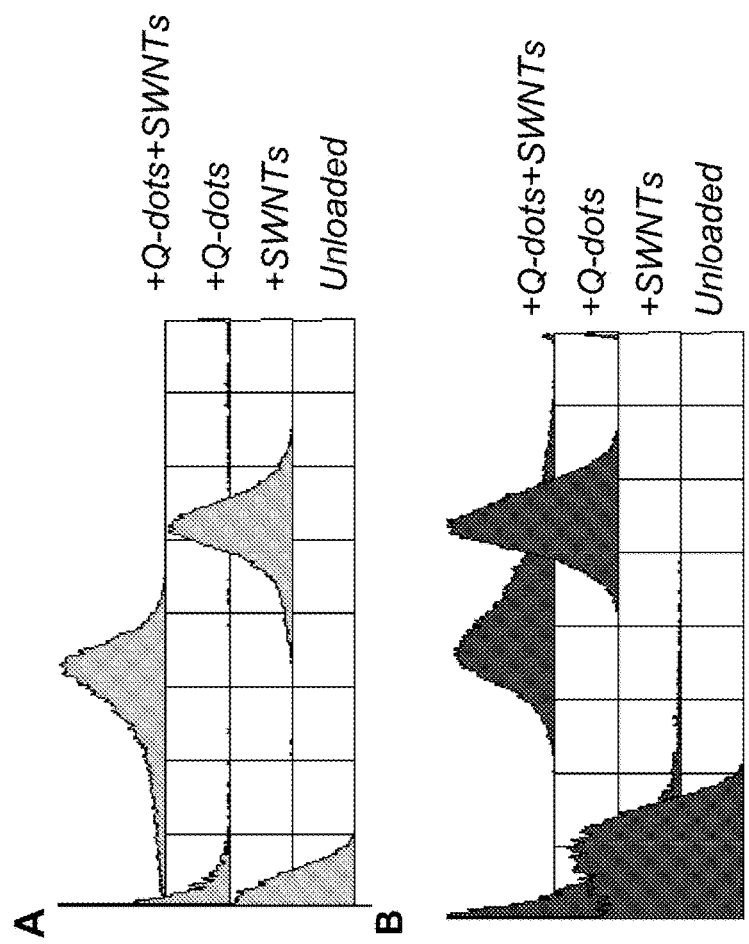
FIGS. 23A-23C illustrate simultaneous loading and releasing of Q-dots and PEG-FITC-SWNTs second stage particles in nanoporous silicon first stage particles. Flow cytometry analysis showing background green and red fluorescence of LP APTES particles (Unloaded.
Figure 23B:
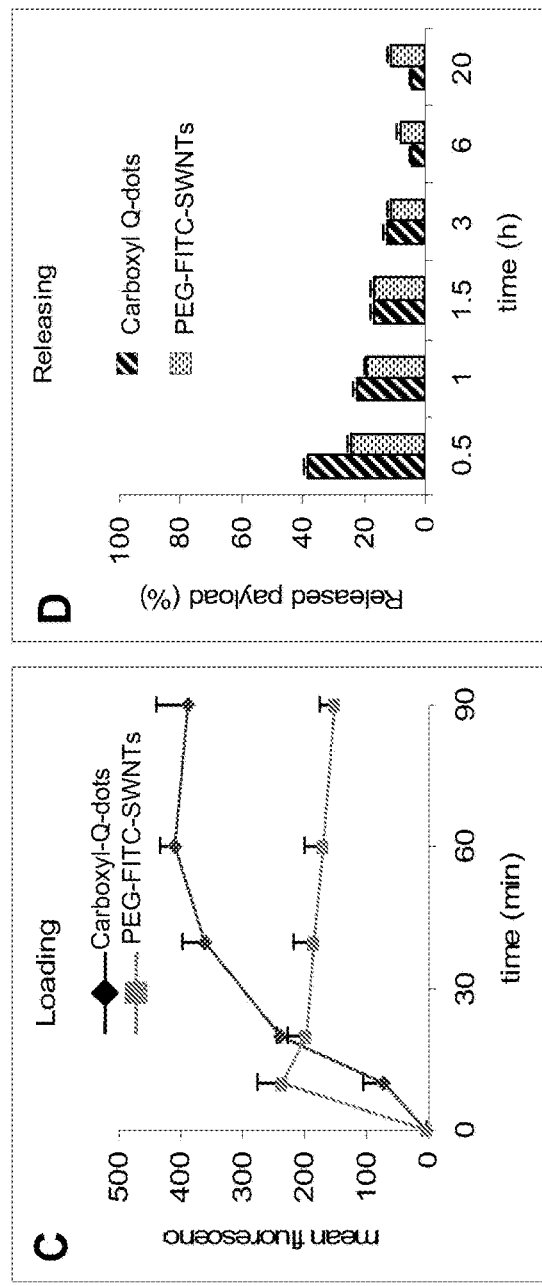
Figure 23C:
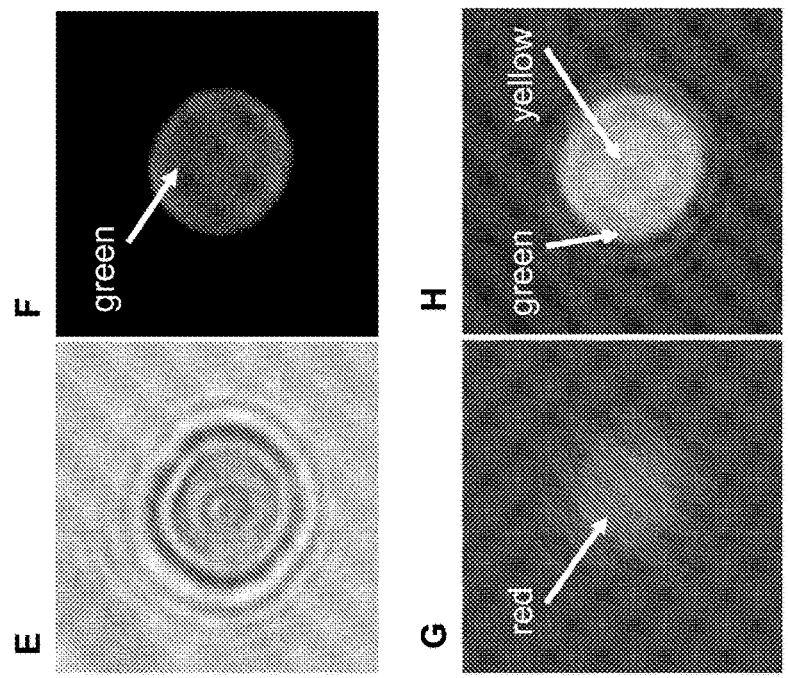

Both red fluorescent Q-dots (emission 565 nm) and green fluorescent PEG-FITC-SWNTs, (emission 510 nm) were simultaneously loaded into the same nanoporous silicon particles (FIG. 23A, Panels A and B). These studies demonstrated that both types of second stage particles could be loaded into the same nanoporous silicon particle carriers. The dynamics of multiple loading were different from the ones described for single loading and reached a stable plateau after 60 minutes. The PEG-FITC-SWNTs were the first to lodge inside the pores probably as a result of their smaller size, while larger Q-dots took more time but reached a higher level of loading (FIG. 23B, Panel C). The release profiles of both types of second stage particles from the silicon carrier remained almost unaltered (FIG. 23B, Panel D) compared to the observations of release, shown in FIG. 21 Panel B. Confocal microscopy images shown in FIG. 23C, Panels E-H, demonstrate that the two different second stage nanovectors preferentially localized to different areas of the silicon particle. Given their larger size, Q-dots were exclusively found in the central area in association with larger pores. PEG-FITC-SWNTs were found around the whole particle, with primary accumulation along the borders of the particle, in association with smaller pores.

Figure 24:
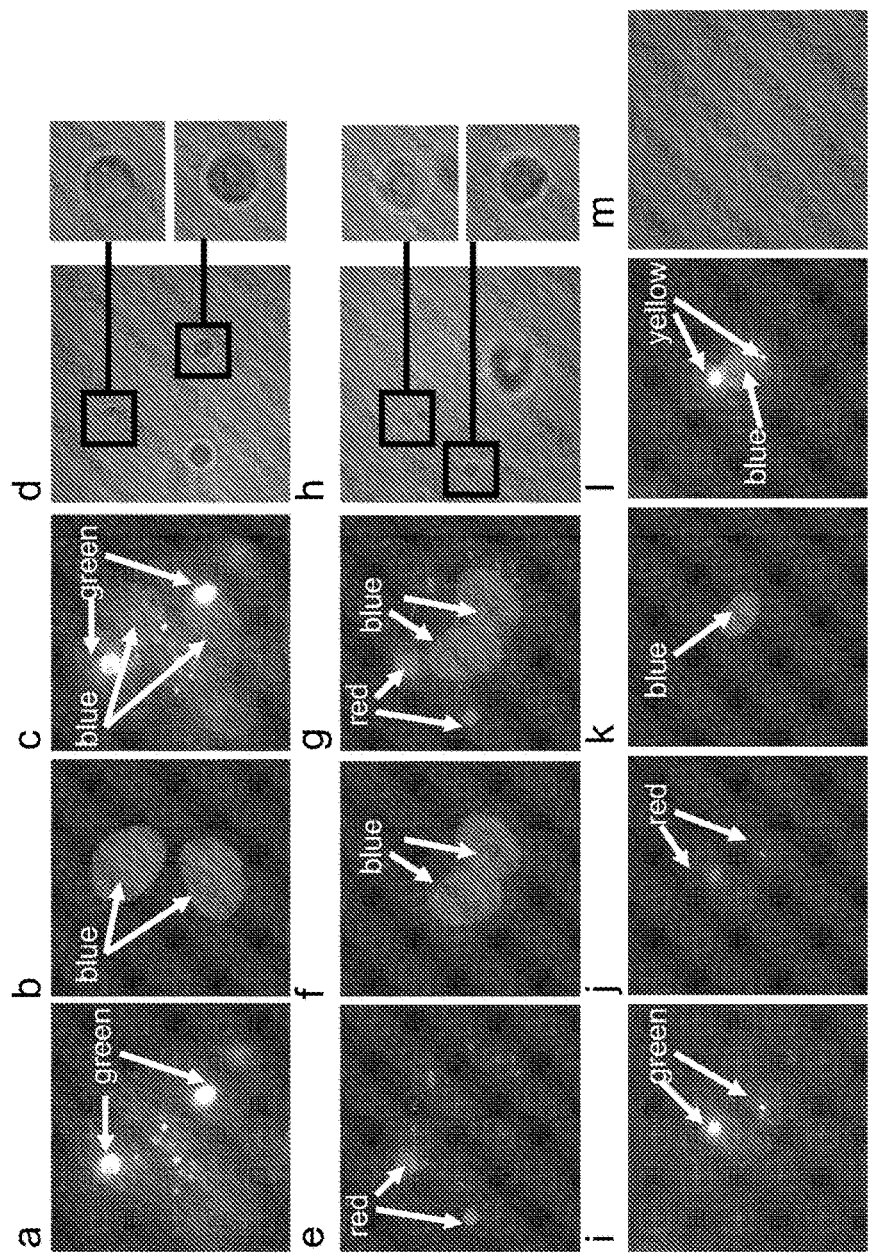
FIG. 24, Panels a-m, show fluorescent spectroscopy images related to incubating nanoporous silicon particles loaded with second stage particles with HUVEC cells for 1 h at 37 C.

When loaded silicon particles were incubated with HUVEC cells for 1 h at 37° C., second stage particles were released locally and selectively internalized by the cells that were reached by the first stage particles. Q-dots (FIG. 24, Panels a-d) and PEG-FITC-SWNTs (FIG. 24, Panels e-h) entered the cytosol of the cells and resulted in significant accumulation inside cytoplasmic vesicles. It was next attempted to deliver both nanoparticles after having loaded them into the first stage silicon particle. Internalization of both nanoparticles occurred with similar kinetics and through the same mechanisms as suggested by the co-localization of the fluorescent signals (FIG. 24, Panels j-m). In all cases, the 3.5 µm silicon particles on their own were not internalized by the cells within the 1 h period. The bright field images in FIG. 24 Panels d, h and m show the details of particle morphology suggesting that they were associated with the external cell surface rather than internalized by the cell, which was also verified by confocal imaging.

Discussion

Silicon is widely used in the microelectronics industry, and has demonstrated its capacity for mass production of microchips as well as for the development of biosensors, implantable devices, and drug delivery systems[36-39]. While bulk silicon remains inert in physiological buffer, porous silicon has a high degree of biodegradability with degradation kinetics that may be finely tuned between hours to days according to pore size density[40,41]. Porous silicon particles degrades to silicic acid, which is harmless to the body and we have found that neither whole intact silicon particles nor their degradation products are cytotoxic for cells. The fabrication protocols may allow the manufacturing of silicon particulates of any desired shape, size (dimensions from 100 nm to hundreds of µm), pore size (5-100 nm), and/or pore density.

In addition, protocols to chemically modify the particles, as attaching PEG to the surface of silicon particles in order to reduce plasma protein adsorption, RES uptake, and to increases the circulation time of the particle as a drug delivery systems[42] (manuscript in preparation) have been developed. Successful conjugation of silicon particles to specific antibodies directed against ligands of therapeutic importance such as vascular endothelial growth factor receptor 2 (VEGFR2) and epidermal growth factor receptor (EGFR) and have evaluated their targeting and selective cytotoxicity using an in-vitro cell culture model of primary HUVEC, as described above in Working Example 1.

Figure 25:
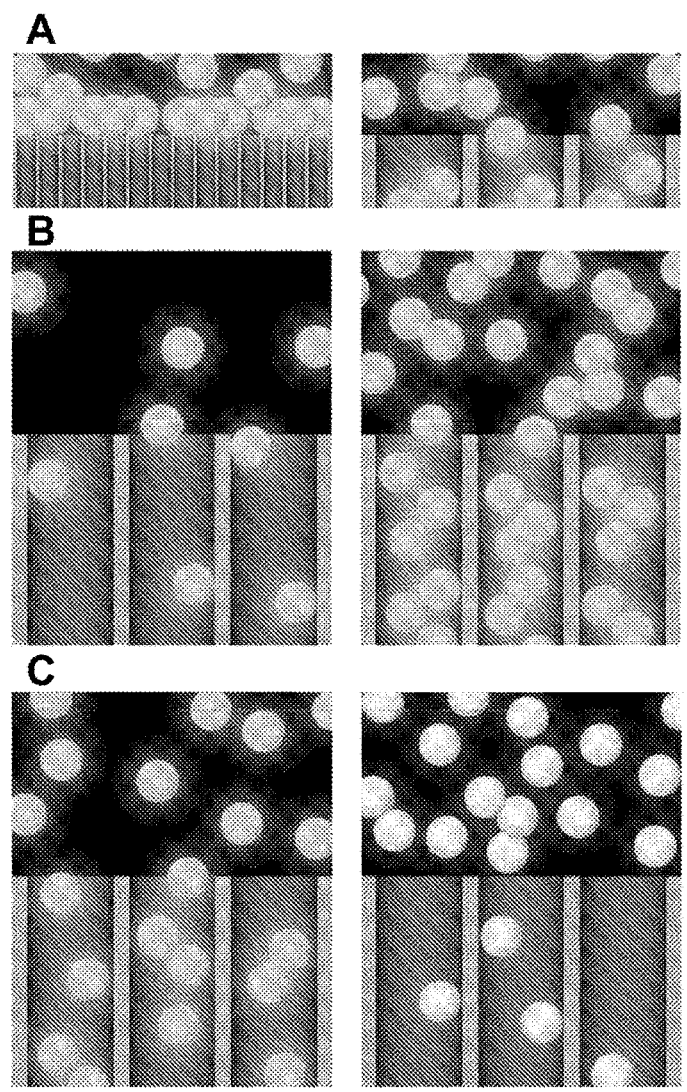
FIG. 25, Panels A-C, present computer models representing the three major physical, chemical and electrostatic mechanisms responsible for loading and release of second stage nanoparticles in first stage silicon carrier. (Panel A) Size Dependency: The size of the pores determines the type of nanoparticles that are preferably loaded into the silicon particle. (Panel B) Dose Dependency: A larger number of nanoparticles in the loading solution cause an increase in the number of particles that are loaded into the pores. (Panel B) Charge Dependency: Compatibly charged nanoparticles will be attracted into the pores, whereas incompatible charges will partially repel the nanoparticles and thus prevent them to enter the pores.

The present studies provide evidence of the ability of efficient loading of nanoporous silicon particles with second stage nanoparticles of different natures, sizes, and shapes. The loading process may be regulated by adjustment of the concentration of nanoparticles and/or by taking advantage of the chemical surface properties of either or both first and second stage particles. The dynamics of nanoparticle release and explored the ability of the nanoporous silicon particles to be loaded with multiple types of nanoparticles simultaneously has been shown in the present studies. These studies have clearly demonstrated that the Q-dots and PEG-FITC-SWNTs used as second stage particles may localize to different compartments of the first stage silicon nanoporous particle carriers according to the size and chemical properties of the second stage particles. Furthermore, the key mechanisms and the driving forces that are responsible for the loading and release processes have been identified and ranked. The relative size of the pores of the silicon particles and of the second stage particles together may determine the most successful configuration of the combination of first and second stage particles (FIG. 25, Panel A). Concentration of the second stage nanovectors influences the efficiency of the loading process, which may be regulated both by passive diffusion and capillary convection of the second stage particles into the nanopores of the silicon particles. Hydrodynamic interactions of the second stage nanovectors with the nanopores of the silicon particles and Brownian motion affects stability of the assembled system and the time that the second stage nanovectors remain loaded inside the nanopores of the first stage silicon particles (FIG. 25, Panel B). Finally, a third mechanism that may be considered is the electrostatic interaction between the first stage silicon particle carrier and the second stage nanovectors (FIG. 25, Panel C). Taken together, each of these features may allow the fine tuning of the amount of second stage nanovectors that may be loaded into the first stage nanoporous silicon particles, which may be matched to a specific pharmacological need in future applications of drug delivery.

The original and unique properties of the multi-stage nanocarrier system may allow multiple therapeutic agents, penetration enhancers or imaging contrast agents to be delivered for the simultaneous detection and then destruction of tumors or for imaging and then treatment of other pathological conditions.

METHODS

Fabrication of Porous Silicon Particles

A heavily doped p++ type Si(100) wafer with a resistivity of 0.005 ohm cm-1 (Silicon Quest International, Santa Clara, Calif., USA) was used as the substrate. A 200 nm layer of silicon nitride was deposited by low-pressure chemical vapor deposition (LPCVD) system. Standard photolithography was used to pattern using a contact aligner (EVG 620 aligner). Silicon particles of small diameter (100-500 nm) were obtained by flash imprint lithography. The nitride was then selectively removed by reactive ion etching (RIE). The photoresist was removed with piranha ($H_2SO_4:H_2O_2=3:1$ (v/v)). The wafer was then placed in a home-make Teflon cell for electrochemical etching. The silicon particles with large pores (LP) were formed in a mixture of hydrofluoric acid (49% HF) and ethanol (3:7 v/v) by applying a current density of 80 mA $cm^{-2}$ for 25 s. A high porosity layer was formed by applying a current density of 320 mA $cm^2$ for 6 s. For fabrication of silicon particles with small pores (SP), a solution of HF and ethanol was used with a ratio of 1:1 (v/v), with a current density applied of 6 mAcm$^{-2}$ for 1.75 min. The high porosity layers were formed by applying a current density of 320 mA $cm^{-2}$ for 6 s in an HF:ethanol mixture with a ratio of 2:5 (v/v). After removing the nitride layer by HF, particles were released by ultrasound in isopropyl alcohol (IPA) for 1 min. The IPA solution containing porous silicon particles was collected and stored at 4° C.

BET Measurement

The nitrogen adsorption desorption volumetric isotherms obtained at 77 K were measured on a Quantachrome Autosorb-3b BET Surface Analyzer. The samples were baked at 150° C. in vacuum overnight. Particle surface area was obtained by BET linearization in the pressure range 0.05 to 1 P/P0. For the LP particles, the BET surface area was 156 $m^2\ g^{-1}$ and pore volume was 0.54 cm3 g-1 using nitrogen adsorption-desorption isotherm measurements. The average pore size was estimated to be about 24.2 nm. For SP particles, the BET surface area was measured 294 $m^2$ g-1; pore volume was 0.38 cm3 $g^{-1}$ and the average pore size was 7.4 nm.

Analysis of Particle Size and Concentration in Solution

Particles were counted using a Z2 Coulter® Particle Counter and Size Analyzer (Beckman Coulter, Fullerton, Calif., USA), with a 50 µm aperture size. The upper and lower size limits for analysis were set at 1.8 and 3.6 µm. For analysis, particles were suspended in the balanced electrolyte solution (ISOTON® II Diluent, Beckman Coulter Fullerton, Calif., USA) and counted. The total volume of original suspension of particles did not exceed 0.3% of the final analysis volume. The particle counter displays the concentration of particles in the solution as well an analysis of the particle size distribution.

Oxidation of Silicon Microparticles

Silicon microparticles in IPA were dried in a glass beaker by heating (80-90° C.) and then oxidized them in a piranha solution (1:2 $H_2O_2$:concentrated $H_2SO_4$ (v/v)). The particles were added to a solution of $H_2O_2$ (30%), sonicated in a 5510R-MT ultrasonic cleaner (BRANSONIC, Danbury, CT, USA) for 30 s and then $H_2SO_4$ (95-98%) was added and the suspension was heated to 100-110° C. for 2 h, with intermittent sonication to disperse the particles. The particles were then washed with deionized (DI) water. Washing of the particles in DI water involves centrifugation of the particulate suspension at 4,200 rpm for 5 min followed by removal of the supernatant and resuspension of the particles in DI water. The oxidized silicon particles were stored at 4° C. in DI water until further use.

Surface Modification of Silicon Particles with 3-Aminopropyltriethoxysilane (APTES)

Prior to silanization, the oxidized silicon particles were hydroxylated in 1.5 M $HNO_3$ for approximately 1.5 h. The particles were then washed 3-5 times with DI water followed by 2 washes with IPA. The silicon particles were then suspended in IPA containing 0.5% (v/v) APTES for 45 min at room temperature. The particles were then washed with IPA (4,200 g for 5 min, 5 times), and stored in IPA at 4° C.

Q-dots and Water Fluorescently Labeled Water-Soluble SWNTs.

Q-dots were purchased from Invitrogen (Carlsbad, Calif., USA). In this study, we used Amino-PEG with 525 nm and 565 nm emission wavelength (catalogue number Q21541MP and Q21531MP respectively) and Carboxyl Q-dots with 525 nm and 565 nm emission wavelength (catalogue number Q21341MP and Q21331MP respectively). To produce ultra-short (US)-SWNTs 43 that are heavily sidewall carboxylated, oleum (20% free $SO_3$, 25 mL) was added to purified HiPco SWNTs (0.100 g) under nitrogen in round bottom flask and the mixture was stirred overnight to disperse the SWNTs (HiPco SWNTs were obtained from the Rice University HiPco laboratory. For the purification established procedures were followed.[44] In a separate flask, oleum (25 mL, 20% free $SO_3$) was slowly added to concentrated nitric acid (18 mL). This mixture was immediately added to the SWNTs and the SWNTs were heated to 60° C. for 2 h. The solution was then slowly poured over ice and filtered over a 0.22 µm polycarbonate membrane. The filter cake was thoroughly washed with water. The vacuum was removed and the cake was dissolved in a minimal amount of methanol after which ether was added leading to flocculation of the US-SWNTs and the vacuum was reapplied. Ether was continually added until a neutral pH was achieved from the washings. The US-SWNT cake was dried under vacuum. To obtain PEGylated SWNTs, US-SWNTs (0.034 g, 3.1 meq C) were dispersed in dry DMF (30 mL) using sonication (bath or cup-horn, and Model) for 30 min in a round bottom flask. To this, Dicyclohexylcarbodiimide (DCC) (0.32 g, 1.5 mmol), and 5,200 MW of hydroxyethyl phthalimide terminated PEG (0.32 g) were added and the mixture stirred under nitrogen for 24 h. The solution was transferred to a dialysis bag (CelluSep H1, 50,000 MWCO, Part #: 1-5050-34, Membrane Filtration Products) for 5 d and the product filtered through glass wool to remove any particulate that formed in the dialysis bag. The contents of the dialysis bag were subjected to removal of the phthalimide moiety revealing the PEG-terminated amine ($H_2H$-PEG-US-SWNT). Hydrazine monohydrate (10 mL) was added to and the solution was heated to reflux under nitrogen for 12 h to give a terminal primary amine on the end of the PEGylated US-SWNT. The product was purified by dialysis in DI water for 5 days. The solution was then transferred to a round bottom flask wrapped in foil and FITC (0.12 g) predissolved in a small amount of DMF was added to the $H_2H$-PEG-US-SWNT solution. The reaction was stirred at room temperature for 12 h. The solution was transferred to a dialysis bag and was kept in continuous dialysis with DI water in the dark for 5 days followed by filtration through glass wool to remove the undissolved particulates. The final product FITC-PEG-US-SWNT contained some FITC physisorbed to the PEG-US-SWNTs instead of being covalently attached. Most of the physisorbed FITC still remains associated with the SWNTs after months of dialysis in water.

Measurement of Zeta Potential of Silicon Particles, Q-dots, and SWNTs

The zeta potential of the silicon particles, Q-dots, and FITC-PEG-US-SWNTs were analyzed using a Zetasizer nano ZS (Malvern Instruments Ltd., Southborough, Mass., USA). The particles were suspended in 20 mM Tris(hydroxymethyl)aminomethane (TRIS-HCL) buffer (pH 7.3) for the analysis.

Loading of Q-dots and SWNTs Into First Stage Silicon Particles

The silicon nanoporous particles that were used in development of the multi-stage nanodevice include LP oxidized porous silicon, SP oxidized porous silicon and APTES modified LP and SP particles. The second stage particles include Amino-PEG Q-dots, Carboxyl Q-dots, and PEG-FITC-SWNTs. Initial experiments were performed to titrate the loading of the second stage particles into the first stage silicon particles. For each experimental point of the titration experiments, 3.0×105 silicon particles were used, which were resuspended in low binding polypropylene micro centrifuge tubes (VWR International, West Chester, Pa., USA) containing 3 µl DI water. For every experiment, the given molarity of TRIS-HCl solution was adjusted at pH 7.3. Either 2 µM Q-dots (5 µl) or 20 ng/µl PEG-FITC-SWNTs (9 µl) were added to the TRIS-HCl solution, with 20 µl as the final volume for the loading experiments. Samples were incubated by being placed on a rotating wheel (20 rpm) for 15 min at 25° C. After incubation, the samples were diluted with 20 mM TRIS-HCl, pH 7.3 to a volume of 150 µl and promptly examined for fluorescence intensity using a FAC-Scalibur (Becton Dickinson) flow cytometer. To evaluate the concentration dependent loading of Q-dots and PEG-FITC-SWNTs into silicon particles, we used 3.0×105 silicon particles and an incubation time of 15 min, with either 0.01, 0.1, 1, 10, 100, 1,000 and 2,000 nM Q-dots or 0.05, 0,1, 2.5, 10 and 20 ng/µl of PEG-FITC-SWNTs. To evaluate the time dependent loading, 3.0×105 first stage particles, 2,000 nM Q-dots or 20 ng/µl of PEG-FITC-SWNTs with incubation times of 15, 30, 45 and 60 minutes were used. For evaluation of loading of silicon particles with both Q-dots and PEG-FITC-SWNTs, 3.0×105 silicon particles, 1,000 nM Q-dots, and 10 ng/µl of PEG-FITC-SWNTs were used with the same final volume of incubation.

Studies of release of Q-dots and SWNTs from first stage silicon particles.

LP silicon particles (2.1×106), which were either oxidized or APTES modified, were combined with 2 µM Amino-PEG Q-dots or Carboxyl Q-dots in a 200 mM TRIS-HCl solution at pH 7.3 or with 20 ng/µl PEG-FITC-SWNTs in a 20 mM TRIS-HCl solution at pH 7.3 or with both 1 μM Q-dots and 10 ng/μl PEG-FITC-SWNTs in a 50 mM TRIS-HCl solution at pH 7.3. The final incubation volume for all studies was 140 μl. Samples of first stage silicon particle carriers and second stage particles were incubated using a rotating wheel (20 rpm) for 15 min at 25° C. The solution containing the first stage silicon particles and second stage particles were then washed in 1.4 mL DI $H_2O$, and then centrifuged for 5 min at 4,200 rpm in a Beckman Coulter Allegra X-22 centrifuge. Pellets present after centrifugation were then resuspended in 70 μl of DI $H_2O$ and 10 μl was removed from each vial to assess the fluorescence of the samples using flow cytometry. Fluorescence was recorded at time 0 and then over 6 time points, which included 30, 60, 90, 180, 360, and 1,200 min. The residual 60 μl left in each vial was diluted to 3 ml in 20 mM TRIS-HCl 0.9% NaCl release buffer, followed by incubation using a rotating wheel (20 rpm) for the given amount of time (30, 60, 90, 180, 360 and 1,200 min) at 37° C. At each time point, samples were centrifuged for 5 min at 4,200 rpm and the fluorescence evaluated using flow cytometry.

Flow Cytometry Setup

Particles were assessed for fluorescence using a FACScalibur (Becton Dickinson). Bivariate dot-plots defining logarithmic side scatter (SSC) versus logarithmic forward scatter (FSC) were used to evaluate the size and shape of the silicon particles (3 μm in diameter, 1.5 μm in height) and to exclude non-specific events from the analysis. Control rainbow BD Calibrite™ beads (3.5 μm in size) were used to calibrate the instrument. A polygonal region (R1) was defined as an electronic gate around the centre of the major population of interest, which excluded events that were too close to the signal-to-noise ratio limits of the cytometer. For each sample, the number of particles detected within the R1 region was above 90%. For analysis of the geometric mean fluorescence intensity (GMFI), dot-plots were created which compared fluorescence channel 1 (FL1) and FL2 versus log FSC with analysis of events falling within the gated region defined as R1. The peaks identified in each of the samples were analyzed in the corresponding fluorescent histogram and the geometric mean values recorded. For particle detection, the detectors used were FSC E-1 and SSC with a voltage setting of 474 volts (V). The fluorescent detector FL1 was set at 800 V. Green fluorescence (FITC and Q-dots 525) was detected with FL1 using a 530/30 nm band-pass filter. Red fluorescence (Q-dots 565) was detected using FL2. When single color detection only was analyzed, color compensation was set at zero, and when dual red-green color detection was performed, FL1 compensation was set at 25% of FL2 and FL2 compensation was set at 35% of FL1. Instrument calibration was carried out before, in between, and after each series of experiments for data acquisition using BD Calibrite™ beads.

Scanning Electron Microscopy

The morphology of the silica particles was acquired using scanning electron microscopy (SEM, model LE01530). Particles were directly placed on SEM samples stage and dried. For the particles tested in the high salt buffers, a mild washing step in DI water was performed before putting on the stage. The acceleration voltage was 10 kV.

Tapping Mode Atomic Force Microscopy (AFM)

AFM samples were prepared by deposition from DMF onto a freshly cleaved mica surface. Samples were spin coated and sectional analysis was used to determine the heights of each sample. AFM samples were obtained using tapping mode.

Bright Field Microscopy

Particles were analyzed in bright field contrast with an Olympus CKX41 microscope with a 40× magnification lens. Images were taken with an SP-350 Olympus True-Pic TURBO Image Processor camera.

Fluorescent Microscopy

Fluorescent imaging of particles was performed with a Nikon Eclipse TE2000-E with a DQC-FS Nikon CCD Camera kept at −30.1° C. All the samples were mounted immediately before the analysis and the images acquired with a 63× immersion oil objective. The microscope settings were kept constant throughout all the experiments. numerical aperture was set at 1.4, refractive index at 1.515, exposure time at 500 ms, readout Speed at 10 MHz and conversion gain at 1/6×.

The images were analyzed and measured with the NIS Elements AR 2.3 Software.

Confocal Microscopy

Confocal imaging of particles was performed with a LEICA DM6000 microscope. All the samples were mounted immediately before the analysis and the images acquired with a HCX PL APO CS 63× immersion oil objective with a 1.4 numerical aperture and 1.52 refraction index. For all the acquisitions, the pinhole was set at 95.6 μm (1 Airy unit), both 488 nm argon and 561 nm lasers were at 15% of their capacity; the scan speed was set at 400 Hz. The single green fluorescence imaging photomultiplier voltage was set at 750 V. For dual color imaging, the PMT for the red channel was set at 600 V while the PMT for the green channel was set at 1000 V. To improve the image quality, 2-frame accumulation, 2-line accumulations and 4-frame averages were performed during acquisitions. Final voxel width and height were 19.8 nm. The images were magnified digitally (10×) and a median adjustment (3 pixels, 2 rounds) was used during the post-processing using the LAS AF 1.6.2 software.

WORKING EXAMPLE 3

Liposomes in 3.5 Micron Silicon Particles

Fluorescently labeled siRNA loaded 1,2-dioleoyl-sn-glycero-3-phosphaticholine (DOPC) liposomes were prepared as detailed in C. N. Landen Jr., et al. Cancer Res. 2005, 65(15), 6910-6918, and J. Clin. Cancer Res. 2006; 12(16), 4916-4924.

Figure 8A:
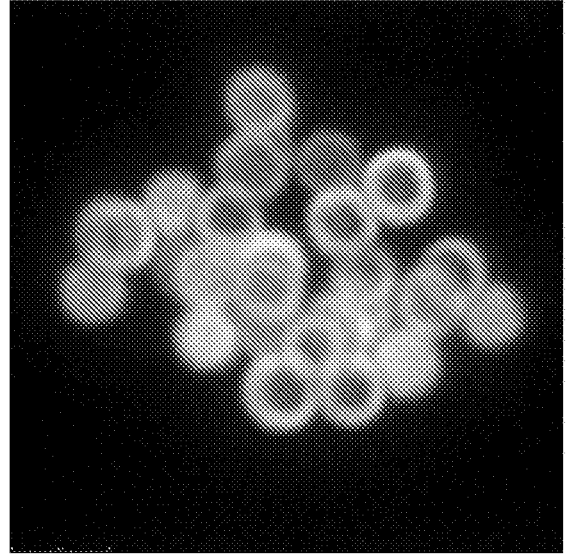
FIGS. 8A-B present data for lipid based second stage particles loading into nanoporous silicon first stage particles.
Figure 8A:
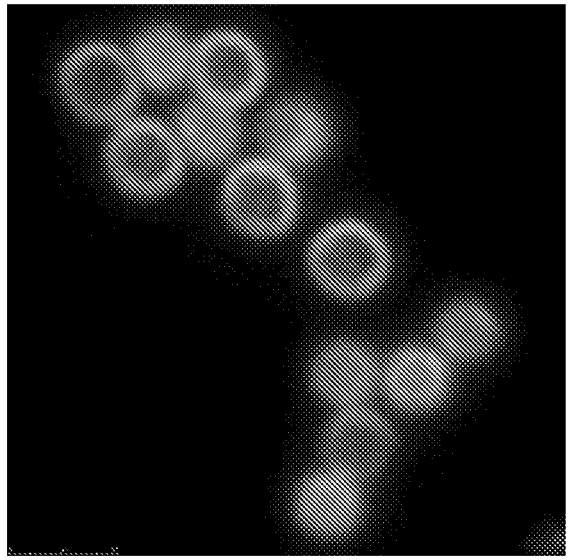
Figure 8B:
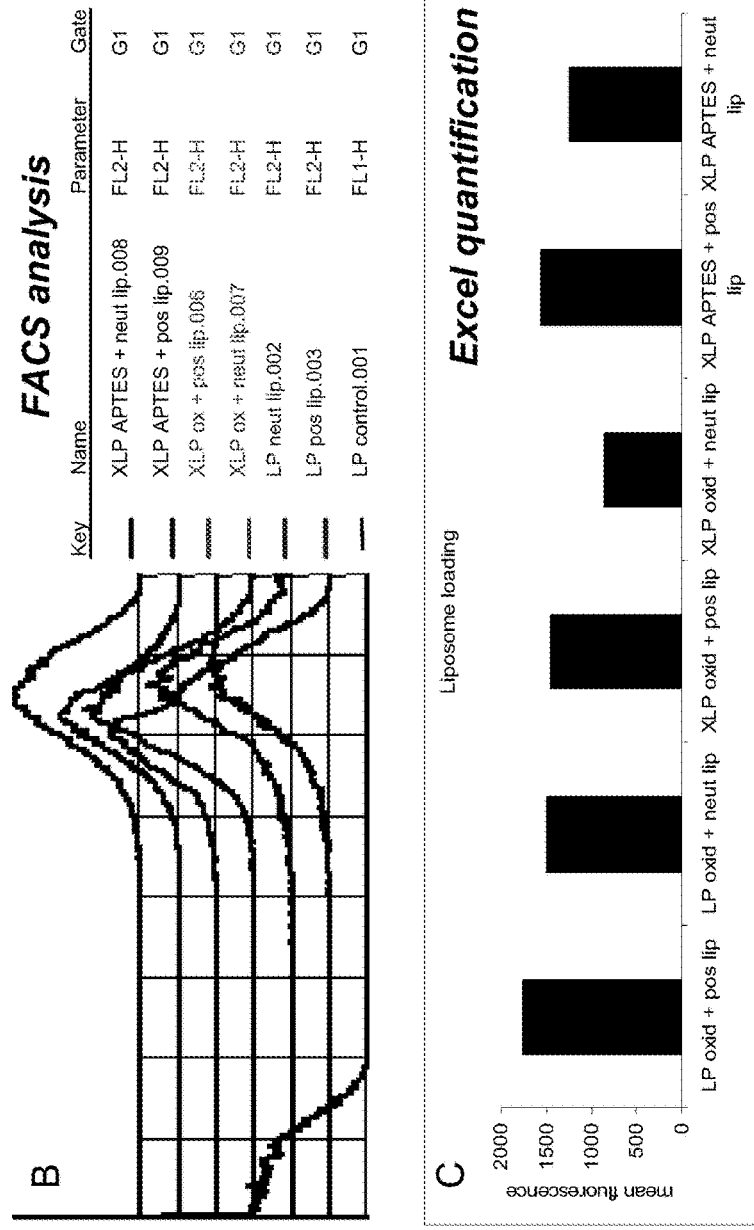
Figure 9A:
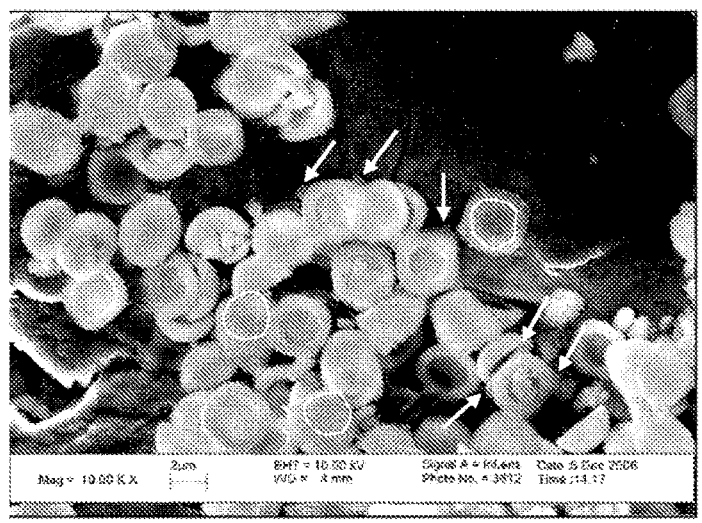
FIGS. 9A-9D demonstrate Scanning Electron Microscopy (SEM) images of "large pore" (LP) nanoporous silicon first stage particles.
Figure 9B:
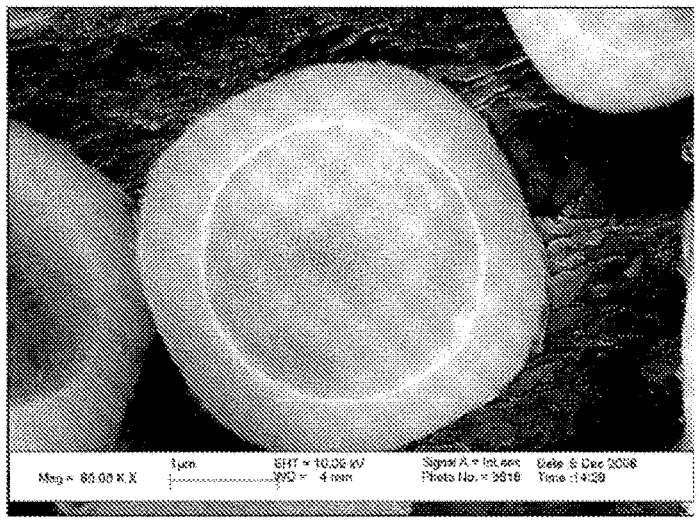
Figure 9C:
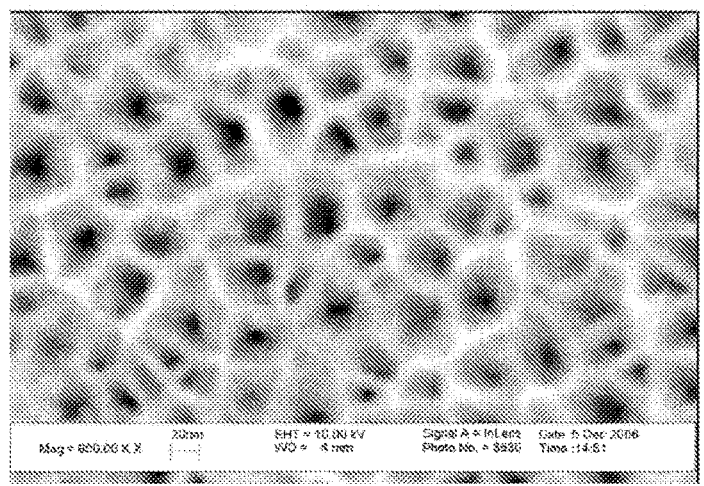
Figure 9D:
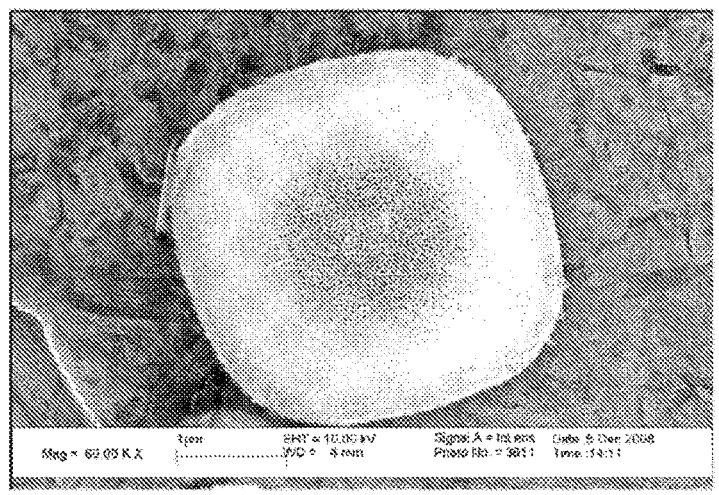
Figure 26:
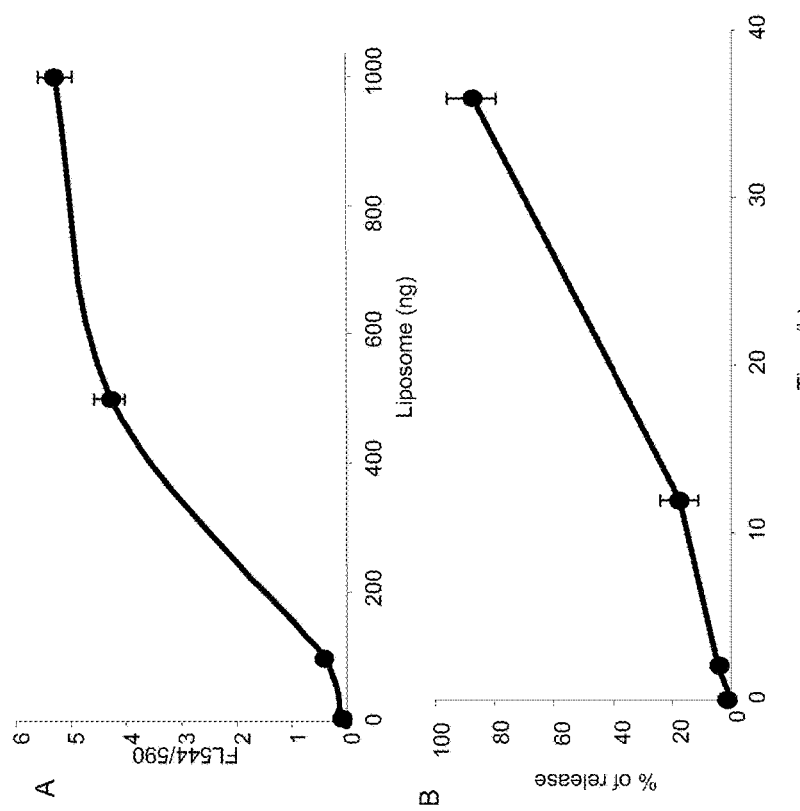
FIG. 26, Panels A-B, present data for liposomes containing SiRNA loaded into nanoporous silicon first stage particles. Panel A: Alexa 555 fluorescently labeled siRNAs were encapsulated into nano-liposomes and loaded into the 1st stage nano-vectors. The data show that the fluorescence associated with the porous Silicon carrier increased with the amount of nanoliposomes. Y axis reads mean fluorescence in Panel A.
Figure 27:
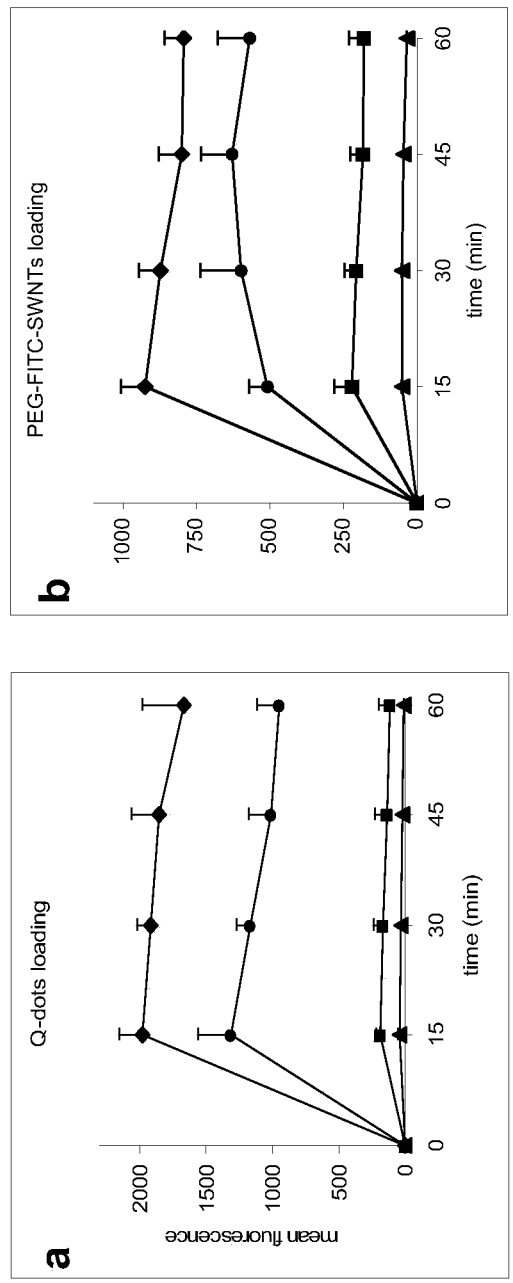
FIG. 27 demonstrates optimization of physical condition for loading of quantum dots and PEG-FITC-SWNTs. Y axis in Panel a and Panel b reads mean fluorescence. Porous silicon particles were desiccated in a desiccator over night and then mixed with the loading solution containing the second stage nanoparticles. Loading efficiency in dry condition was not significantly different than loading efficiency in a wet environment (p value>0.5).

Fluorescently labeled siRNA loaded DOPC liposomes (original siRNA concentration: 100 ng/μl), as second stage particles, were mixed with 1st stage large pore "LP" oxidized silicon particles (3.5 micron). Incubation was performed in 20 mM Tris pH 7.3 for 30 min at room temperature. The solution was spun down at 4,200 rpm for 1 min at room temperature. The supernatant was recovered and the fluorescence of the sample was measured by fluorimetry using 544 nm/590 nm (excitation/emission) settings. The particle pellet comprising the 1st stage particles that had incorporated the fluorescent liposomes were resuspended in 100 μl of deionized water and fluorimetric readings were taken. The loading time dynamics of Fluorescently labeled siRNA loaded DOPC liposomes into 3.5 micron LP and SP particles is shown in FIG. 8B, Panel D. In FIG. 8B, Panels E and F show fluorescent microscopy images visualizing second stage liposomes containing Alexa 555 labeled SiRNA into 3.5 micron nanoporous silicon first stage particles LP in white field and red field respectively Alexa 555 fluorescently labeled siRNAs were encapsulated into liposomes and loaded into the 1st stage porous silicon particles. The data in FIG. 26, Panel A, show that the fluorescence associated with the porous Silicon carrier increased with the amount of nanoliposomes.

To test the release of liposome from 1st stage particles, the assembled multistage systems were incubated with 10% fetal bovine serum (pH 7.4) and release of nanoliposomes from the 1st stage particles was followed along time using fluorimetry. Complete unloading was achieved in about 36 h, see FIG. 26, Panel B.

WORKING EXAMPLE 4

Liposomes tn Silicon Particles
Preparation of Liposomes:

Liposomes with a lipid composition of 58:40:2 (Mol %) DPPC: Cholesterol: DSPE-Methoxy PEG (2000) respectively may be made by the extrusion process as follows: Briefly, the lipids may be dissolved in ethanol at 55 oC. The dissolved lipids may then be hydrated with 300 mM ammonium sulfate solution (for 15-30 minutes) to facilitate active loading of doxorubicin, see Li, et al. Biochim et Biophys Acta 1415 (1998). Liposomes may be extruded through a series of Nuclepore track-etched polycarbonate membranes of decreasing pore sizes. The liposomes may then be extruded 5 times through a 0.2 µm membrane. This may be followed by an extrusion through 0.1 µm membrane (5 times), then through a 0.05 µm membrane (5 times). The final extrusion may be through a 0.03 µm membrane (10 times). The extrusions may be carried out at 55 oC.

Produced fluorescently labeled liposomes contained 30% of DiPalmitoylPhosphatidylCholine(DPPC) lipids, 30% of cholesterol, 10% of fluorescently labeled lipid N-[7-nitrobenz-2-oxa-1,3-diazol-4-yl] dipalmitoyl-L-α-phosphatidylethanolamine (NBD-PE) lipid mixed with either 30% 1,2-Dioleyl-3-trymethylammoniumpropane (DOTAP) (for cationic liposomes), or 30% dioleoylphosphatidyl glycerol (DOPG) (for anionic liposomes), or 30% dioleoylphosphatidyl choline DOPC (for neutral liposomes).

Neutral liposomes had initial mean diameter 47.4 nm and mean diameter after 3 days 78.2 nm as determined by Dynamic Light Scattering (DLS). Zeta potential of neutral liposomes was −13.04±0.77 mV.

Cationic liposomes had initial mean diameter 49.6 nm and mean diameter after 3 days 58.2 nm as determined by DLS. Zeta potential of cationic liposomes was 30.30±2.55 mV.

Neutral and cationic liposomes were loaded in 1 micron "large pore" (LP) oxidized nanoporous silicon particles and 1 micron "large pore" (XLP) oxidized and APTES modified silicon particles. FIG. 8A, Panel A, shows confocal microscopy images of neutral (left) and cationic (right) fluorescently labeled liposomes loaded into 1 micron XLP APTES modified silicon particles. FIG. 8A, Panel B, shows FACS analysis for neutral and cationic fluorescently labeled liposomes loaded into 1 micron XLP oxidized and APTES modified silicon particles and 1 micron LP oxidized particles. FIG. 8A, Panel C shows Excel quantification of fluorescently labeled liposome loading.

Loading of Doxorubicin as an Active Agent:

The liposomes may be dialyzed overnight against 150 mM NaCl to remove unencapsulated ammonium sulfate to generate a trans-membrane proton gradient. Doxorubicin (~10 mg/ml) may be added to the liposomes at 60° C. for 1 hr. The drug:lipid ratio will be 0.2:1.0 and the final lipid concentration will be ~25 mM. The resulting liposomal formulation may be kept on ice for 15 minutes to stop the remote loading process. The liposomes may be dialyzed overnight against 150 mM NaCl to remove unencapsulated doxorubicin. The final encapsulated Doxorubicin concentration may be determined by lysis with methanol (30% of final volume) and measuring the UV absorbance at 480 nm.

REFERENCES

The following references are cited in the foregoing text:
1. Cheng, M. M. et al. Nanotechnologies for biomolecular detection and medical diagnostics. *Curr Opin Chem Biol* 10, 11-9 (2006).
2. Ferrari, M. Cancer nanotechnology: opportunities and challenges. *Nat Rev Cancer* 5, 161-71 (2005).
3. Moghimi, S. M., Hunter, A. C. & Murray, J. C. Nanomedicine: current status and future prospects. *Faseb J* 19, 311-30 (2005).
4. Sullivan, D. C. & Ferrari, M. Nanotechnology and tumor imaging: seizing an opportunity. *Mol Imaging* 3, 364-9 (2004).
5. Wang, M. D., Shin, D. M., Simons, J. W. & Nie, S. Nanotechnology for targeted cancer therapy. *Expert Rev Anticancer Ther* 7, 833-7 (2007).
6. Lasic, D. D. Doxorubicin in sterically stabilized liposomes. *Nature* 380, 561-2 (1996).
7. Uziely, B. et al. Liposomal doxorubicin: antitumor activity and unique toxicities during two complementary phase I studies. *J Clin Oncol* 13, 1777-85 (1995).
8. Kim, S. et al. Near-infrared fluorescent type II quantum dots for sentinel lymph node mapping. *Nat Biotechnol* 22, 93-7 (2004).
9. So, M. K., Xu, C., Loening, A. M., Gambhir, S. S. & Rao, J. Self-illuminating quantum dot conjugates for in vivo imaging. *Nat Biotechnol* 24, 339-43 (2006).
10. Corot, C., Robert, P., Idee, J. M. & Port, M. Recent advances in iron oxide nanocrystal technology for medical imaging. *Adv Drug Deliv Rev* 58, 1471-504 (2006).
11. Liu, Z. et al. In vivo biodistribution and highly efficient tumour targeting of carbon nanotubes in mice. *Nature Nanotechnology* 2, 47-52 (2007).
12. Hirsch, L. R. et al. Nanoshell-mediated near-infrared thermal therapy of tumors under magnetic resonance guidance. *Proc Natl Acad Sci USA* 100, 13549-54 (2003).
13. Bradbury, J. Nanoshell destruction of inoperable tumours. *Lancet Oncol* 4, 711 (2003).
14. Torchilin, V. P. Multifunctional nanocarriers. *Adv Drug Deliv Rev* 58, 1532-55 (2006).
15. Bianco, R., Daniele, G., Ciardiello, F. & Tortora, G. Monoclonal antibodies targeting the epidermal growth factor receptor. *Curr Drug Targets* 6, 275-87 (2005).
16. Ciardiello, F. & Tortora, G. A novel approach in the treatment of cancer: targeting the epidermal growth factor receptor. *Clin Cancer Res* 7, 2958-70 (2001).
17. Hobday, T. J. & Perez, E. A. Molecularly targeted therapies for breast cancer. *Cancer Control* 12, 73-81 (2005).
18. Druker, B. J. Perspectives on the development of a molecularly targeted agent. *Cancer Cell* 1, 31-6 (2002).
19. Sakamoto, J., Annapragada, A., Decuzzi, P. & Ferrari, M. Anti-Biological Barrier Nanovector Technology for Cancer Applications *Expert Opin Drug Deliv* (In Press: Accepted May 2007) (2007).
20. Ferrari, M. Nanovector therapeutics. *Curr Opin Chem Biol* 9, 343-6 (2005).
21. Decuzzi, P. & Ferrari, M. Fantastic voyages. *Mechanical Engineering* 128, 24-27 (2006).
22. Decuzzi, P., Causa, F., Ferrari, M. & Netti, P. A. The effective dispersion of nanovectors within the tumor microvasculature. *Ann Biomed Eng* 34, 633-41 (2006).

23. Decuzzi, P. & Ferrari, M. The adhesive strength of non-spherical particles mediated by specific interactions. *Biomaterials* 27, 5307-14 (2006).
24. Decuzzi, P. & Ferrari, M. The role of specific and non-specific interactions in receptor-mediated endocytosis of nanoparticles. *Biomaterials* 28, 2915-22 (2007).
25. Decuzzi, P., Lee, S., Bhushan, B. & Ferrari, M. A theoretical model for the margination of particles within blood vessels. *Ann Biomed Eng* 33, 179-90 (2005).
26. Decuzzi, P., Lee, S., Decuzzi, M. & Ferrari, M. Adhesion of microfabricated particles on vascular endothelium: a parametric analysis. *Ann Biomed Eng* 32, 793-802 (2004).
27. Corrie, S. R., Lawrie, G. A. & Trau, M. Quantitative analysis and characterization of biofunctionalized fluorescent silica particles. *Langmuir* 22, 2731-7 (2006).
28. Mansur, H. S., Orefice, R. L., Vasconcelos, W. L., Lobato, Z. P. & Machado, L. J. Biomaterial with chemically engineered surface for protein immobilization. *J Mater Sci Mater Med* 16, 333-40 (2005).
29. Shriver-Lake, L. C. et al. Antibody immobilization using heterobifunctional crosslinkers. *Biosens Bioelectron* 12, 1101-6 (1997).
30. Starodub, N. F., Pirogova, L. V., Demchenko, A. & Nabok, A. V. Antibody immobilisation on the metal and silicon surfaces. The use of self-assembled layers and specific receptors. *Bioelectrochemistry* 66, 111-5 (2005).
31. Lan, S., Veiseh, M. & Zhang, M. Surface modification of silicon and gold-patterned silicon surfaces for improved biocompatibility and cell patterning selectivity. *Biosens Bioelectron* 20, 1697-708 (2005).
32. Wang, Y. C. & Ferrari, M. Surface modification of micromachined silicon filters. *Journal of Materials Science* 35, 4923-4930 (2000).
33. Buriak, J. M. Organometallic chemistry on silicon and germanium surfaces. *Chem Rev* 102, 1271-308 (2002).
34. Desai, T. A. et al. Microfabricated immunoisolating biocapsules. *Biotechnol Bioeng* 57, 118-20 (1998).
35. Schreiber, F. Structure and growth of self-assembling monolayers. *Progress in Surface Science* 65, 151-256 (2000).
36. Foraker, A. B. et al. Microfabricated porous silicon particles enhance paracellular delivery of insulin across intestinal Caco-2 cell monolayers. *Pharm Res* 20, 110-6 (2003).
37. Lin, V. S., Motesharei, K., Dancil, K. P., Sailor, M. J. & Ghadiri, M. R. A porous silicon-based optical interferometric biosensor. *Science* 278, 840-3 (1997).
38. Desai, T. A., Hansford, D. J., Leoni, L., Essenpreis, M. & Ferrari, M. Nanoporous anti-fouling silicon membranes for biosensor applications. *Biosens Bioelectron* 15, 453-62 (2000).
39. Gardner, P. Microfabricated nanochannel implantable drug delivery devices: trends, limitations and possibilities. *Expert Opin Drug Deliv* 3, 479-87 (2006).
40. Prestidge, C. A. et al. Mesoporous silicon: a platform for the delivery of therapeutics. *Expert Opin Drug Deliv* 4, 101-10 (2007).
41. Canham, L. T. Bioactive silicon structure fabrication through nanoetching techniques. *Advanced Materials* 7, 1033-& (1995).
42. Zhang, M., Desai, T. & Ferrari, M. Proteins and cells on PEG immobilized silicon surfaces. *Biomaterials* 19, 953-60 (1998).
43. Chen, Z. et al. Soluble ultra-short single-walled carbon nanotubes. *J Am Chem Soc* 128, 10568-71 (2006).
44. Saini, R. K. et al. Covalent sidewall functionalization of single wall carbon nanotubes. *J Am Chem Soc* 125, 3617-21 (2003).
45. Canham, L. T. (1995). "Bioactive silicon structure fabrication through nanoetching techniques." *Advanced Materials* 7(12): 1033-1037.
46. Canham, L. (1997). Properties of Porous Silicon. London, INSPEC - Institution of Electrical Engineers.
47. Mayne, A. H., Bayliss, S.C., Barr, P., Tobin, M., Buckberry, L.D. (2000). "Biologically Interfaced Porous Silicon Devices." *Physica Status Solidi* 182(1): 505-513.
48. Low, S. P., K. A. Williams, et al. (2006). "Evaluation of mammalian cell adhesion on surface-modified porous silicon." *Biomaterials* 27(26): 4538-46.
49. Becker M. L., et. al. *Chem. Commun.* (Camb) 2003: 180-181
50. Duncan R. *Nat Rev Drug. Discov.* 2003, 2:347-360.
51. La Van D. A., et. al. *Nat. Biotechnol.* 21, 10:184-1191, 2003.
52. Nakanishi T., et. al.: *J. Control. Release* 2001, 74:295-302.
53. Soppimath K. S., et. al. *J. Control. Release* 2001, 70:1-20.
54. Cloninger M. J.*Curr. Opin. Chem. Biol.* 2002, 6:742-748.
55. Gilles E. R., et. al. *J. Am. Chem. Soc* 2002, 124:14137-14146.
56. Quintana A, et. al. *Pharm. Res.* 2002, 19:1310-1316.
57. Charnay C, et. al. *J. Phys. Chem. B* 2003, 107:7327-7333.
58. Hirsch L. R., et. al. *Proc. Natl. Acad. Sci. USA* 2003, 100:13549-13554.
59. Loo C, et. al. *Technol. Cancer Res. Treat.* 2004, 3:33-40.
60. O'Neal D P, et. al. *Cancer Lett.* 2004, 209:171-176.
61. Akerman M. E., et. al. *Proc. Natl. Acad. Sci. USA* 2002, 99:12617-12621.
62. Derfus A. M., *Nano Lett.* 2004, 4:11-18.
63. Ishii D, et. al. *Nature* 2003, 423:628-632.
64. Raja K. S., et. al. *Biomacromolecules* 2003, 4:472-476.
65. He X. X., et. al. *J. Am. Chem. Soc.* 2003, 125:7168-7169.
66. Vijayanathan V., et. al. *Biochemistry* 2002, 41:14085-14094.
67. Cohen M. H., et. al. *Biomedical Microdevices* 2003, 5:253-259.
68. Ferrari M, US Patent No. 6,107,102, issued August 22, 2000.
69. Yan F., et. al. *Photoch. Photobiol.* 2003, 78:587-591.
70. Yan F., et. al. *J. Nanosci. Nanotechnol.* 2004, 4:72-76.
71. Oyewumi M. O., et. al. *Bioconjug. Chem.* 2002, 13:1328-1335.
72. Ferrari M et. al.: U.S. Pat. No. 6,355,270, issued Mar. 12, 2002.
73. Martin F J, et. al. US Patent Application Publication No. 2003/0114366, published Jun. 19, 2003.
74. Ferrari M. Current Opinion in Chemical Biology 2005, 9:343-346.
75. Ferrari M., Nat. Rev. Cancer. 2005 5(3):161-71.

Although the foregoing refers to particular preferred embodiments, it will be understood that the present invention is not so limited. It will occur to those of ordinary skill in the art in light of this disclosure that various modifications may be made to the disclosed embodiments and that such modifications are intended to be within the scope of the present invention. All of the publications, patent applications and patents cited in this specification are incorporated herein by reference to the extent that they provide details and description consistent with and supplemental to this disclosure.

The invention claimed is:

1. A multistage delivery composition comprising:
a first stage particle containing second stage particle, wherein the first stage particle, comprises:
(i) a body;
(ii) at least one surface with a surface charge; and
(iii) a plurality of nanoscale reservoirs in the body of the first stage particle,
wherein each reservoir is connected to at least one surface of the body through at least one channel,
wherein the at least one channel is in the form of a pore open to the surface,
wherein at least one of the plurality of the nanoscale reservoirs contains the second stage particle in the pore open to the surface, and wherein:
the first stage particle is biodegradable and has a selected non-spherical shape;
the first stage particle is a porous micro or nanoparticle with a size from about 100 nm to about 5 microns;
the second stage particle encapsulates a therapeutic agent;
the first stage particle is configured to overcome a first biological barrier; and
the second stage particle is configured to overcome a second biological barrier, wherein the first stage particle and the second stage particle are configured to sequentially overcome the first biological barrier and second biological barrier respectively.

2. The multistage delivery composition of claim 1 wherein the first stage particle is configured to release the second stage particle for delivery of the therapeutic agent.

3. The multistage delivery composition of claim 1 wherein the first stage particle is configured to release the second stage particle for delivery of the therapeutic agent via diffusion of the second stage particle through the channels in the first stage particle.

4. The multistage delivery composition of claim 1 wherein the first stage particle is configured to release the second stage particle for delivery of the therapeutic agent via degradation or erosion of the body the first stage particle.

5. The multistage delivery composition of claim 1 wherein the first biological barrier and the second biological barrier are each independently selected from the group of biological barriers consisting of a hemo-rheology barrier, a reticulo-endothelial system barrier, an endothelial barrier, a blood brain barrier, a tumor-associated osmotic interstitial pressure barrier, an ionic and molecular pump barrier, a cell membrane barrier, an enzymatic degradation barrier, a nuclear membrane barrier, and any combination of thereof.

6. The multistage delivery composition of claim 1 wherein the first stage particle comprises a chemical targeting moiety disposed on the surface of the first stage particle, wherein said chemical targeting moiety comprises at least one moiety selected from the group consisting of dendrimer, an aptamer, an antibody, a biomolecule and any combination thereof.

7. The multistage delivery composition of claim 1 wherein at least one of the plurality of nanoscale reservoirs contains at least one additional agent.

8. The composition of claim 7, wherein the at least one additional agent comprises at least one penetration enhancer, at least one additional active agent, or at least one targeting moiety.

9. The composition of claim 8, wherein the at least one penetration enhancer is selected from the group consisting of a basement membrane permeation enhancer, a tight junction protein (tjp) permeation enhancer and any combination thereof.

10. The composition of claim 1, wherein the first stage particle is configured to release the second stage particle in response to an external stimulus.

11. A method comprising administering to a subject a composition comprising:
a first stage particle containing a second stage particle, wherein the first stage particle comprises:
(i) a body;
(ii) at least one surface with a surface charge; and
(iii) a plurality of nanoscale reservoirs in the body of the first stage particle,
wherein each reservoir is connected to at least one surface of the body through at least one channel,
wherein the at least one channel is in the form of a pore open to the surface,
wherein at least one of the plurality of the nanoscale reservoirs contains the second stage particle in the pore open to the surface, and wherein:
the first stage particle is biodegradable and has a selected non-spherical shape;
the first stage particle is a porous micro or nanoparticle with a size from about 100 nm to about 5 microns;
the second stage particle encapsulates a therapeutic agent;
the first stage particle is configured to overcome a first biological barrier; and the second stage particle is configured to overcome a second biological barrier, wherein the first stage particle and the second stage particle are configured to sequentially overcome the first biological barrier and second biological barrier respectively.

12. The method of claim 11 wherein the first stage particle is configured to release the second stage particle for delivery of the therapeutic agent.

13. The method of claim 11 wherein the first biological barrier and the second biological barrier are each independently selected from the group of biological barriers consisting of a hemo-rheology barrier, a reticulo-endothelial system barrier, an endothelial barrier, a blood brain barrier, a tumor-associated osmotic interstitial pressure barrier, an ionic and molecular pump barrier, a cell membrane barrier, an enzymatic degradation barrier, a nuclear membrane barrier, and any combination of thereof.

14. The method of claim 11 wherein the first stage particle comprises a chemical targeting moiety disposed on the surface of the first stage particle, wherein said chemical targeting moiety comprises at least one moiety selected from the group consisting of dendrimer, an aptamer, an antibody, a biomolecule and any combination thereof.

15. The method of claim 11 wherein the at least one of the plurality of nanoscale reservoirs contains at least one additional agent.

16. The method of claim 11 wherein the at least one additional agent comprises at least one penetration enhancer, at least one additional active agent, or at least one targeting moiety.

17. The method of claim 11 wherein the composition is administered intravascularly.

18. A method of fabricating a multistage delivery composition, comprising:
(a) providing a first stage particle, wherein the first stage particle comprises:
(i) a body;
(ii) at least one surface with a surface charge; and (iii) a plurality of nanoscale reservoirs in the body of the first stage particle,
wherein each reservoir is connected to at least one surface of the body through at least one channel,
wherein the at least one channel is in the form of a pore open to the surface, and wherein:
the first stage particle is biodegradable and has a selected non-spherical shape;
the first stage particle is a porous micro or nanoparticle with a size from about 100 nm to about 5 microns;
(b) providing a second stage particle; and
(c) loading the second stage particle inside one of the plurality of nanoscale reservoirs of the first stage particle such that the nanoscale reservoir contains the second stage particle in the pore open to the surface, and such that the first stage particle is configured to overcome a first biological barrier and the second stage particle is configured to overcome a second biological barrier, wherein the first stage particle and the second stage particle are configured to sequentially overcome the first biological barrier and second biological barrier respectively.

19. The method of claim 18, wherein loading the second stage particle inside one of the plurality of nanoscale reservoirs of the first stage particle comprises placing the first stage particle and the second stage particle in a sealed chamber having a pressure above atmospheric pressure.

20. The method of claim 19 wherein first stage particle and the second stage particle are submerged in a solution in the sealed chamber.

21. The method of claim 20 wherein the first stage particle is subjected to reduced pressure prior to being placed in the solution in the sealed chamber.

22. The of method claim 18, wherein loading the second stage particle inside one of the plurality of nanoscale reservoirs of the first stage particle comprises loading via passive diffusion or capillary convection, or by a combination of those.

23. The method of claim 18 wherein loading the second stage particle inside one of the plurality of nanoscale reservoirs of the first stage particle comprises modifying a surface charge of the first particle or the second particle.

24. The multistage delivery composition of claim 1, wherein the second stage particle comprises a plurality of second stage particles stacked within the pore open to the surface.

25. The method of claim 11, wherein the second stage particle comprises a plurality of second stage particles stacked within the pore open to the surface.

26. The method of claim 18, wherein the second stage particle comprises a plurality of second stage particles stacked within the pore open to the surface.

27. The multistage delivery composition of claim 1, wherein the second stage particle comprises at least one constituent selected from the group consisting of a liposome, a micelle, an ethosome, a carbon nanotube, a fullerene nanoparticle, a metal nanoparticle, a semiconductor nanoparticle, a polymer nanoparticle, an oxide nanoparticle, a viral particle, a polyionic particle and a ceramic particle.

28. The method of claim 11, wherein the second stage particle comprises at least one constituent selected from the group consisting of a liposome, a micelle, an ethosome, a carbon nanotube, a fullerene nanoparticle, a metal nanoparticle, a semiconductor nanoparticle, a polymer nanoparticle, an oxide nanoparticle, a viral particle, a polyionic particle and a ceramic particle.

* * * * *